US012571037B2

(12) United States Patent
Mandell et al.

(10) Patent No.: US 12,571,037 B2
(45) Date of Patent: **\*Mar. 10, 2026**

(54) SYSTEMS AND METHODS USING MAGNETICALLY-RESPONSIVE SENSORS FOR DETERMINING A GENETIC CHARACTERISTIC

(71) Applicant: Illumina, Inc., San Diego, CA (US)

(72) Inventors: Jeffrey G. Mandell, Rancho Santa Fe, CA (US); Lisa Kwok, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 798 days.

This patent is subject to a terminal disclaimer.

(21) Appl. No.: 17/980,341

(22) Filed: Nov. 3, 2022

(65) Prior Publication Data

US 2023/0082589 A1      Mar. 16, 2023

Related U.S. Application Data

(63) Continuation of application No. 15/752,192, filed as application No. PCT/US2016/046888 on Aug. 12, 2016, now Pat. No. 11,512,348.

(60) Provisional application No. 62/205,336, filed on Aug. 14, 2015.

(51) Int. Cl.
| | |
|---|---|
| *C12Q 1/6869* | (2018.01) |
| *B01L 3/00* | (2006.01) |
| *C12Q 1/6874* | (2018.01) |
| *G01N 27/327* | (2006.01) |
| *G01N 33/543* | (2006.01) |
| *G01R 33/09* | (2006.01) |
| *G01R 33/12* | (2006.01) |

(52) U.S. Cl.
CPC ...... *C12Q 1/6874* (2013.01); *B01L 3/502761* (2013.01); *C12Q 1/6869* (2013.01); *G01N 27/3276* (2013.01); *G01N 33/543* (2013.01); *G01R 33/093* (2013.01); *G01R 33/1276* (2013.01); *C12Q 2563/143* (2013.01); *C12Q 2565/607* (2013.01)

(58) Field of Classification Search
CPC ............... C12Q 1/6874; C12Q 1/6869; C12Q 2563/143; C12Q 2565/607; B01L 3/502761; G01N 27/3276; G01N 33/543; G01R 33/093; G01R 33/1276; G01R 33/098; G11C 11/161
See application file for complete search history.

(56) References Cited

U.S. PATENT DOCUMENTS

| | | |
|---|---|---|
| 6,172,218 B1 | 1/2001 | Brenner |
| 6,210,891 B1 | 4/2001 | Nyren et al. |
| 6,258,568 B1 | 7/2001 | Nyren |
| 6,274,320 B1 | 8/2001 | Rothberg et al. |
| 6,306,597 B1 | 10/2001 | Macevicz |
| 6,565,727 B1 | 5/2003 | Shenderov et al. |
| 6,773,566 B2 | 8/2004 | Shenderov et al. |
| 6,911,132 B2 | 6/2005 | Pamula et al. |
| 6,969,488 B2 | 11/2005 | Bridgham et al. |
| 6,977,033 B2 | 12/2005 | Becker et al. |
| 7,001,792 B2 | 2/2006 | Sauer et al. |
| 7,052,244 B2 | 5/2006 | Fouillet et al. |
| 7,057,026 B2 | 6/2006 | Barnes et al. |
| 7,163,612 B2 | 1/2007 | Sterling et al. |
| 7,211,414 B2 | 5/2007 | Hardin et al. |
| 7,315,019 B2 | 1/2008 | Turner et al. |
| 7,328,979 B2 | 2/2008 | Deere et al. |
| 7,329,492 B2 | 2/2008 | Hardin et al. |
| 7,405,281 B2 | 7/2008 | Xu et al. |
| 7,427,673 B2 | 9/2008 | Balasubramanian et al. |
| 7,541,444 B2 | 6/2009 | Milton et al. |

(Continued)

FOREIGN PATENT DOCUMENTS

| | | |
|---|---|---|
| EP | 1544310 | 6/2005 |
| JP | 2014097058 | 5/2014 |

(Continued)

OTHER PUBLICATIONS

Bentley et al., "Accurate whole human genome sequencing using reversible terminator chemistry," Nature, 456, 53-59 (2008).

(Continued)

*Primary Examiner* — Narayan K Bhat
(74) *Attorney, Agent, or Firm* — Sheppard, Mullin, Richter & Hampton LLP; Jaime D. Choi

(57)      ABSTRACT
Some examples herein provide methods for determining a sequence of a nucleic acid template hybridized to a complementary strand. A polymerase coupled to a magnetically-responsive sensor may capture the nucleic acid template hybridized to the complementary strand. The polymerase and the captured nucleic acid template hybridized to the complementary strand may be contacted with a first fluid comprising a nucleotide. The polymerase may incorporate the nucleotide into the complementary strand based on the sequence of the nucleic acid template. The polymerase and the captured nucleic acid template hybridized to the complementary strand, including the incorporated nucleotide, may be contacted with a second fluid comprising a magnetic particle. The incorporated nucleotide may capture the magnetic particle from the second fluid. The captured magnetic particle may cause a change in electrical resistance at the magnetically-responsive sensor. The change in electrical resistance may be used to identify the incorporated nucleotide.

20 Claims, 19 Drawing Sheets

(56) References Cited

U.S. PATENT DOCUMENTS

| | | | |
|---|---|---|---|
| 7,547,380 | B2 | 6/2009 | Velev |
| 7,566,537 | B2 | 7/2009 | Balasubramanian et al. |
| 7,641,779 | B2 | 1/2010 | Becker et al. |
| 7,727,466 | B2 | 6/2010 | Meathrel et al. |
| 7,948,015 | B2 | 5/2011 | Rothberg |
| 7,985,565 | B2 | 7/2011 | Mayer et al. |
| 8,173,080 | B2 | 5/2012 | Lebl et al. |
| 8,241,573 | B2 | 8/2012 | Banerjee et al. |
| 8,252,910 | B2 | 8/2012 | Korlach et al. |
| 8,262,900 | B2 | 9/2012 | Rothberg et al. |
| 8,343,746 | B2 | 1/2013 | Rank |
| 8,349,167 | B2 | 1/2013 | Rothberg et al. |
| 8,460,910 | B2 | 6/2013 | Smith et al. |
| 8,623,628 | B2 | 1/2014 | Ost et al. |
| 8,951,781 | B2 | 2/2015 | Reed et al. |
| 11,512,348 | B2 * | 11/2022 | Mandell ............. G01R 33/1276 |
| 2003/0205632 | A1 | 11/2003 | Kim et al. |
| 2005/0179746 | A1 | 8/2005 | Roux et al. |
| 2005/0244873 | A1 | 11/2005 | Ikeda |
| 2006/0039823 | A1 | 2/2006 | Yamakawa et al. |
| 2006/0164490 | A1 | 7/2006 | Kim et al. |
| 2006/0194331 | A1 | 8/2006 | Pamula et al. |
| 2007/0023292 | A1 | 2/2007 | Kim et al. |
| 2008/0108082 | A1 | 5/2008 | Rank et al. |
| 2008/0124252 | A1 | 5/2008 | Marchand et al. |
| 2008/0153135 | A1 | 6/2008 | Liu |
| 2008/0283414 | A1 | 11/2008 | Monroe et al. |
| 2009/0192044 | A1 | 7/2009 | Fouillet |
| 2009/0208957 | A1 | 8/2009 | Korlach et al. |
| 2009/0283407 | A1 | 11/2009 | Shah et al. |
| 2009/0321262 | A1 | 12/2009 | Adachi et al. |
| 2010/0096266 | A1 | 4/2010 | Kim et al. |
| 2010/0111768 | A1 | 5/2010 | Banerjee |
| 2010/0137143 | A1 | 6/2010 | Rothberg et al. |
| 2010/0194408 | A1 | 8/2010 | Sturmer et al. |
| 2010/0323573 | A1 | 12/2010 | Chu |
| 2011/0048951 | A1 | 3/2011 | Wu |
| 2011/0118132 | A1 | 5/2011 | Winger et al. |
| 2012/0115736 | A1 | 5/2012 | Bjornson |
| 2012/0270305 | A1 | 10/2012 | Reed et al. |
| 2012/0295262 | A1 | 11/2012 | Ronaghi |
| 2013/0079232 | A1 | 3/2013 | Kain et al. |
| 2013/0085073 | A1 | 4/2013 | Meuleman et al. |
| 2013/0260372 | A1 | 10/2013 | Buermann et al. |
| 2013/0281306 | A1 | 10/2013 | Rigatti |
| 2014/0079923 | A1 | 3/2014 | George et al. |
| 2014/0093881 | A1 | 4/2014 | Sugnet |
| 2015/0045234 | A1 | 2/2015 | Stone et al. |
| 2015/0079596 | A1 | 3/2015 | Eltoukhy et al. |

FOREIGN PATENT DOCUMENTS

| | | |
|---|---|---|
| KR | 10-2010-0114238 | 10/2010 |
| RU | 2539038 | 1/2005 |
| WO | 1991006678 | 5/1991 |
| WO | 2004018497 | 3/2004 |
| WO | 2005065814 | 7/2005 |
| WO | 2006064199 | 6/2006 |
| WO | 2007010251 | 1/2007 |
| WO | 2007120241 | 10/2007 |
| WO | 2007123744 | 11/2007 |
| WO | 2008042067 | 4/2008 |
| WO | 2008098236 | 8/2008 |
| WO | 2009021173 | 2/2009 |
| WO | 2010027894 | 3/2010 |
| WO | 2011002957 | 1/2011 |
| WO | 2013117595 | 8/2013 |
| WO | 2013131962 | 9/2013 |
| WO | 2014143010 | 9/2014 |
| WO | 2015031849 | 3/2015 |
| WO | 2015089092 | 6/2015 |
| WO | 2015089238 | 6/2015 |

OTHER PUBLICATIONS

Christou et al., "Single-molecule magnets," Mrs. Bulletin, 25(11), 66- 71 (2000).

Cockroft et al., "A single-molecule nanopore device detects DNA polymerase activity with single-nucleotide resolution," J. Am. Chem. Soc, 130(3), 818-820 (2008).

Deamer et al., "Characterization of nucleic acids by nanopore analysis," ACC Chem Res, 35(10), 817-825 (2002).

Deamer et al., "Nanopores and nucleic acids: prospects for ultrarapid sequencing," Trends Biotechnol, 18(4), 147-151 (2000).

Dhindsa et al., "Virtual Electrowetting Channels: Electronic Liquid Transport with Continuous Channel Functionality," Lab on a Chip, 10, 832-836 (2010).

Feng et al., "Tristability in a Light-Actuated Single-Molecule Magnet," Journal of the American Chemical Society. 135(42), 15880-15884 (2013).

Fuller et al., "The challenges of sequencing by synthesis," Nat. Biotech. 27(11) 1013-1023 (2009).

Hall et al, "GMR Biosensor Arrays: A System Perspective," Biosens. Bioelectron. 25, 2051-2057, published May 15, 2010.

Healy, K., "Nanopore-based single-molecule DNA analysis," Nanomed. 2(4), 459-481 (2007).

International Search Report and Written Opinion for PCT/US2016/046888 dated Oct. 13, 2016; 14 pages.

Korlach et al., "Selective aluminum passivation for targeted immobilization of single DNA polymerase molecules in zero-mode waveguide nanostructures," PNAS, 105(4), 1176-1181 (2008).

Levene et al., "Zero-Mode Waveguides for Single-Molecule Analysis at high concentrations," Science. 299, 682-686 (2003).

Li et al., "DNA molecules and configurations in a solid-state nanopore microscopy," Nature Mater. 2(9), 611-615 (2003).

Liu, W. et al., "Specific enzyme immobilization approaches and their application with nanomaterials," Topics in Catalysis. 55(16-18), 1146-1156 (2012).

Lundquist et al., "Parallel confocal detection of single molecules in real time," Opt. Lett. 33(9), 1026-1028 (2008).

Mathoniere et al., "Photoinduced single-molecule magnet properties in a four-coordinate iron (II) spin crossover complex," Journal of the American Chemical Society. 135(51), 19083-19086 (2013).

Metzker et al., "Emerging technologies in DNA sequencing," Genome Research. 15, 1767-1776 (2005).

Ronaghi, M., "A Sequencing Method Based on Real-Time Pyrophosphate," Science. 281 (5375), 363-365 (1998).

Ronaghi, M., "Pyrosequencing sheds light on DNA sequencing," Genome Res. 11(1), 3-11 (2001).

Ronaghi, M., "Real-time DNA sequencing using detection of pyrophosphate release," Anal. Biochem. 242 (1), 84-89 (1996).

Ruparel et al., "Design and synthesis of a 3'-O-allyl photocleavable fluorescent nucleotide as a reversible terminator for DNA sequencing by synthesis," PNAS. 102, 5932-5937 (2005).

Sato, O., "Optically switchable molecular solids: photoinduced spin-crossover, photochromism, and photoinduced magnetization," Accounts of chemical research. 36 (9), 692-700 (2003).

Sato, Osamu, "Switchable molecular magnets," Proceedings of the Japan Academy. Series B 88, 213-225 (2012).

Sato et al., "Control of magnetic properties through external stimuli," Angewandte Chemie International Edition. 46 (13), 2152-2187 (2007).

Schmitt-Humbert, C., Authorized Officer, European Patent Office, International Search Report, International Application No. PCT/US2016/046888, Oct. 13, 2016, 4 pages.

Shen et al., "Detection of DNA labeled with magnetic nanoparticles using MgO-based magnetic tunnel junction sensors," Journal of Applied Physics, American Institute of Physics, US. 103(7) 7A306-7A306 (2008).

Smith et al., "High-resolution giant magnetoresistance on-chip arrays for magnetic imaging," Journal of Applied Physics, American Institute of Physics, US. 93(10) 6864-6866 (2003).

Soni et al., "Progress toward Ultrafast DNA Sequencing Using Solid-State Nanopores," Clin Chem. 53(11), 1996-2001 (2007).

Winpenny et al., "Single-molecule magnets and related phenomena," vol. 122 of Structure and bonding Single-molecule magnets and related phenomena, editors Richard Winpenny and Guillem Aromi, Springer (2006).

(56)     References Cited

OTHER PUBLICATIONS

Zakeri et al., "Peptide tag forming a rapid covalent bond to a protein, through engineering a bacterial adhesin," Proc. Nat. Acad. Sci. USA. 109, E690-3697 (2012).

* cited by examiner

A-A

200

205

300

520

610

620

615

Biotin

625

650

660

670

665

655

LINK—X—P—O—P—O—P—O—BASE

OH    OH    OH

O

Z    Y

800

1000

Start

Incorporate nucleotides                                    1010

Detect signals                                             1015

Base calls are made based on magnetic
magnitude using bio-informatics software                  1020

1025

Another
SBS cycle?                    Yes        Deblock/cleave      1030

No

End

1100

1200

1300

Start

Incorporate nucleotides    1310

Detect polymerase SMM signal    1315

Base calls are made based on nucleotide incorporation rate using bio-informatics software    1320

1325   Another SBS cycle?    Yes

No

End

SYSTEMS AND METHODS USING MAGNETICALLY-RESPONSIVE SENSORS FOR DETERMINING A GENETIC CHARACTERISTIC

CROSS-REFERENCE TO RELATED APPLICATIONS CROSS REFERENCE TO

The present application is a continuation under 35 U.S.C. § 120 of U.S. patent application Ser. No. 15/752,192, filed on Feb. 12, 2018 and entitled "Systems and Methods Using Magnetically-Responsive Sensors for Determining a Genetic Characteristic," which is a 35 U.S.C. § 371 national stage application of International Patent Application No. PCT/US2016/046888, filed on Aug. 12, 2016 and entitled "Systems and Methods Using Magnetically-Responsive Sensors for Determining a Genetic Characteristic," which claims the benefit of U.S. Provisional Application No. 62/205,336, filed on Aug. 14, 2015 and entitled the same, the entire contents of each of which is incorporated by reference herein.

BACKGROUND

Current next generation sequencing (NGS) systems based upon sequencing-by-synthesis (SBS) are complex, expensive, and bulky. Therefore, new detection approaches are desirable for SBS instruments.

BRIEF DESCRIPTION

In an embodiment, a sequencing-by-synthesis (SBS) method is provided that includes providing a detection apparatus that includes an array of magnetically-responsive sensors. Each of the magnetically-responsive sensors is located proximate to a respective designated space to detect a magnetic property therefrom. The detection apparatus also includes a plurality of nucleic acid template strands located within corresponding designated spaces. The method also includes conducting a plurality of SBS events to grow a complementary strand by incorporating nucleotides along each template strand. At least some of the nucleotides are attached to corresponding magnetic particles having respective magnetic properties. Each of the plurality of SBS events includes detecting changes in electrical resistance at the magnetically-responsive sensors caused by the respective magnetic properties of the magnetic particles. The method also includes determining genetic characteristics of the complementary strands based on the detected changes in electrical resistance.

In an embodiment, a SBS method is provided that includes providing a detection apparatus that includes an array of magnetically-responsive sensors. Each of the magnetically-responsive sensors is located proximate to a respective designated space to detect a magnetic property therefrom. The detection apparatus also includes a plurality of nucleic acid template strands located within corresponding designated spaces. The method also includes providing a plurality of reactants to the designated spaces. The reactants include nucleotides and polymerase, wherein at least one of the nucleotides or the polymerase have magnetic particles attached thereto. The method also includes detecting changes in electrical resistance at the magnetically-responsive sensors during a plurality of SBS events, wherein each SBS event includes growing a complementary strand by incorporating one of the nucleotides into the complementary strand. The changes in electrical resistance occur when the magnetic particles are positioned within the corresponding designated spaces during the plurality of SBS events. The method also includes determining genetic characteristics of the complementary strands based on the detected changes in electrical resistance.

In an embodiment, a SBS method is provided that includes providing a detection apparatus that includes an array of magnetically-responsive sensors. Each of the magnetically-responsive sensors is located proximate to a respective designated space to detect a magnetic property therefrom. The detection apparatus also includes a plurality of nucleic acid template strands located within corresponding designated spaces. The method also includes conducting a plurality of SBS cycles to grow a complementary strand along each template strand. Each SBS cycle includes (a) delivering nucleotides to the designated spaces and permitting the nucleotides to be added to the complementary strands; (b) delivering magnetic particles to the designated spaces, the magnetic particles being captured by the nucleotides; (c) detecting changes in electrical resistance at the magnetically-responsive sensors, the changes being caused by the magnetic properties of the magnetic particles; and (d) removing the magnetic particles from the designated spaces. The method also includes determining genetic characteristics of the complementary strands based on the detected changes in electrical resistance.

In an embodiment, a SBS method is provided that includes providing a detection apparatus that includes an array of magnetically-responsive sensors. Each of the magnetically-responsive sensors is located proximate to a respective designated space to detect a magnetic property therefrom. The detection apparatus also includes a plurality of nucleic acid template strands located within corresponding designated spaces. The method also includes conducting a plurality of SBS cycles to grow a complementary strand along each template strand. Each SBS cycle includes (a) delivering nucleotides to the designated spaces and permitting the nucleotides to be added to the complementary strands. The nucleotides include at least first, second, and third nucleotides. The first, second, and third nucleotides have different bases. Each SBS cycle also includes (b) delivering magnetic particles to the designated spaces, wherein the magnetic particles are captured by the first nucleotides and by the second nucleotides, and (c) detecting changes in electrical resistance at the magnetically-responsive sensors. Each SBS cycle also includes (d) removing the magnetic particles from the first nucleotides; (e) delivering magnetic particles to the designated spaces, wherein the magnetic particles are captured by the third nucleotides; and (f) detecting changes in electrical resistance at the magnetically-responsive sensors. The method also includes determining genetic characteristics of the complementary strands based on the detected changes in electrical resistance.

In an embodiment, a SBS method is provided that includes providing a detection apparatus that includes an array of magnetically-responsive sensors. Each of the magnetically-responsive sensors is located proximate to a respective designated space to detect a magnetic property therefrom. The detection apparatus also includes a plurality of nucleic acid template strands located within corresponding designated spaces. The method also includes conducting a plurality of SBS cycles to grow a complementary strand along each template strand. Each SBS cycle includes (a) delivering at least first and second nucleotides to the designated spaces to extend the complementary strands. The first and second nucleotides have different bases, wherein the first and second nucleotides have magnetic particles attached thereto. Each SBS cycle also includes (b) detecting changes in electrical resistance at the magnetically-responsive sensors, wherein the magnetic particles captured by the first nucleotides cause a different change in electrical resistance than the magnetic particles captured by the second nucleotides. The method also includes determining genetic characteristics of the complementary strands based on the detected changes in electrical resistance.

In an embodiment, a SBS method is provided. The method includes providing a detection apparatus that includes an array of magnetically-responsive sensors. Each of the magnetically-responsive sensors is located proximate to a respective designated space to detect a magnetic property therefrom. The detection apparatus also includes a plurality of nucleic acid template strands located within corresponding designated spaces. The method also includes conducting a plurality of SBS cycles to grow a complementary strand along each template strand. Each SBS cycle includes (a) delivering at least first and second nucleotides to the designated spaces to extend the complementary strands. The first and second nucleotides have different bases, wherein the first and second nucleotides have first and second single-molecule magnets (SMMs), respectively, attached thereto. Each of the first and second SMMs has different magnetic states that are responsive to different light frequencies. Each SBS cycle also includes (b) altering the magnetic state of the first SMMs by applying a first light frequency and (c) detecting changes in electrical resistance at the magnetically-responsive sensors, wherein the changes are caused by the magnetic state of the first SMMs. Each SBS cycle includes (d) altering the magnetic state of the first SMMs by applying a second light frequency; (e) altering the magnetic state of the second SMMs by applying a third light frequency; and (f) detecting changes in electrical resistance at the magnetically-responsive sensors, wherein the changes are caused by the magnetic state of the second SMMs. The method also includes determining genetic characteristics of the complementary strands based on the detected changes in electrical resistance.

In an embodiment, a SBS method is provided. The method includes providing a detection apparatus that includes an array of magnetically-responsive sensors. Each of the magnetically-responsive sensors is located proximate to a respective designated space to detect a magnetic property therefrom. The detection apparatus also includes a plurality of nucleic acid template strands located within corresponding designated spaces. The method also includes conducting a plurality of SBS cycles to grow a complementary strand along each template strand. Each SBS cycle includes (a) delivering at least first and second nucleotides to the designated spaces to extend the complementary strands. The first and second nucleotides have different bases, wherein the first and second nucleotides have single-molecule magnets (SMMs) attached thereto. The first and second nucleotides have a different number of SMMs attached thereto. The SMMs have magnetic states that are responsive to different light frequencies. Each SBS cycle also includes (b) altering the magnetic state of the SMMs by applying a first light frequency; (c) detecting changes in electrical resistance at the magnetically-responsive sensors; and (d) altering the magnetic state of the SMMs by applying a second light frequency. The method also includes determining genetic characteristics of the complementary strands based on the detected changes in electrical resistance.

In an embodiment, a SBS method is provided. The method includes providing a detection apparatus that includes an array of magnetically-responsive sensors. Each of the magnetically-responsive sensors is located proximate to a respective designated space to detect a magnetic property therefrom. The detection apparatus also includes a plurality of nucleic acid template strands located within corresponding designated spaces. The method also includes conducting a plurality of SBS events to grow a complementary strand by adding nucleotides along each template strand using polymerase. The polymerase have corresponding magnetic particles attached thereto that exhibit respective magnetic properties, wherein each SBS event includes detecting changes in electrical resistance at the magnetically-responsive sensors. The detected changes are caused by the presence of the magnetic particles at the designated spaces when the polymerase adds the nucleotides. The method also includes determining genetic characteristics of the complementary strands based on the detected changes in electrical resistance.

In an embodiment, a SBS method is provided. The method includes providing a detection apparatus that includes an array of magnetically-responsive sensors. Each of the magnetically-responsive sensors is located proximate to a respective designated space to detect a magnetic property therefrom. The detection apparatus also includes a plurality of nucleic acid template strands located within corresponding designated spaces. The method also includes conducting a plurality of SBS cycles to grow a complementary strand along each template strand. Each of the plurality of SBS cycles includes (a) delivering a first nucleotide and polymerase to the designated spaces. The polymerase have magnetic particles attached thereto. Each SBS cycle also includes (b) detecting changes in electrical resistance at the magnetically-responsive sensors. The changes in electrical resistance are caused by the presence of the magnetic particles at the designated spaces when the polymerase adds the first nucleotide to the complementary strand. Each SBS cycle includes (c) delivering a second nucleotide and polymerase to the designated spaces. The polymerase has magnetic particles attached thereto. Each SBS cycle also includes (d) detecting changes in electrical resistance at the magnetically-responsive sensors. The changes in electrical resistance are caused by the presence of the magnetic particles at the designated spaces when the corresponding polymerase adds the second nucleotide to the complementary strand. The method also includes determining genetic characteristics of the complementary strands based on the detected changes in electrical resistance.

In an embodiment, a SBS method is provided. The method includes providing a detection apparatus that includes an array of magnetically-responsive sensors. Each of the magnetically-responsive sensors is located proximate to a respective designated space to detect a magnetic property therefrom. The detection apparatus also includes a plurality of nucleic acid template strands located within corresponding designated spaces. The method also includes conducting a plurality of SBS events to grow a complementary strand along each template strand. Each of the plurality of SBS events includes (a) delivering at least first and second nucleotides and polymerase to the designated spaces. The first and second nucleotides have different bases. The polymerase have magnetic particles attached thereto. Each SBS event also includes (b) detecting changes in electrical resistance at the magnetically-responsive sensors. The changes in electrical resistance are caused by the presence of the magnetic particles at the designated spaces when the polymerase adds the first nucleotide or the second nucleotide to the complementary strand. The first and second nucleotides have different incorporation rates. The method also includes determining genetic characteristics of the complementary strands based on the detected changes in electrical resistance.

In an embodiment, a SBS system is provided that includes a detection apparatus having an array of magnetically-responsive sensors. Each of the magnetically-responsive sensors includes at least two ferromagnetic layers and a non-magnetic layer that separates the two ferromagnetic layers. Each of the magnetically-responsive sensors forms at least one of a giant magnetoresistance (GMR) sensor or a tunnel magnetoresistance (TMR) sensor. The magnetically-responsive sensors are positioned adjacent to corresponding designated spaces within a chamber and configured to detect magnetic particles from the corresponding designated spaces. The system also includes a readout circuit that is communicatively coupled to the magnetically-responsive sensors. The readout circuit is configured to transmit signals that correspond to electrical resistances of the magnetically-responsive sensors. The detection apparatus also includes a fluidic-control system that is configured to flow reagents through the chamber for conducting an SBS protocol. The reagents include a plurality of types of nucleotides, wherein the readout circuit is configured to transmit the signals after each incorporation event.

In an embodiment, a detection apparatus having an array of magnetically-responsive sensors. Each of the magnetically-responsive sensors includes at least two ferromagnetic layers and a non-magnetic layer that separates the two ferromagnetic layers. Each of the magnetically-responsive sensors forms at least one of a giant magnetoresistance (GMR) sensor or a tunnel magnetoresistance (TMR) sensor. The magnetically-responsive sensors are positioned adjacent to corresponding designated spaces within a chamber and configured to detect magnetic particles from the corresponding designated spaces. The detection apparatus may include a readout circuit that is communicatively coupled to the magnetically-responsive sensors.

In an embodiment, a SBS system includes a read head including an arm and a magnetically-responsive sensor attached to the arm. The magnetically-responsive sensor includes at least one of a giant magnetoresistance (GMR) sensor or a tunnel magnetoresistance (TMR) sensor. The magnetically-responsive sensor is configured to detect magnetic particles. The system also includes a sample substrate having a substrate surface. The substrate surface is configured to have a plurality of nucleic acid template strands located within designated spaces along the substrate surface, wherein at least one of the read head and the sample substrate is configured to move with respect to the other to position the magnetically-responsive sensor proximate to the designated spaces in an operative relationship. The system also includes a readout circuit that is communicatively coupled to the magnetically-responsive sensor. The readout circuit is configured to transmit signals that correspond to an electrical resistance of the magnetically-responsive sensor when positioned at one of the designated spaces.

In an embodiment, a SBS method is provided that includes providing a read head having an arm and a magnetically-responsive sensor attached to the arm. The magnetically-responsive sensor includes at least one of a giant magnetoresistance (GMR) sensor or a tunnel magnetoresistance (TMR) sensor. The magnetically-responsive sensor is configured to detect magnetic particles. The method includes providing a sample substrate having a plurality of template strands located at designated spaces along a substrate surface. The method also includes conducting a plurality of SBS cycles to grow complementary strands by incorporating nucleotides along each of the template strands. At least some of the nucleotides are labeled with corresponding magnetic particles that exhibit respective magnetic properties. For each of the SBS cycles, the method includes positioning the magnetically-responsive sensor adjacent to the designated spaces along the substrate surface and detecting an electrical resistance at the magnetically-responsive sensors. The method also includes determining genetic characteristics of the complementary strands based on the detected changes in electrical resistance.

In an embodiment, a SBS method is provided that includes providing a detection apparatus that has an array of magnetically-responsive sensors. Each of the magnetically-responsive sensors is located proximate to a respective designated area to detect a magnetic property therefrom. The detection apparatus also includes polymerase immobilized to the designated areas. The polymerase configured to capture a corresponding template strand. The method also includes conducting a plurality of SBS events to grow a complementary strand by incorporating nucleotides along a corresponding template strand. The nucleotides are attached to corresponding magnetic particles having respective magnetic properties. Each of the plurality of SBS events includes detecting changes in electrical resistance at the magnetically-responsive sensors caused by the respective magnetic properties of the magnetic particles as the nucleotides are added to the complementary strand. The method also includes determining genetic characteristics of the complementary strands based on the detected changes in electrical resistance.

In an embodiment, a SBS method is provided that includes providing a detection apparatus that has an array of magnetically-responsive sensors. Each of the magnetically-responsive sensors is located proximate to a respective designated area to detect a magnetic property therefrom. The detection apparatus also includes polymerase immobilized to the designated areas. The polymerase is configured to attach to corresponding template strands. The method also includes conducting a plurality of SBS events to grow complementary strands along the template strands. Each SBS event includes (a) delivering nucleotides to the designated areas and permitting the nucleotides to be added to the complementary strands. Each SBS event also includes (b) delivering magnetic particles to the designated areas. The magnetic particles are captured by the nucleotides. The magnetic particles provide a corresponding external magnetic field. Each SBS event also includes (c) detecting changes in electrical resistance at the magnetically-responsive sensors and (d) removing the magnetic particles from the designated areas. The method also includes determining genetic characteristics of the complementary strands based on the detected changes in electrical resistance.

In an embodiment, a SBS method is provided that includes providing a detection apparatus that has an array of magnetically-responsive sensors. Each of the magnetically-responsive sensors is located proximate to a respective designated area to detect a magnetic property therefrom. The detection apparatus also includes polymerase immobilized to the designated areas. The polymerase configured to attach to corresponding template strands. The method also includes conducting a plurality of SBS events to grow complementary strands along the template strands. Each SBS event includes (a) delivering nucleotides to the designated areas and permitting the nucleotides to be added to the complementary strands. The nucleotides include at least first, second, and third nucleotides. The first, second, and third nucleotides have different bases. Each SBS event also includes (b) delivering magnetic particles to the designated areas, the magnetic particles being captured by the first nucleotides and by the second nucleotides. Each SBS event also includes (c) detecting changes in electrical resistance at the magnetically-responsive sensors; (d) removing the magnetic particles from the first nucleotides; (e) delivering magnetic particles to the designated areas, the magnetic particles being of the third nucleotides; and (f) detecting changes in electrical resistance at the magnetically-responsive sensors. The method also includes determining genetic characteristics of the complementary strands based on the detected changes in electrical resistance.

In an embodiment a sequencing-by-synthesis (SBS) method is disclosed. The method includes providing a detection apparatus that includes an array of magnetically-responsive sensors, each of the magnetically-responsive sensors being located proximate to a respective designated space to detect a magnetic property therefrom, the detection apparatus also including a plurality of nucleic acid template strands located within corresponding designated spaces. The method also includes conducting a plurality of SBS events to grow a complementary strand by incorporating nucleotides along each template strand, at least some of the nucleotides being attached to corresponding magnetic particles having respective magnetic properties, where each of the plurality of SBS events includes detecting changes in electrical resistance at the magnetically-responsive sensors caused by the respective magnetic properties of the magnetic particles. The method also includes determining genetic characteristics of the complementary strands based on the detected changes in electrical resistance.

In an embodiment, the magnetically-responsive sensors include a magnetoresistive sensor.

In an embodiment, the magnetically-responsive sensors include giant magnetoresistance (GMR) sensors, the changes in electrical resistance being caused by changes in the flow of current through conducting layers of the GMR sensors.

In an embodiment, the magnetically-responsive sensors include tunnel magnetoresistance (TMR) sensors, the changes in electrical resistance being caused by changes in a tunneling electron current through insulative layers of the TMR sensors.

In an embodiment, each of the magnetically-responsive sensors includes first and second ferromagnetic layers and a nonmagnetic layer that separates the first and second ferromagnetic layer.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors for each of the plurality of SBS events.

In an embodiment, determining the sequences of the complementary strands includes determining whether changes in electrical resistance occurred at the magnetically-responsive sensors.

In an embodiment, determining the sequences of the complementary strands includes determining magnitudes of changes in electrical resistance at the magnetically-response sensors.

In an embodiment, the nucleotides include multiple types of nucleotides, each type of nucleotide having a different number of magnetic particles attached thereto than other types of nucleotides.

In an embodiment, the magnetic particles are single-molecule magnets (SMMs).

In an embodiment, the nucleotides include multiple types of nucleotides, each type of nucleotide having a different type of magnetic particle attached thereto than other types of nucleotides.

In an embodiment, the magnetic particles have different magnetic field strengths.

In an embodiment, the magnetic particles include materials that exhibit paramagnetism, diamagnetism, ferromagnetism, or antiferromagnetism.

In an embodiment, the detected changes in electrical resistance at the magnetically-responsive sensors are caused by the intrinsic spins of the electrons in the material of the magnetic particles.

In an embodiment, conducting a plurality of SBS cycles includes conducting a plurality of SBS cycles, each of the plurality of SBS cycles includes delivering multiple types of nucleotides, each type of nucleotide being delivered at a separate time.

In an embodiment, conducting a plurality of SBS cycles includes conducting a plurality of SBS cycles, each of the plurality of SBS cycles includes delivering multiple types of nucleotides simultaneously.

In an embodiment, conducting a plurality of SBS cycles includes conducting a plurality of SBS cycles, each of the plurality of SBS cycles includes delivering the magnetic particles to the corresponding nucleotides after the corresponding nucleotides have been added to the complementary strand.

In an embodiment, the magnetic particles have a reversible linkage.

In an embodiment, the reversible linkage includes biotin, desthiobiotin, avidin, neutravidin, streptavidin, aldehyde, hydrazide, a complementary oligonucleotide, or nucleic acid analog.

In an embodiment, the magnetic particles have a non-reversible linkage.

In an embodiment, the magnetic particles have photo-cleavable linkages.

In an embodiment, the magnetic particles have photo-reversible linkages.

In an embodiment, the magnetic particles have photoactivatable linkages.

In an embodiment, the magnetic particles have a cleavable linkage.

In an embodiment, magnetic particles are configured to bind temporarily to the corresponding nucleotide.

In an embodiment, one or more of the magnetic particles are linked to the gamma phosphate of the nucleotide, the magnetic particle being released when the polymerase adds the nucleotide to the complementary strand.

In an embodiment, each designated space includes a cluster of the template strands that are immobilized to a substrate surface of the detection apparatus.

In an embodiment, each designated space includes a single template strand that is immobilized to a substrate surface of the detection apparatus In an embodiment, the nucleotides have biotin labels.

In an embodiment, the magnetic particles are streptavidin-coated magnetic nanoparticles, the nucleotides and the magnetic particles forming a biotin/streptavidin magnetic nanoparticle (BSMN) complex.

In an embodiment, the detection apparatus includes a flow cell that defines a chamber having the designated spaces, the nucleotides and the magnetic particles being delivered to the designated spaces by flowing the nucleotides and the magnetic particles through the chamber of the flow cell.

In an embodiment, the detection apparatus defines a chamber that includes the designated spaces, the detection apparatus having electrodes that are positioned along the chamber, where delivering the nucleotides and delivering the magnetic particles includes executing droplet operations using the electrodes.

In an embodiment, the plurality of SBS events are carried out through single pot reactions.

In an embodiment, the magnetic particles permanently change the magnetizations of the corresponding magnetically-responsive sensors such that the magnetizations of the corresponding magnetically-responsive sensors are maintained after the magnetic particles are removed, where the method includes changing the magnetization of at least some of the magnetically-responsive sensors after reading the magnetically-responsive sensors.

In an embodiment, the reading the magnetically-responsive sensors occurs after the magnetic particles have been removed.

In an embodiment, a sequencing-by-synthesis (SBS) method is disclosed. The method includes providing a detection apparatus that includes an array of magnetically-responsive sensors, each of the magnetically-responsive sensors being located proximate to a respective designated space to detect a magnetic property therefrom, the detection apparatus also including a plurality of nucleic acid template strands located within corresponding designated spaces. The method includes providing a plurality of reactants to the designated spaces, the reactants including nucleotides and polymerase, where at least one of the nucleotides or the polymerase have magnetic particles attached thereto. The method includes detecting changes in electrical resistance at the magnetically-responsive sensors during a plurality of SBS events, where each SBS event includes growing a complementary strand by incorporating one of the nucleotides into the complementary strand, the changes in electrical resistance occurring when the magnetic particles are positioned within the corresponding designated spaces during the plurality of SBS events. The method includes determining genetic characteristics of the complementary strands based on the detected changes in electrical resistance.

In an embodiment, the magnetically-responsive sensors includes a magnetoresistive sensor.

In an embodiment, the magnetically-responsive sensors include giant magnetoresistance (GMR) sensors, the changes in electrical resistance being caused by changes in the flow of current through conducting layers of the GMR sensors.

In an embodiment, the magnetically-responsive sensors include tunnel magnetoresistance (TMR) sensors, the changes in electrical resistance being caused by changes in a tunneling electron current through insulative layers of the TMR sensors.

In an embodiment, each of the magnetically-responsive sensors includes first and second ferromagnetic layers and a nonmagnetic layer that separates the first and second ferromagnetic layer.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors for each of the plurality of SBS events.

In an embodiment, the nucleotides include multiple types of nucleotides, each type of nucleotide having a different number of magnetic particles attached thereto than other types of nucleotides.

In an embodiment, the magnetic particles are single-molecule magnets (SMMs).

In an embodiment, the nucleotides include multiple types of nucleotides, each type of nucleotide having a different type of magnetic particle attached thereto than other types of nucleotides.

In an embodiment, the magnetic particles have different magnetic field strengths.

In an embodiment, the magnetic properties include at least one of a magnetic field, a magnetic direction, or a magnetic moment.

In an embodiment, the magnetic particles include materials that exhibit paramagnetism, diamagnetism, ferromagnetism, or antiferromagnetism.

In an embodiment, the detected changes in electrical resistance at the magnetically-responsive sensors are caused by the intrinsic spins of the electrons in the material of the magnetic particles.

In an embodiment, each designated space includes a cluster of the template strands that are immobilized to a substrate surface of the detection apparatus.

In an embodiment, each designated space includes a single template strand that is immobilized to a substrate surface of the detection apparatus.

In an embodiment, each designated space includes a single polymerase molecule immobilized to a substrate surface of the detection apparatus.

In an embodiment, the detection apparatus includes a flow cell that defines a chamber having the designated spaces, the reactants being delivered to the designated spaces by simultaneously flowing the reactants through the chamber of the flow cell.

In an embodiment, the detection apparatus defines a chamber that includes the designated spaces, the detection apparatus having electrodes that are positioned along the chamber, wherein delivering the reactants includes executing droplet operations using the electrodes.

In an embodiment, each nucleotide has one or more of the magnetic particles linked to the gamma phosphate of the nucleotide, the magnetic particle being released when the polymerase adds the nucleotide to the complementary strand.

In an embodiment, the magnetic particles are attached to the polymerase, the detected changes being caused by the presence of the magnetic particles at the designated spaces when the polymerase adds the nucleotides.

In an embodiment, each type of nucleotide has a respective incorporation rate that differs from the incorporation rate of other types of nucleotides.

In an embodiment, a sequencing-by-synthesis (SBS) method is disclosed. The method includes providing a detection apparatus that includes an array of magnetically-responsive sensors, each of the magnetically-responsive sensors being located proximate to a respective designated space to detect a magnetic property therefrom, the detection apparatus also including a plurality of nucleic acid template strands located within corresponding designated spaces. The method includes conducting a plurality of SBS cycles to grow a complementary strand along each template strand. Each SBS cycle includes (a) delivering nucleotides to the designated spaces and permitting the nucleotides to be added to the complementary strands. Each SBS cycle includes (b) delivering magnetic particles to the designated spaces, the magnetic particles being captured by the nucleotides. Each SBS cycle includes (c) detecting changes in electrical resistance at the magnetically-responsive sensors, the changes being caused by the magnetic properties of the magnetic particles. Each SBS cycle includes (d) removing the magnetic particles from the designated spaces. The method includes determining genetic characteristics of the complementary strands based on the detected changes in electrical resistance.

In an embodiment, the (a)-(d) are repeated for multiple types of nucleotides, each type of nucleotide being delivered separately to the designated spaces.

In an embodiment, the delivering the nucleotides includes simultaneously delivering multiple types of nucleotides and delivering the magnetic particles includes simultaneously delivering multiple types of the magnetic particles, each type of magnetic particles having a corresponding magnetic field strength that is different from the magnetic field strengths of other types of magnetic particles.

In an embodiment, each designated space includes a cluster of the template strands that are immobilized to a substrate surface of the detection apparatus.

In an embodiment, each designated space includes a single template strand that is immobilized to a substrate surface of the detection apparatus.

In an embodiment, the nucleotides have biotin labels.

In an embodiment, the magnetic particles are streptavidin-coated magnetic nanoparticles, the nucleotides and the magnetic particles forming a biotin/streptavidin magnetic nanoparticle (BSMN) complex, the method further comprising removing the BSMN complex.

In an embodiment, the magnetic particles are functionalized magnetic nanoparticles.

In an embodiment, the magnetic particles are streptavidin-coated magnetic nanoparticles.

In an embodiment, the designated spaces are located within a chamber of a flow cell and wherein delivering the nucleotides and delivering the magnetic particles includes flowing the nucleotides and flowing the magnetic particles, respectively, through the chamber.

In an embodiment, the detection apparatus defines a chamber that includes the designated spaces, the detection apparatus having electrodes that are positioned along the chamber, wherein delivering the nucleotides and delivering the magnetic particles includes executing droplet operations using the electrodes.

In an embodiment, each of the plurality of SBS cycles further comprises detecting a background level of electrical resistance after (d).

In an embodiment, the nucleotides include blocking groups, the method further comprising removing the blocking groups after (c).

In an embodiment, the magnetically-responsive sensors include a magnetoresistive sensor.

In an embodiment, the magnetically-responsive sensors include giant magnetoresistance (GMR) sensors, the changes in electrical resistance being caused by changes in the flow of current through conducting layers of the GMR sensors.

In an embodiment, the magnetically-responsive sensors include tunnel magnetoresistance (TMR) sensors, the changes in electrical resistance being caused by changes in a tunneling electron current through insulative layers of the TMR sensors.

In an embodiment, each of the magnetically-responsive sensors includes first and second ferromagnetic layers and a nonmagnetic layer that separates the first and second ferromagnetic layer.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors for each of the plurality of SBS cycles.

In an embodiment, the magnetic properties include at least one of a magnetic field, a magnetic direction, or a magnetic moment.

In an embodiment, the magnetic particles include materials that exhibit paramagnetism, diamagnetism, ferromagnetism, or antiferromagnetism.

In an embodiment, the detected changes in electrical resistance at the magnetically-responsive sensors are caused by the intrinsic spins of the electrons in the material of the magnetic particles.

In an embodiment, the magnetic particles permanently change the magnetizations of the corresponding magnetically-responsive sensors such that the magnetizations of the corresponding magnetically-responsive sensors are maintained after the magnetic particles are removed, wherein the SBS cycles include changing the magnetization of at least some of the magnetically-responsive sensors after reading the magnetically-responsive sensors.

In an embodiment, reading the magnetically-responsive sensors occurs after the magnetic particles have been removed.

In an embodiment, sequencing-by-synthesis (SBS) method is disclosed. The method includes providing a detection apparatus that includes an array of magnetically-responsive sensors, each of the magnetically-responsive sensors being located proximate to a respective designated space to detect a magnetic property therefrom, the detection apparatus also including a plurality of nucleic acid template strands located within corresponding designated spaces. The method includes conducting a plurality of SBS cycles to grow a complementary strand along each template strand. Each SBS cycle includes (a) delivering nucleotides to the designated spaces and permitting the nucleotides to be added to the complementary strands, the nucleotides including at least first, second, and third nucleotides, the first, second, and third nucleotides having different bases. Each SBS cycle includes (b) delivering magnetic particles to the designated spaces, the magnetic particles being captured by the first nucleotides and by the second nucleotides. Each SBS cycle includes (c) detecting changes in electrical resistance at the magnetically-responsive sensors. Each SBS cycle includes (d) removing the magnetic particles from the first nucleotides. Each SBS cycle includes (e) delivering magnetic particles to the designated spaces, the magnetic particles being captured by the third nucleotides. Each SBS cycle includes (f) detecting changes in electrical resistance at the magnetically-responsive sensors. The method includes determining genetic characteristics of the complementary strands based on the detected changes in electrical resistance.

In an embodiment, the first nucleotide extended the complementary strand at (a) if a change in electrical resistance was detected at (c) but not detected at (f); the second nucleotide extended the complementary strand at (a) if a change in electrical resistance was detected at (c) and detected at (f); and the third nucleotide extended the complementary strand at (a) if a change in electrical resistance was not detected at (c) but was detected at (f).

In an embodiment, (a) includes delivering fourth nucleotides and wherein the fourth nucleotide extended the complementary strand at (a) if a change in electrical resistance was not detected at (c) and was not detected at (f).

In an embodiment, each of the plurality of SBS cycles further comprises: (g) removing the magnetic particles from the second and third nucleotides.

In an embodiment, (d) and (e) occur concurrently.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors for each of the plurality of SBS cycles.

In an embodiment, the magnetic properties include at least one of a magnetic field, a magnetic direction, or a magnetic moment.

In an embodiment, the magnetic particles include materials that exhibit paramagnetism, diamagnetism, ferromagnetism, or antiferromagnetism.

In an embodiment, the detected changes in electrical resistance at the magnetically-responsive sensors are caused by the intrinsic spins of the electrons in the material of the magnetic particles.

In an embodiment, the nucleotides include blocking groups, the method further comprising removing the blocking groups after (c).

In an embodiment, the magnetic particles permanently change the magnetizations of the corresponding magnetically-responsive sensors such that the magnetizations of the corresponding magnetically-responsive sensors are maintained after the magnetic particles are removed after (f), wherein the SBS cycles include changing the magnetization of at least some of the magnetically-responsive sensors after reading the magnetically-responsive sensors.

In an embodiment, the reading the magnetically-responsive sensors occurs after the magnetic particles have been removed.

In an embodiment, a sequencing-by-synthesis (SBS) method is disclosed. The method includes providing a detection apparatus that includes an array of magnetically-responsive sensors, each of the magnetically-responsive sensors being located proximate to a respective designated space to detect a magnetic property therefrom, the detection apparatus also including a plurality of nucleic acid template strands located within corresponding designated spaces. The method includes conducting a plurality of SBS cycles to grow a complementary strand along each template strand. Each SBS cycle includes (a) delivering at least first and second nucleotides to the designated spaces to extend the complementary strands, the first and second nucleotides having different bases, wherein the first and second nucleotides have magnetic particles attached thereto. Each SBS cycle includes (b) detecting changes in electrical resistance at the magnetically-responsive sensors, where the magnetic particles captured by the first nucleotides cause a different change in electrical resistance than the magnetic particles captured by the second nucleotides. The method includes determining genetic characteristics of the complementary strands based on the detected changes in electrical resistance.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors for each of the plurality of SBS cycles.

In an embodiment, determining the sequences of the complementary strands includes determining whether the detected changes at the magnetically-responsive sensors are approximately equal to a first magnitude or approximately equal to a second magnitude.

In an embodiment, determining the sequences of the complementary strands includes determining whether the detected changes at the magnetically-responsive sensors exceed a threshold.

In an embodiment, determining the sequences of the complementary strands includes determining whether the detected changes at the magnetically-responsive sensors are within a designated range of values.

In an embodiment, determining the sequences of the complementary strands includes comparing the detected changes at each magnetically-responsive sensor through multiple SBS cycles.

In an embodiment, determining the sequences of the complementary strands includes comparing, for each SBS cycle, the detected changes associated with a plurality of the magnetically-responsive sensors.

In an embodiment, the first and second nucleotides capture a different number of the magnetic particles, the different number of the magnetic particles configured to cause different magnitudes of changes in electrical resistance.

In an embodiment, the magnetic particles are single-molecule magnets (SMMs).

In an embodiment, the first nucleotides capture a first type of magnetic particles and the second nucleotides capture a second type of magnetic particles, the first and second types of magnetic particles configured to cause different magnitudes of changes in electrical resistance.

In an embodiment, the first and second types of magnetic particles have different paramagnetic materials.

In an embodiment, delivering the first and second nucleotides at (a) includes delivering the first and second nucleotides to the designated spaces to extend the complementary strands and subsequently delivering the magnetic particles to the designated spaces, whereby the magnetic particles attach to the first and second nucleotides.

In an embodiment, the nucleotides include blocking groups, the method further comprising removing the blocking groups after each SBS event.

In an embodiment, each of the first and second nucleotides has one or more of the magnetic particles linked to the gamma phosphate of the nucleotide, the magnetic particle being released when the polymerase adds the first nucleotide or the second nucleotide to the complementary strand.

In an embodiment, a sequencing-by-synthesis (SBS) method is disclosed. The method includes providing a detection apparatus that includes an array of magnetically-responsive sensors, each of the magnetically-responsive sensors being located proximate to a respective designated space to detect a magnetic property therefrom, the detection apparatus also including a plurality of nucleic acid template strands located within corresponding designated spaces. The method includes conducting a plurality of SBS cycles to grow a complementary strand along each template strand. Each SBS cycle includes (a) delivering at least first and second nucleotides to the designated spaces to extend the complementary strands, the first and second nucleotides having different bases, wherein the first and second nucleotides have first and second single-molecule magnets (SMMs), respectively, attached thereto, each of the first and second SMMs having different magnetic states that are responsive to different light frequencies. Each SBS cycle includes (b) altering the magnetic state of the first SMMs by applying a first light frequency. Each SBS cycle includes (c) detecting changes in electrical resistance at the magnetically-responsive sensors, wherein the changes are caused by the magnetic state of the first SMMs. Each SBS cycle includes (d) altering the magnetic state of the first SMMs by applying a second light frequency. Each SBS cycle includes (e) altering the magnetic state of the second SMMs by applying a third light frequency. Each SBS cycle includes (t) detecting changes in electrical resistance at the magnetically-responsive sensors, wherein the changes are caused by the magnetic state of the second SMMs. The method includes determining genetic characteristics of the complementary strands based on the detected changes in electrical resistance.

In an embodiment, each of the SBS cycles further comprises altering the magnetic state of the second SMMs by applying a fourth light frequency.

In an embodiment, the SMMs comprise metal-organic compounds that exhibit superparamagnetic behavior.

In an embodiment, at least one of (b)-(d) or (e)-(f) are repeated multiple times for at least some of the SBS cycles.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors for each of the plurality of SBS events.

In an embodiment, determining the sequences of the complementary strands includes determining whether the detected changes at the magnetically-responsive sensors are approximately equal to a first magnitude or approximately equal to a second magnitude.

In an embodiment, determining the sequences of the complementary strands includes determining whether the detected changes at the magnetically-responsive sensors exceed a threshold.

In an embodiment, determining the sequences of the complementary strands includes determining whether the detected changes at the magnetically-responsive sensors are within a designated range of values.

In an embodiment, determining the sequences of the complementary strands includes comparing the detected changes at each magnetically-responsive sensor through multiple SBS cycles.

In an embodiment, determining the sequences of the complementary strands includes comparing, for each SBS cycle, the detected changes associated with a plurality of the magnetically-responsive sensors.

In an embodiment, the nucleotides include blocking groups, the method further comprising removing the blocking groups after each SBS event.

In an embodiment, each of the first and second nucleotides has one or more of the magnetic particles linked to the gamma phosphate of the nucleotide, the magnetic particle being released when the polymerase adds the first nucleotide or the second nucleotide to the complementary strand.

In an embodiment, a sequencing-by-synthesis (SBS) method is disclosed. The method includes providing a detection apparatus that includes an array of magnetically-responsive sensors, each of the magnetically-responsive sensors being located proximate to a respective designated space to detect a magnetic property therefrom, the detection apparatus also including a plurality of nucleic acid template strands located within corresponding designated spaces. The method includes conducting a plurality of SBS cycles to grow a complementary strand along each template strand. Each SBS cycle includes (a) delivering at least first and second nucleotides to the designated spaces to extend the complementary strands, the first and second nucleotides having different bases, where the first and second nucleotides have single-molecule magnets (SMMs) attached thereto, the first and second nucleotides having a different number of SMMs attached thereto, the SMMs having magnetic states that are responsive to different light frequencies. Each SBS cycle includes (b) altering the magnetic state of the SMMs by applying a first light frequency. Each SBS cycle includes (c) detecting changes in electrical resistance at the magnetically-responsive sensors. Each SBS cycle includes (d) altering the magnetic state of the SMMs by applying a second light frequency. The method includes determining genetic characteristics of the complementary strands based on the detected changes in electrical resistance.

In an embodiment, the SMMs comprise metal-organic compounds that exhibit superparamagnetic behavior.

In an embodiment, (b)-(d) is repeated multiple times for at least some of the SBS cycles.

In an embodiment, the at least first and second nucleotides includes first, second, and third nucleotides that each have SMMs attached thereto, the first, second, and third nucleotides having a different number of SMMs attached thereto.

In an embodiment, the SMMs comprise metal-organic compounds that exhibit superparamagnetic behavior.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors for each of the plurality of SBS cycles.

In an embodiment, determining the sequences of the complementary strands includes determining whether the magnitudes of the detected changes are approximately equal to a first magnitude or approximately equal to a second magnitude.

In an embodiment, determining the sequences of the complementary strands includes determining whether the magnitudes of the detected changes at the magnetically-responsive sensors exceed a threshold.

In an embodiment, determining the sequences of the complementary strands includes determining whether the magnitudes of the detected changes at the magnetically-responsive sensors are within a designated range of values.

In an embodiment, determining the sequences of the complementary strands includes comparing the magnitudes of the detected changes at each magnetically-responsive sensor through multiple SBS cycles.

In an embodiment, determining the sequences of the complementary strands includes comparing, for each SBS cycle, the magnitudes of the detected changes associated with a plurality of the magnetically-responsive sensors.

In an embodiment, the nucleotides include blocking groups, the method further comprising removing the blocking groups at the end of each cycle.

In an embodiment, each of the first and second nucleotides has one or more of the magnetic particles linked to the gamma phosphate of the nucleotide, the magnetic particle being released when the polymerase adds the first nucleotide or the second nucleotide to the complementary strand.

In an embodiment, a sequencing-by-synthesis (SBS) method is disclosed. The method includes providing a detection apparatus that includes an array of magnetically-responsive sensors, each of the magnetically-responsive sensors being located proximate to a respective designated space to detect a magnetic property therefrom, the detection apparatus also including a plurality of nucleic acid template strands located within corresponding designated spaces. The method includes conducting a plurality of SBS events to grow a complementary strand by adding nucleotides along each template strand using polymerase, the polymerase having corresponding magnetic particles attached thereto that exhibit respective magnetic properties, wherein each SBS event includes detecting changes in electrical resistance at the magnetically-responsive sensors, the detected changes being caused by the presence of the magnetic particles at the designated spaces when the polymerase adds the nucleotides. The method includes determining genetic characteristics of the complementary strands based on the detected changes in electrical resistance.

In an embodiment, the magnetic particles are single-molecule magnets (SMMs), the method further comprising altering the magnetic state of the SMMs using one or more light frequencies.

In an embodiment, conducting the plurality of SBS events includes: (a) delivering a first type of nucleotides to the designated spaces and detecting changes in the electrical resistance associated with the first type of nucleotides and (b) delivering a second type of nucleotides to the designated spaces and detecting changes in the electrical resistance associated with the second type of nucleotides.

In an embodiment, conducting the plurality of SBS events includes simultaneously delivering multiple types of nucleotides to the designated spaces and detecting changes in the electrical resistance, wherein each type of nucleotide has a respective incorporation rate that differs from the incorporation rate of other types of nucleotides, wherein sequences of the complementary strands are based on durations of the detected changes.

In an embodiment, determining the sequences of the complementary strands includes determining whether the durations of the detected changes are approximately equal to one of a number of values, the number of values being equal to the number of types of nucleotides.

In an embodiment, determining the sequences of the complementary strands includes determining whether the durations of the detected changes are within a number of possible ranges values, the number of possible range values being equal to the number of types of nucleotides.

In an embodiment, determining the sequences of the complementary strands includes comparing the durations of the detected changes at each magnetically-responsive sensor through multiple SBS events.

In an embodiment, determining the sequences of the complementary strands includes comparing, for each SBS event, the durations of the detected changes associated with a plurality of the magnetically-responsive sensors.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors for each of the plurality of SBS events.

In an embodiment, conducting the plurality of SBS events includes simultaneously providing a plurality of reactants to the designated spaces, the reactants including nucleotides and the polymerase, wherein the SBS events are conducted through single pot reactions.

In an embodiment, sequencing-by-synthesis (SBS) method is disclosed. The method includes providing a detection apparatus that includes an array of magnetically-responsive sensors, each of the magnetically-responsive sensors being located proximate to a respective designated space to detect a magnetic property therefrom, the detection apparatus also including a plurality of nucleic acid template strands located within corresponding designated spaces. The method includes conducting a plurality of SBS cycles to grow a complementary strand along each template strand. Each of the plurality of SBS cycles includes (a) delivering a first nucleotide and polymerase to the designated spaces, the polymerase having magnetic particles attached thereto. Each of the plurality of SBS cycles includes (b) detecting changes in electrical resistance at the magnetically-responsive sensors, the changes in electrical resistance being caused by the presence of the magnetic particles at the designated spaces when the polymerase adds the first nucleotide to the complementary strand. Each of the plurality of SBS cycles includes (c) delivering a second nucleotide and polymerase to the designated spaces, the polymerase having magnetic particles attached thereto. Each of the SBS cycles includes (d) detecting changes in electrical resistance at the magnetically-responsive sensors, the changes in electrical resistance being caused by the presence of the magnetic particles at the designated spaces when the corresponding polymerase adds the second nucleotide to the complementary strand. The method includes determining genetic characteristics of the complementary strands based on the detected changes in electrical resistance.

In an embodiment, the magnetic particles are single-molecule magnets (SMMs), the method further comprising altering the magnetic state of the SMMs using one or more light frequencies.

In an embodiment, each of the plurality of SBS cycles further include (e) delivering a third nucleotide to the designated spaces and polymerase, the polymerase having magnetic particles attached thereto; and (f) detecting changes in electrical resistance at the magnetically-responsive sensors, the changes in electrical resistance being caused by the presence of the magnetic particles at the designated spaces when the polymerase adds the third nucleotide to the complementary strand.

In an embodiment, each of the plurality of SBS cycles further include delivering a fourth nucleotide to the designated spaces and polymerase.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors.

In an embodiment, the nucleotides include blocking groups, the method further comprising removing the blocking groups at the end of each cycle.

An in an embodiment, a sequencing-by-synthesis (SBS) method is disclosed. The method includes providing a detection apparatus that includes an array of magnetically-responsive sensors, each of the magnetically-responsive sensors being located proximate to a respective designated space to detect a magnetic property therefrom, the detection apparatus also including a plurality of nucleic acid template strands located within corresponding designated spaces. The method includes conducting a plurality of SBS events to grow a complementary strand along each template strand. Each of the plurality of SBS events include (a) delivering at least first and second nucleotides and polymerase to the designated spaces, the first and second nucleotides having different bases, the polymerase having magnetic particles attached thereto. Each of the plurality of SBS events include (b) detecting changes in electrical resistance at the magnetically-responsive sensors, the changes in electrical resistance being caused by the presence of the magnetic particles at the designated spaces when the polymerase adds the first nucleotide or the second nucleotide to the complementary strand, where the first and second nucleotides have different incorporation rates. The method includes determining genetic characteristics of the complementary strands based on the detected changes in electrical resistance.

In an embodiment, the magnetic particles are single-molecule magnets (SMMs).

In an embodiment, delivering at least first and second nucleotides includes delivering first, second, and third nucleotides that each have a different base and a different incorporation rate.

In an embodiment, delivering at least first and second nucleotides includes delivering first, second, third, and fourth nucleotides that each have a different base and a different incorporation rate.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors.

In an embodiment, the nucleotides include blocking groups, the method further comprising removing the blocking groups at the end of each cycle.

In an embodiment, conducting the plurality of SBS events includes simultaneously providing a plurality of reactants to the designated spaces, the reactants including the first and second nucleotides and the polymerase, wherein the SBS events are conducted through single pot reactions.

In an embodiment, a sequencing-by-synthesis (SBS) system is disclosed. The system includes a detection apparatus including an array of magnetically-responsive sensors, each of the magnetically-responsive sensors including at least two ferromagnetic layers and a non-magnetic layer that separates the two ferromagnetic layers, each of the magnetically-responsive sensors forming at least one of a giant magnetoresistance (GMR) sensor or a tunnel magnetoresistance (TMR) sensor, the magnetically-responsive sensors being positioned adjacent to corresponding designated spaces within a chamber and configured to detect magnetic particles from the corresponding designated spaces. The system includes a readout circuit communicatively coupled to the magnetically-responsive sensors, wherein the readout circuit is configured to transmit signals that correspond to electrical resistances of the magnetically-responsive sensors. The system includes a fluidic-control system is configured to flow reagents through the chamber for conducting an SBS protocol, the reagents including a plurality of types of nucleotides, wherein the readout circuit is configured to transmit the signals after each incorporation event.

In an embodiment, the magnetically-responsive sensors include GMR sensors configured to change between first and second states, wherein the two ferromagnetic layers are antiferromagnetically coupled in the first state such that the nonmagnetic layer has a first electrical resistance, and wherein an external magnetic field impedes the antiferrogmagnetic coupling in the second state such that the nonmagnetic layer has a second electrical resistance.

In an embodiment, the magnetically-responsive sensors include TMR sensors configured to change between first and second states, wherein the two ferromagnetic layers have opposite directions of magnetization in the first state such that the nonmagnetic layer has a first electrical resistance, and wherein the two ferromagnetic layers have the same direction of magnetization in the second state such that the nonmagnetic layer has a first electrical resistance.

In an embodiment, the fluidic-control system is configured to (a) flow nucleotides to the designated spaces to add the nucleotides to complementary strands; and (b) flow magnetic particles to the designated spaces, the magnetic particles attaching to the nucleotides, the magnetic particles exhibiting a corresponding detectable magnetic property; and (d) remove the magnetic particles from the designated spaces; and where the readout circuit is configured to detect the electrical resistance at the magnetically-responsive sensors after (b).

In an embodiment, the fluidic-control system is configured to: (a) deliver nucleotides to the designated spaces to add the nucleotides to the complementary strands, the nucleotides including at least first, second, and third nucleotides, the first, second, and third nucleotides having different bases; (b) deliver magnetic particles to the designated spaces, the magnetic particles attaching to the first nucleotides and by the second nucleotides; (c) remove the magnetic particles from the first nucleotides; (d) deliver magnetic particles to the designated spaces, the magnetic particles attaching to the third nucleotides; where the readout circuit is configured to detect the electrical resistance at the magnetically-responsive sensors after (b) and after (d).

In an embodiment, the fluidic-control system is configured to deliver at least first and second nucleotides to the designated spaces to extend the complementary strands, the first and second nucleotides having different bases, wherein the first and second nucleotides have magnetic particles attached thereto, wherein the readout circuit is configured to detect changes in electrical resistance at the magnetically-responsive sensors, the magnetic particles of the first nucleotides causing a different change in electrical resistance than the magnetic particles of the second nucleotides.

In an embodiment, a sequencing-by-synthesis (SBS) system is disclosed. The system includes a read head including an arm and a magnetically-responsive sensor attached to the arm, the magnetically-responsive sensor including at least one of a giant magnetoresistance (GMR) sensor or a tunnel magnetoresistance (TMR) sensor, the magnetically-responsive sensor being configured to detect magnetic particles. The system includes a sample substrate having a substrate surface, the substrate surface configured to have a plurality of nucleic acid template strands located within designated spaces along the substrate surface, wherein at least one of the read head and the sample substrate is configured to move with respect to the other to position the magnetically-responsive sensor proximate to the designated spaces in an operative relationship. The system includes a readout circuit communicatively coupled to the magnetically-responsive sensor, wherein the readout circuit is configured to transmit signals that correspond to an electrical resistance of the magnetically-responsive sensor when positioned at one of the designated spaces.

In an embodiment, the sample substrate is rotatable about an axis.

In an embodiment, the sample substrate is disc-shaped.

In an embodiment, the read head includes a plurality of magnetically-responsive sensors attached to the arm, wherein the readout circuit is configured to transmit signals from at least a plurality of the magnetically-responsive sensors for at least some of the operative relationship.

In an embodiment, a sequencing-by-synthesis (SBS) method is disclosed. The method includes providing a read head including an arm and a magnetically-responsive sensor attached to the arm, the magnetically-responsive sensor including at least one of a giant magnetoresistance (GMR) sensor or a tunnel magnetoresistance (TMR) sensor, the magnetically-responsive sensor being configured to detect magnetic particles. The method includes providing a sample substrate having a plurality of template strands located at designated spaces along a substrate surface. The method includes conducting a plurality of SBS cycles to grow complementary strands by incorporating nucleotides along each of the template strands, at least some of the nucleotides being labeled with corresponding magnetic particles that exhibit respective magnetic properties; where, for each of the SBS cycles, the method includes positioning the magnetically-responsive sensor adjacent to the designated spaces along the substrate surface and detecting an electrical resistance at the magnetically-responsive sensors. The method includes determining genetic characteristics of the complementary strands based on the detected changes in electrical resistance.

In an embodiment, the sample substrate is rotatable about an axis and wherein positioning the magnetically-responsive sensor includes rotating the sample substrate about the axis.

In an embodiment, the sample substrate is disc-shaped.

In an embodiment, the read head includes a plurality of magnetically-responsive sensors attached to the arm.

In an embodiment, a sequencing-by-synthesis (SBS) method is disclosed. The method includes providing a detection apparatus that includes an array of magnetically-responsive sensors, each of the magnetically-responsive sensors being located proximate to a respective designated area to detect a magnetic property therefrom, the detection apparatus also including polymerase immobilized to the designated areas, the polymerase configured to capture a corresponding template strand. The method includes conducting a plurality of SBS events to grow a complementary strand by incorporating nucleotides along a corresponding template strand, the nucleotides being attached to corresponding magnetic particles having respective magnetic properties, where each of the plurality of SBS events includes detecting changes in electrical resistance at the magnetically-responsive sensors caused by the respective magnetic properties of the magnetic particles as the nucleotides are added to the complementary strand. The method includes determining genetic characteristics of the complementary strands based on the detected changes in electrical resistance.

In an embodiment, the magnetically-responsive sensors includes a magnetoresistive sensor.

In an embodiment, the magnetically-responsive sensors include giant magnetoresistance (GMR) sensors, the changes in electrical resistance being caused by changes in the flow of current through conducting layers of the GMR sensors.

In an embodiment, the magnetically-responsive sensors include tunnel magnetoresistance (TMR) sensors, the changes in electrical resistance being caused by changes in a tunneling electron current through insulative layers of the TMR sensors.

In an embodiment, each of the magnetically-responsive sensors includes first and second ferromagnetic layers and a nonmagnetic layer that separates the first and second ferromagnetic layer.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors for each of the plurality of SBS events.

In an embodiment, determining the sequences of the complementary strands includes determining whether changes in electrical resistance occurred at the magnetically-responsive sensors.

In an embodiment, determining the sequences of the complementary strands includes determining magnitudes of changes in electrical resistance at the magnetically-response sensors.

In an embodiment, the nucleotides include multiple types of nucleotides, each type of nucleotide having a different number of magnetic particles attached thereto than other types of nucleotides.

In an embodiment, the magnetic particles are single-molecule magnets (SMMs).

In an embodiment, the nucleotides include multiple types of nucleotides, each type of nucleotide having a different type of magnetic particle attached thereto than other types of nucleotides.

In an embodiment, the magnetic particles have different magnetic field strengths.

In an embodiment, the magnetic properties include at least one of a magnetic field, a magnetic direction, or a magnetic moment.

In an embodiment, the magnetic particles include materials that exhibit paramagnetism, diamagnetism, ferromagnetism, or antiferromagnetism.

In an embodiment, the detected changes in electrical resistance at the magnetically-responsive sensors are caused by the intrinsic spins of the electrons in the material of the magnetic particles.

In an embodiment, each of the plurality of SBS events includes delivering multiple types of nucleotides, each type of nucleotide being delivered at a separate time.

In an embodiment, each of the plurality of SBS events includes delivering multiple types of nucleotides simultaneously.

In an embodiment, each of the plurality of SBS events includes delivering the magnetic particles to the corresponding nucleotides after the corresponding nucleotides have been added to the complementary strand.

In an embodiment, the magnetic particles have a reversible linkage.

In an embodiment, each designated area includes a single template strand that is captured by the polymerase.

In an embodiment, the detection apparatus includes a flow cell that defines a chamber having the designated areas, the nucleotides and the magnetic particles being delivered to the designated areas by flowing the nucleotides and the magnetic particles through the chamber of the flow cell.

In an embodiment, the detection apparatus defines a chamber that includes the designated areas, the detection apparatus having electrodes that are positioned along the chamber, wherein delivering the nucleotides and delivering the magnetic particles includes executing droplet operations using the electrodes.

In an embodiment, a sequencing-by-synthesis (SBS) method is disclosed. The method includes providing a detection apparatus that includes an array of magnetically-responsive sensors, each of the magnetically-responsive sensors being located proximate to a respective designated area to detect a magnetic property therefrom, the detection apparatus also including polymerase immobilized to the designated areas, the polymerase configured to attach to corresponding template strands. The method includes conducting a plurality of SBS events to grow complementary strands along the template strands. Each SBS event includes (a) delivering nucleotides to the designated areas and permitting the nucleotides to be added to the complementary strands. Each SBS event includes (b) delivering magnetic particles to the designated areas, the magnetic particles being captured by the nucleotides, the magnetic particles providing a corresponding external magnetic field. Each SBS event includes (c) detecting changes in electrical resistance at the magnetically-responsive sensors. Each SBS event includes (d) removing the magnetic particles from the designated areas. The method includes determining genetic characteristics of the complementary strands based on the detected changes in electrical resistance.

In an embodiment, (a)-(d) are repeated for multiple types of nucleotides, each type of nucleotide being delivered separately to the designated areas.

In an embodiment, delivering the nucleotides includes simultaneously delivering multiple types of nucleotides and delivering the magnetic particles includes simultaneously delivering multiple types of the magnetic particles, each type of magnetic particles having a corresponding magnetic field property that is different from the magnetic field properties of other types of magnetic particles.

In an embodiment, each designated area includes a single template strand that is immobilized to a substrate surface of the detection apparatus.

In an embodiment, the designated areas are located within a chamber of a flow cell and wherein delivering the nucleotides and delivering the magnetic particles includes flowing the nucleotides and flowing the magnetic particles, respectively, through the chamber.

In an embodiment, the detection apparatus defines a chamber that includes the designated areas, the detection apparatus having electrodes that are positioned along the chamber, wherein delivering the nucleotides and delivering the magnetic particles includes executing droplet operations using the electrodes.

In an embodiment, each of the plurality of SBS events further comprises detecting a background level of electrical resistance after (d).

In an embodiment, the nucleotides include blocking groups, the method further comprising removing the blocking groups after each of the SBS events.

In an embodiment, a sequencing-by-synthesis (SBS) method is disclosed. The method includes providing a detection apparatus that includes an array of magnetically-responsive sensors, each of the magnetically-responsive sensors being located proximate to a respective designated area to detect a magnetic property therefrom, the detection apparatus also including polymerase immobilized to the designated areas, the polymerase configured to attach to corresponding template strands. The method includes conducting a plurality of SBS events to grow complementary strands along the template strands. Each SBS event includes (a) delivering nucleotides to the designated areas and permitting the nucleotides to be added to the complementary strands, the nucleotides including at least first, second, and third nucleotides, the first, second, and third nucleotides having different bases. Each SBS event includes (b) delivering magnetic particles to the designated areas, the magnetic particles being captured by the first nucleotides and by the second nucleotides. Each SBS event includes (c) detecting changes in electrical resistance at the magnetically-responsive sensors. Each SBS event includes (d) removing the magnetic particles from the first nucleotides. Each SBS event includes (e) delivering magnetic particles to the designated areas, the magnetic particles being of the third nucleotides. Each SBS event includes (f) detecting changes in electrical resistance at the magnetically-responsive sensors. The method includes determining genetic characteristics of the complementary strands based on the detected changes in electrical resistance.

In an embodiment, the first nucleotide extended the complementary strand at (a) if a change in electrical resistance was detected at (c) but not detected at (f); the second nucleotide extended the complementary strand at (a) if a change in electrical resistance was detected at (c) and detected at (t); and the third nucleotide extended the complementary strand at (a) if a change in electrical resistance was not detected at (c) but was detected at (f).

In an embodiment, (a) includes delivering fourth nucleotides and wherein the fourth nucleotide extended the complementary strand at (a) if a change in electrical resistance was not detected at (c) and was not detected at (f).

In an embodiment, each of the plurality of SBS events further comprises: (g) removing the magnetic particles from the second and third nucleotides.

In an embodiment, (d) and (e) occur concurrently.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors for each of the plurality of SBS events.

In an embodiment, the magnetic properties include at least one of a magnetic field, a magnetic direction, or a magnetic moment.

In an embodiment, the magnetic particles include materials that exhibit paramagnetism, diamagnetism, ferromagnetism, or antiferromagnetism.

In an embodiment, the detected changes in electrical resistance at the magnetically-responsive sensors are caused by the intrinsic spins of the electrons in the material of the magnetic particles.

In an embodiment, the nucleotides include blocking groups, the method further comprising removing the blocking groups after each SBS event.

In an embodiment, a sequencing-by-synthesis (SBS) method is disclosed. The method includes providing a detection apparatus that includes an array of magnetically-responsive sensors, each of the magnetically-responsive sensors being located proximate to a respective designated area to detect a magnetic property therefrom, the detection apparatus also including polymerase immobilized to the designated areas, the polymerase configured to attach to corresponding template strands. The method includes conducting a plurality of SBS events to grow complementary strands along the template strands. Each SBS event includes (a) delivering at least first and second nucleotides to the designated areas to extend the complementary strands, the first and second nucleotides having different bases, wherein the first and second nucleotides have magnetic particles attached thereto. Each SBS event includes (b) detecting changes in electrical resistance at the magnetically-responsive sensors, where the magnetic particles of the first nucleotides cause a different change in electrical resistance than the magnetic particles of the second nucleotides. The method includes determining genetic characteristics of the complementary strands based on the detected changes in electrical resistance.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors for each of the plurality of SBS events.

In an embodiment, determining the sequences of the complementary strands includes determining whether the detected changes at the magnetically-responsive sensors are approximately equal to a first magnitude or approximately equal to a second magnitude.

In an embodiment, determining the sequences of the complementary strands includes determining whether the detected changes at the magnetically-responsive sensors exceed a threshold.

In an embodiment, determining the sequences of the complementary strands includes determining whether the detected changes at the magnetically-responsive sensors are within a designated range of values.

In an embodiment, determining the sequences of the complementary strands includes comparing the detected changes at each magnetically-responsive sensor through multiple SBS events.

In an embodiment, determining the sequences of the complementary strands includes comparing, for each SBS event, the detected changes associated with a plurality of the magnetically-responsive sensors.

In an embodiment, the first and second nucleotides capture a different number of the magnetic particles, the different number of the magnetic particles configured to cause different magnitudes of changes in electrical resistance.

In an embodiment, the magnetic particles are single-molecule magnets (SMMs).

In an embodiment, the first nucleotides capture a first type of magnetic particles and the second nucleotides capture a second type of magnetic particles, the first and second types of magnetic particles configured to cause different magnitudes of changes in electrical resistance.

In an embodiment, the first and second types of magnetic particles have different paramagnetic materials.

In an embodiment, delivering the first and second nucleotides at (a) includes delivering the first and second nucleotides to the designated areas to extend the complementary strands and subsequently delivering the magnetic particles to the designated areas, whereby the magnetic particles attach to the first and second nucleotides.

In an embodiment, the nucleotides include blocking groups, the method further comprising removing the blocking groups after each SBS event.

In an embodiment, a sequencing-by-synthesis (SBS) method is disclosed. The method includes providing a detection apparatus that includes an array of magnetically-responsive sensors, each of the magnetically-responsive sensors being located proximate to a respective designated area to detect a magnetic property therefrom, the detection apparatus also including polymerase immobilized to the designated areas, the polymerase configured to attach to corresponding template strands. The method includes conducting a plurality of SBS events to grow complementary strands along the template strands. Each SBS event includes (a) delivering at least first and second nucleotides to the designated areas to extend the complementary strands, the first and second nucleotides having different bases, where the first and second nucleotides have first and second single-molecule magnets (SMMs), respectively, attached thereto, each of the first and second SMMs having different magnetic states that are responsive to different light frequencies. Each SBS event includes (b) altering the magnetic state of the first SMMs by applying a first light frequency. Each SBS event includes (c) detecting changes in electrical resistance at the magnetically-responsive sensors, where the changes are caused by the magnetic state of the first SMMs. Each SBS event includes (d) altering the magnetic state of the first SMMs by applying a second light frequency. Each SBS event includes (e) altering the magnetic state of the second SMMs by applying a third light frequency. Each SBS event includes (f) detecting changes in electrical resistance at the magnetically-responsive sensors, wherein the changes are caused by the magnetic state of the second SMMs. The method includes determining genetic characteristics of the complementary strands based on the detected changes in electrical resistance.

In an embodiment, each of the SBS events further comprises altering the magnetic state of the second SMMs by applying a fourth light frequency.

In an embodiment, the SMMs comprise metal-organic compounds that exhibit superparamagnetic behavior.

In an embodiment, at least one of (b)-(d) or (e)-(f) are repeated multiple times for at least some of the SBS events.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors for each of the plurality of SBS events.

In an embodiment, determining the sequences of the complementary strands includes determining whether the detected changes at the magnetically-responsive sensors are approximately equal to a first magnitude or approximately equal to a second magnitude.

In an embodiment, determining the sequences of the complementary strands includes determining whether the detected changes at the magnetically-responsive sensors exceed a threshold.

In an embodiment, determining the sequences of the complementary strands includes determining whether the detected changes at the magnetically-responsive sensors are within a designated range of values.

In an embodiment, determining the sequences of the complementary strands includes comparing the detected changes at each magnetically-responsive sensor through multiple SBS events.

In an embodiment, determining the sequences of the complementary strands includes comparing, for each SBS event, the detected changes associated with a plurality of the magnetically-responsive sensors.

In an embodiment, the nucleotides include blocking groups, the method further comprising removing the blocking groups after each SBS event.

In an embodiment, a sequencing-by-synthesis (SBS) method is disclosed. The method includes providing a detection apparatus that includes an array of magnetically-responsive sensors, each of the magnetically-responsive sensors being located proximate to a respective designated area to detect a magnetic property therefrom, the detection apparatus also including polymerase immobilized to the designated areas, the polymerase configured to attach to corresponding template strands. The method includes conducting a plurality of SBS events to grow complementary strands along the template strands. Each SBS event includes (a) delivering at least first and second nucleotides to the designated areas to extend the complementary strands, the first and second nucleotides having different bases, where the first and second nucleotides have single-molecule magnets (SMMs) attached thereto, the first and second nucleotides having a different number of SMMs attached thereto, the SMMs having magnetic states that are responsive to different light frequencies. Each SBS event includes (b) altering the magnetic state of the SMMs by applying a first light frequency. Each SBS event includes (c) detecting changes in electrical resistance at the magnetically-responsive sensors. Each SBS event includes (d) altering the magnetic state of the SMMs by applying a second light frequency. The method includes determining genetic characteristics of the complementary strands based on the detected changes in electrical resistance.

In an embodiment, the SMMs comprise metal-organic compounds that exhibit superparamagnetic behavior.

In an embodiment, (b)-(d) is repeated multiple times for at least some of the SBS events.

In an embodiment, the at least first and second nucleotides includes first, second, and third nucleotides that each have SMMs attached thereto, the first, second, and third nucleotides having a different number of SMMs attached thereto.

In an embodiment, the SMMs comprise metal-organic compounds that exhibit superparamagnetic behavior.

In an embodiment, determining the genetic characteristic of the complementary strands includes analyzing the detected changes in electrical resistance to determine whether signals based on the detected changes form a designated pattern.

In an embodiment, determining the genetic characteristics includes determining sequences of the complementary strands, the sequences of the complementary strands being based on the detected changes in electrical resistance that occurred at the magnetically-responsive sensors for each of the plurality of SBS events.

In an embodiment, determining the sequences of the complementary strands includes determining whether the magnitudes of the detected changes are approximately equal to a first magnitude or approximately equal to a second magnitude.

In an embodiment, determining the sequences of the complementary strands includes determining whether the magnitudes of the detected changes at the magnetically-responsive sensors exceed a threshold.

In an embodiment, determining the sequences of the complementary strands includes determining whether the magnitudes of the detected changes at the magnetically-responsive sensors are within a designated range of values.

In an embodiment, determining the sequences of the complementary strands includes comparing the magnitudes of the detected changes at each magnetically-responsive sensor through multiple SBS events.

In an embodiment, determining the sequences of the complementary strands includes comparing, for each SBS event, the magnitudes of the detected changes associated with a plurality of the magnetically-responsive sensors.

In an embodiment, the nucleotides include blocking groups, the method further comprising removing the blocking groups at the end of each event.

In an embodiment, a sequencing-by-synthesis (SBS) method is disclosed. The method includes providing a detection apparatus that includes an array of magnetically-responsive sensors, each of the magnetically-responsive sensors being located proximate to a respective designated space to detect a magnetic property therefrom, the detection apparatus also including a plurality of nucleic acid template strands located within corresponding designated spaces. The method includes conducting a plurality of SBS cycles to grow a complementary strand along each template strand. Each SBS cycle includes (a) delivering nucleotides to the designated spaces and permitting the nucleotides to be added to the complementary strands, the nucleotides including at least first, second, and third nucleotides, the first, second, and third nucleotides having different bases, where the first and second nucleotides include magnetic particles and the third nucleotides do not include magnetic particles. Each SBS cycle includes (b) detecting changes in electrical resistance at the magnetically-responsive sensors caused by the magnetic particles of the first and second nucleotides. Each SBS cycle includes (c) removing the magnetic particles from the first nucleotides. Each SBS cycle includes (d) delivering magnetic particles to the designated spaces, the magnetic particles being captured by the third nucleotides. Each SBS cycle includes (e) detecting changes in electrical resistance at the magnetically-responsive sensors caused by the magnetic particles of the second and third nucleotides. The method includes determining genetic characteristics of the complementary strands based on the detected changes in electrical resistance.

In an embodiment, the first nucleotide extended the complementary strand at (a) if a change in electrical resistance was detected at (b) but not detected at (e); the second nucleotide extended the complementary strand at (a) if a change in electrical resistance was detected at (b) and detected at (e); and the third nucleotide extended the complementary strand at (a) if a change in electrical resistance was not detected at (b) but was detected at (e).

In an embodiment, (a) includes delivering fourth nucleotides and wherein the fourth nucleotide extended the complementary strand at (a) if a change in electrical resistance was not detected at (b) and was not detected at (e).

DETAILED DESCRIPTION

Figure 1A:
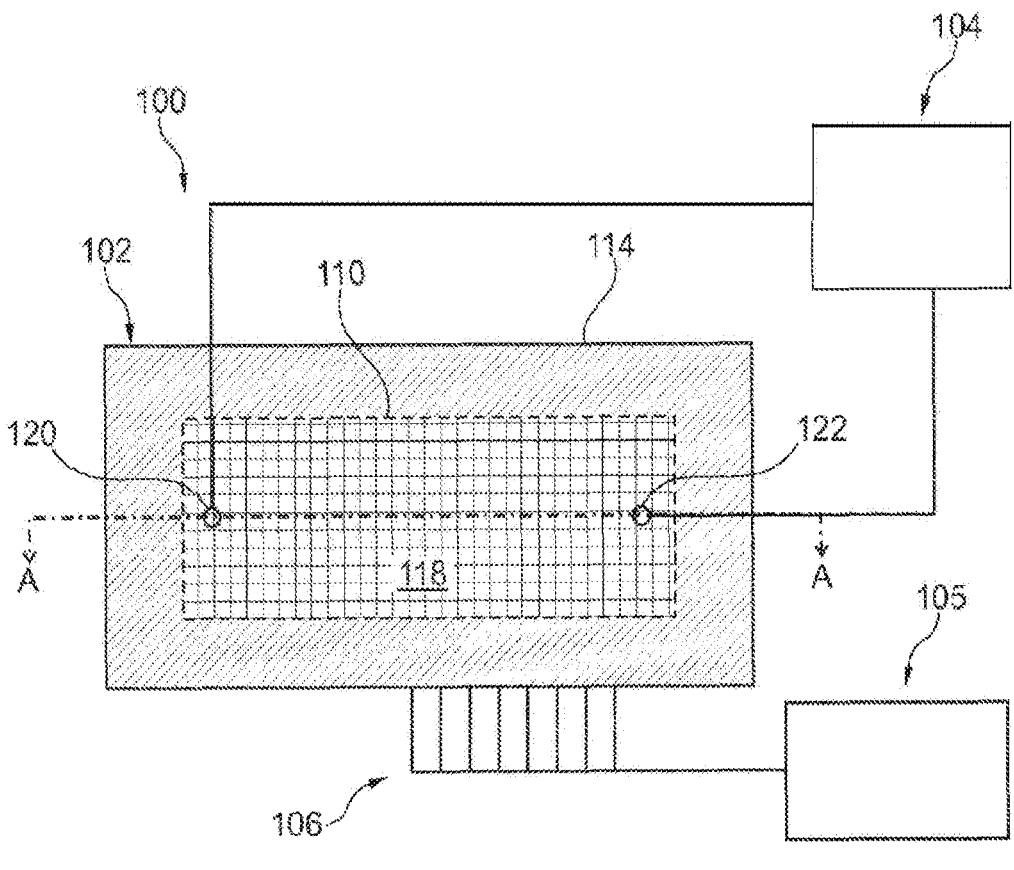
FIG. 1A illustrates a top view of a system that comprises a magnetic sensor array for supporting, for example, a magnetic biosensing SBS scheme.

The methods described herein can be used in conjunction with a variety of biological or chemical analysis techniques, including nucleic acid sequencing techniques. Embodiments may be used to determine a genetic characteristic of a sample based on changes in electrical resistance that occur as a nucleic acid strand is grown. Particularly applicable techniques are those wherein the biological or chemical samples are localized at designated positions such that their relative positions do not change during analysis. For example, nucleic acids may be attached at fixed locations along a substrate surface during a designated protocol in which the array is repeatedly scanned. Embodiments in which impressions are obtained with different channels, for example, coinciding with different labels used to distinguish one nucleotide base type from another, are particularly applicable. In some embodiments, the process to determine the nucleotide sequence of a target nucleic acid can be an automated process Preferred embodiments include sequencing-by-synthesis ("SBS") techniques.

As set forth herein, embodiments may be used to determine a genetic characteristic of a sample. The genetic characteristic may be determined by analyzing changes in electrical resistance that occur at magnetically-responsive sensors. For example, magnetic particles that are associated with nucleotides or polymerase may cause changes in the electrical resistance at the magnetically-responsive sensors as the nucleotides are added to a nucleic acid. Signals from the magnetically-responsive sensors that are based on the electrical resistance provide data that may be analyzed and used to determine a genetic characteristic. As used herein, the term "genetic characteristic" includes a sequence of a nucleic acid or any characteristic that is based on the sequence of the nucleic acid, whether or not the precise sequence is determined. For example, embodiments may grow a complementary strand of nucleic acid in which each nucleotide that is added to the strand is associated with one or more magnetic particles. In some embodiments, the nucleotide may be identified at each incorporation event (e.g., in real-time). In other embodiments, the nucleotide may be identified only after multiple incorporation events or after the sequencing run has finished with secondary analysis.

Yet still in other embodiments, the genetic characteristic may be determined without individually identifying the nucleotides such that the sequence is known. For example, the data provided by the signals after one or more incorporation events may be analyzed to distinguish one sequence from one or more other sequences. As one particular example, data derived from two (or more) nucleic acids that include a single nucleotide polymorphism (SNP) may be compared. Without knowing the sequences of the nucleic acids, embodiments may analyze the patterns of the signals that are received from the magnetically-responsive sensors. For example, each nucleotide may have a magnetic particle with a different magnetic property. The detected changes in electrical resistance from a series of nucleotides may form a pattern. Signals that form a first pattern may have one genotype, and signals that form a second pattern may have a second genotype. Accordingly, nucleic acids that provide the first pattern may be called for having a certain genetic characteristic while nucleic acids that provide the second pattern may be called for having a different genetic characteristic. Again, such determinations may be made without knowing the sequences of the nucleic acids.

It should be understood that "determining a genetic characteristic" does not necessarily include identifying, with specificity, which genetic characteristic that the sample may have. For example, while investigating a certain genotype that is based on a suspected SNP, embodiments may only identify that one or more samples have a certain pattern while other samples do not have that pattern. In either case, a genetic characteristic of the sample has been determined. Likewise, "determining a genetic characteristic" may include determining that a sample does not have a suspected pathogen or determining that a genetic variant does not have a SNP or a short tandem repeat (STR).

As another example, a sample from an individual who is suspected of having a certain condition may undergo testing. The condition may be caused by, for example, a genetic disorder, cancer, or a pathogen (e.g., Ebola). The testing may include detecting changes in electrical resistance as nucleic acids are grown. Again, without knowing the precise sequence of the nucleic acids, embodiments may determine whether the individual has the condition by analyzing the signals to identify one or more patterns.

"Sequencing-by-synthesis ("SBS") techniques" generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using 7-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminescent signals that are produced due to incorporation of nucleotides at the features of the array. An image can be obtained after the array is treated with a particular nucleotide type (e.g., A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in International Patent Pub. No. WO 04/018497 and U.S. Pat. No. 7,057,026, the disclosures of which are incorporated herein by reference. This approach is being commercialized by Solexa (now Illumina Inc.), and is also described in International Patent Pub. No. WO 91/06678 and International Patent Pub. No. WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could be deblocked by a short treatment with a palladium catalyst. The fluorophore was attached to the base via a photocleavable linker that could be cleaved by a 30 second exposure to long wavelength UV light. Either disulfide reduction or photocleavage can be used to cleave linkers, for example. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Pat. Nos. 7,541,444, 7,566,537, 7,057,026, 8,460,910, 8,623,628, International Patent Pub. No. WO 05/065814, U.S. Pat. No. 7,985,565, International Patent Pub. No. WO 06/064199, International Patent Pub. No. WO 07/010,251, U.S. Patent Pub. No. 20120270305 and U.S. Patent Pub. No. 20130260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Pub. No. 20130079232. As a first example, a pair of nucleotide types can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples is a fluorescence-based SBS method that uses a first nucleotide type that is detected in a first channel (e.g., dATP having a label that is detected in the first channel when excited by a first excitation wavelength), a second nucleotide type that is detected in a second channel (e.g., dCTP having a label that is detected in the second channel when excited by a second excitation wavelength), a third nucleotide type that is detected in both the first and the second channel (e.g., dTTP having at least one label that is detected in both channels when excited by the first and/or second excitation wavelength) and a fourth nucleotide type that lacks a label that is not, or minimally, detected in either channel (e.g., dGTP having no label).

Further, as described in the incorporated materials of U.S. Patent Pub. No. 20130079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore, although some nanopore embodiments can utilize methods involving the real-time monitoring of DNA polymerase nucleotide incorporation. The nanopore can be a synthetic pore or biological membrane protein, such as α-hemolysin. In one exemplary embodiment, as the target nucleic acid passes through the nanopore, each base can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. Nos. 7,405,281 and 8,343,746 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

In particular embodiments, the polymerase is immobilized or tethered to a designated area along a surface that is proximate to a magnetically-responsive sensor. Such embodiments may increase the likelihood that the different magnetic particles that are detected by the magnetically-responsive sensor as the complementary strand is grown may have relatively equal distances away from the magnetically-responsive sensor.

Embodiments described herein may also include γ-phosphate-labeled nucleotides in which the label that is coupled to the 7-phosphate includes the magnetic particle that changes the electrical resistance of the magnetically-responsive sensors.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in U.S. Pat. Nos. 8,262, 900; 7,948,015; U.S. Patent Pub. No. 20100137143; or U.S. Pat. No. 8,349,167, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion polymerase chain reaction (PCR) as described in further detail below.

The methods set forth herein can use arrays having features at any of a variety of densities including, for example, at least about 10 features/cm², 100 features/cm², 500 features/cm², 1,000 features/cm², 5,000 features/cm², 10,000 features/cm², 50,000 features/cm², 100,000 features/cm², 1,000,000 features/cm², 5,000,000 features/cm², or, higher.

An advantage of the methods set forth herein is that they provide for rapid and efficient detection of a plurality of target nucleic acids in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Pat. No. 8,241,573 and U.S. Patent Pub. No. 20120270305, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, CA) and devices described in U.S. Patent Pub. No. 20120270305, which is incorporated herein by reference.

As used herein, the following terms have the meanings indicated. "Droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. Droplets may take a wide variety of shapes; non-limiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the present disclosure, see Eckhardt et al., International Patent Pub. No. WO/2007/120241, entitled, "Droplet-Based Biochemistry," published on Oct. 25, 2007, the entire disclosure of which is incorporated herein by reference.

In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. A droplet can include nucleic acids, such as DNA, genomic DNA, RNA, mRNA or analogs thereof; nucleotides such as deoxyribonucleotides, ribonucleotides or analogs thereof such as analogs having terminator moieties such as those described in Bentley et al., Nature 456:53-59 (2008); Gormley et al., International Patent Pub. No. WO/2013/131962, entitled, "Improved Methods of Nucleic Acid Sequencing," published on Sep. 12, 2013; Barnes et al., U.S. Pat. No. 7,057,026, entitled "Labelled Nucleotides," issued on Jun. 6, 2006; Kozlov et al., International Patent Pub. No. WO/2008/042067, entitled, "Compositions and Methods for Nucleotide Sequencing," published on Apr. 10, 2008; Rigatti et al., International Patent Pub. No. WO/2013/117595, entitled, "Targeted Enrichment and Amplification of Nucleic Acids on a Support," published on Aug. 15, 2013; Hardin et al., U.S. Pat. No. 7,329,492, entitled "Methods for Real-Time Single Molecule Sequence Fetermination," issued on Feb. 12, 2008; Hardin et al., U.S. Pat. No. 7,211,414, entitled "Enzymatic Nucleic Acid Synthesis: Compositions and Methods for Altering Monomer Incorporation Fidelity," issued on May 1, 2007; Turner et al., U.S. Pat. No. 7,315, 019, entitled "Arrays of Optical Confinements and Uses Thereof," issued on Jan. 1, 2008; Xu et al., U.S. Pat. No. 7,405,281, entitled "Fluorescent Nucleotide Analogs and Uses Therefor," issued on Jul. 29, 2008; and Rank et al., U.S. Patent Pub. No. 20080108082, entitled "Polymerase Enzymes and Reagents for Enhanced Nucleic Acid Sequencing," published on May 8, 2008, the entire disclosures of which are incorporated herein by reference; enzymes such as polymerases, ligases, recombinases, or transposases, binding partners such as antibodies, epitopes, streptavidin, avidin, biotin, lectins or carbohydrates; or other biochemically active molecules. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. A droplet may include one or more beads.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S. Pat. No. 6,773,566, entitled "Electrostatic Actuators for Microfluidics and Methods for Using Same," issued on Aug. 10, 2004; Shenderov, U.S. Pat. No. 6,565,727, entitled "Actuators for Microfluidics Without Moving Parts," issued on May 20, 2003; Kim et al., U S. Patent Pub. No. 20030205632, entitled "Electrowetting-driven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Microfluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, U S. Patent Pub. No. 20110048951, entitled "Digital Microfluidics Based Apparatus for Heat-exchanging Chemical Processes," published on Mar. 3, 2011; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," Lab Chip, 10:832-836 (2010), the entire disclosures of which are incorporated herein by reference. Certain droplet actuators will include one or more substrates arranged with a droplet operations gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the present disclosure. During droplet operations it is preferred that droplets remain in continuous contact or frequent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, NJ) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define on-actuator dispensing reservoirs. The spacer height may, for example, be at least about 5 µm, 100 µm, 200 µm, 250 µm, 275 µm more. Alternatively or additionally the spacer height may be at most about 600 µm, 400 µm, 350 µm, 300 µm, or less. The spacer may, for example, be formed of a layer of projections form the top or bottom substrates, and/or a material inserted between the top and bottom substrates. One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications. In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the present disclosure include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and opto-electrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the present disclosure. Similarly, one or more of the foregoing may be used to deliver liquid into a droplet operations gap, e.g., from a reservoir in another device or from an external reservoir of the droplet actuator (e.g., a reservoir associated with a droplet actuator substrate and a flow path from the reservoir into the droplet operations gap). Droplet operations surfaces of certain droplet actuators of the present disclosure may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, DE), members of the cytop family of materials, coatings in the FLUOROPEL® family of hydrophobic and superhydrophobic coatings (available from Cytonix Corporation, Beltsville, MD), silane coatings, fluorosilane coatings, hydrophobic phosphonate derivatives (e.g., those sold by Aculon, Inc), and NOVEC™ electronic coatings (available from 3M Company, St. Paul, MN), other fluorinated monomers for plasma-enhanced chemical vapor deposition (PECVD), and organosiloxane (e.g., SiOC) for PECVD. In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene) poly(styrenesulfonate) (PEDOT: PSS). Other examples of electrically conducting organic polymers and alternative conductive layers are described in Pollack et al., International Patent Pub. No. WO/2011/002957, entitled "Droplet Actuator Devices and Methods," published on Jan. 6, 2011, the entire disclosure of which is incorporated herein by reference. One or both substrates may be fabricated using a printed circuit board (PCB), glass, indium tin oxide (ITO)-coated glass, and/or semiconductor materials as the substrate. When the substrate is ITO-coated glass, the ITO coating is preferably a thickness of at least about 20 nm, 50 nm, 75 nm, 100 nm or more. Alternatively or additionally the thickness can be at most about 200 nm, 150 nm, 125 nm or less. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MITSUI™ BN-300 (available from MITSUI Chemicals America, Inc., San Jose CA); ARLON™ 11N (available from Arlon, Inc, Santa Ana, CA); NELCO® N4000-6 and N5000-30/32 (available from Park Electrochemical Corp., Melville, NY); ISOLA™ FR406 (available from Isola Group, Chandler, AZ), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® nonwoven aramid reinforcement (available from DuPont, Wilmington, DE); NOMEX® brand fiber (available from DuPont, Wilmington, DE); and paper. Various materials are also suitable for use as the dielectric component of the substrate. Examples include: vapor deposited dielectric, such as PARYLENE™ C (especially on glass), PARYLENE™ N, and PARYLENE™ HT (for high temperature, ~300° C.) (available from Parylene Coating Services, Inc., Katy, TX); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc.

Carson City, NV) (good thermal characteristics for applications involving thermal control), and PROBIMER™ 8165 (good thermal characteristics for applications involving thermal control (available from Huntsman Advanced Materials Americas Inc., Los Angeles, CA) dry film soldermask, such as those in the VACREL® dry film soldermask line (available from DuPont, Wilmington, DE); film dielectrics, such as polyimide film (e.g., KAPTON® polyimide film, available from DuPont, Wilmington, DE), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; polypropylene; and black flexible circuit materials, such as DuPont™ Pyralux® HXC and DuPont™ Kapton® MBC (available from DuPont, Wilmington, DE). Droplet transport voltage and frequency may be selected for performance with reagents used in specific assay protocols. Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the present disclosure may be derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, other fluorinated monomers for plasma-enhanced chemical vapor deposition (PECVD), and organosiloxane (e.g., SiOC) for PECVD. Additionally, in some cases, some portion or all of the droplet operations surface may be coated with a substance for reducing background noise, such as background fluorescence from a PCB substrate. For example, the noise-reducing coating may include a black matrix resin, such as the black matrix resins available from Toray industries, Inc., Japan. Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the methods and apparatus set forth herein includes those described in Meathrel et al., U.S. Pat. No. 7,727,466, entitled "Disintegratable Films for Diagnostic Devices," issued on Jun. 1, 2010, the entire disclosure of which is incorporated herein by reference.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position, incubating a droplet; beating a droplet; vaporizing a droplet; cooling a droplet; disposing of a droplet; transporting a droplet out of a droplet actuator, other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., U.S. Patent Pub. No. 20100194408, entitled "Capacitance Detection in a Droplet Actuator," published on Aug. 5, 2010, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1×-, 2×-3×-droplets are usefully controlled operated using 1, 2, and 3 electrodes, respectively. If the droplet footprint is greater than number of electrodes available for conducting a droplet operation at a given time, the difference between the droplet size and the number of electrodes should typically not be greater than 1, in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

"Filler fluid" means a fluid associated with a droplet operations substrate of a droplet actuator, which fluid is sufficiently immiscible with a droplet phase to render the droplet phase subject to electrode-mediated droplet operations. For example, the droplet operations gap of a droplet actuator is typically filled with a filler fluid. The filler fluid may, for example, be or include a low-viscosity oil, such as silicone oil or hexadecane filler fluid. The filler fluid may be or include a halogenated oil, such as a fluorinated or perfluorinated oil. The filler fluid may fill the entire gap of the droplet actuator or may coat one or more surfaces of the droplet actuator. Filler fluids may be conductive or non-conductive. Filler fluids may be selected to improve droplet operations and/or reduce loss of reagent or target substances from droplets, improve formation of microdroplets, reduce cross contamination between droplets, reduce contamination of droplet actuator surfaces, reduce degradation of droplet actuator materials, etc. For example, filler fluids may be selected for compatibility with droplet actuator materials. As an example, fluorinated filler fluids may be usefully employed with fluorinated surface coatings. Fluorinated filler fluids are useful to reduce loss of lipophilic compounds, such as umbelliferone substrates like 6-hexade-canoylamido-4-methylumbelliferone substrates (e.g., for use in Krabbe, Niemann-Pick, or other assays); other umbelliferone substrates are described in Winger et al., U.S. Patent Pub. No. 20110118132, entitled "Enzymatic Assays Using Umbelliferone Substrates with Cyclodextrins in Droplets of Oil," published on May 19, 2011, the entire disclosure of which is incorporated herein by reference. Examples of suitable fluorinated oils include those in the Galden line, such as Galden HT170 (bp=170° C., viscosity=1.8 cSt, density=1.77). Galden HT200 (bp=200 C, viscosity=2.4 cSt, d=1.79), Galden HT230 (bp=230 C, viscosity=4.4 cSt, d=1.82) (all from Solvay Solexis); those in the Novec line, such as Novec 7500 (bp=128 C, viscosity=0.8 cSt, d=1.61), Fluorinert FC-40 (bp=155° C., viscosity=1.8 cSt, d=1.85), Fluorinert FC-43 (bp=174° C., viscosity=2.5 cSt, d=1.86) (both from 3M). In general, selection of perfluorinated filler fluids is based on kinematic viscosity (<7 cSt is preferred, but not required), and on boiling point (>150° C. is preferred, but not required, for use in DNA/RNA-based applications (PCR, etc.)). Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler fluid, including surfactant doping, may be selected for performance with reagents used in the specific assay protocols and effective interaction or non-interaction with droplet actuator materials. Examples of filler fluids and filler fluid formulations suitable for use with the methods and apparatus set forth herein are provided in Srinivasan et al, International Patent Pub. No. WO/2010/027894, entitled "Droplet Actuators, Modified Fluids and Methods," published on Jun. 3, 2010; Srinivasan et al, International Patent Pub. No. WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Jan. 15, 2009; and Monroe et al., U.S. Patent Pub. No. 20080283414, entitled "Electrowetting Devices," published on Nov. 20, 2008, the entire disclosures of which are incorporated herein by reference, as well as the other patents and patent applications cited herein. Fluorinated oils may in some cases be doped with fluorinated surfactants, e.g., Zonyl FSO-100 (Sigma-Aldrich) and/or others. A filler fluid is typically a liquid. In some embodiments, a filler gas can be used instead of a liquid.

"Reservoir" means an enclosure or partial enclosure configured for holding, storing, or supplying liquid. A droplet actuator system of the present disclosure may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or flow path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap.

The terms "top," "bottom," "over," "under," and "on" are used throughout the description with reference to the relative positions of components of the flow cell and/or droplet actuator, such as relative positions of top and bottom substrates of the flow cell and/or droplet actuator. It will be appreciated that the flow cell and/or droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface. In one example, filler fluid can be considered as a film between such liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

Embodiments set forth herein may include methods, systems, devices, and apparatuses for biological or chemical analysis using a magnetic sensing scheme. For example, embodiments may use magnetic sensing detection for base detection and discrimination during a sequencing-by-synthesis (SBS) protocol. Various embodiments may provide methods for magnetic biosensing based SBS on an integrated CMOS flow cell and/or droplet actuator. In some embodiments, a flow cell may include one or more channels defined by surfaces that may have template strands immobilized thereto. Different solutions may be directed through the channels, in accordance with a predetermined schedule, to deliver reagents for SBS sequencing. In other embodiments, the reagents may be delivered by droplets that are controlled on a droplet actuator.

In some embodiments, the SBS sequencing may be carried out through a single pot reaction (also referred to as one-pot synthesis). For example, primers may be simultaneously provided with a polymerase, reversibly blocked nucleotide analogs, and a deblocking agent. The nucleic acids, polymerase, reversibly blocked nucleotide analogs and deblocking agent can be present in the reaction simultaneously. The polymerase is capable of catalyzing addition of a single reversibly blocked nucleotide analog to the primer to create an extended primer having a blocked 3' terminus. The deblocking agent is capable of deblocking the 3' terminus of the extended primer such that subsequent nucleotide analogs can be added to the extended primer. In yet another embodiment, the nucleotides may not have a 3' block and a deblocking agent is not added. Changes in resistance may be monitored in real time as the polymerase incorporates successive nucleotides Such embodiments may be particularly applicable for analysis of single-molecules. Because the reagents are together simultaneously, the primer can be sequentially extended to incorporate several nucleotide analogs in a single pot reaction. At least one advantage of a single pot reaction is that reagents need not be added to the reaction nor removed from the reaction, thereby reducing reagent waste caused by repetitive fluid transfers and increasing turnaround time for the reaction by minimizing time consuming fluidic transfer steps. SBS sequencing through single pot reactions is described in U.S. Patent Application Publication No. 2013/0085073, which is hereby incorporated by reference in its entirety.

During the single pot reactions, the magnetically-responsive sensors effectively monitor the complementary strand and detect when a nucleotide is added to the strand. In such embodiments, either the nucleotide or the polymerase may have the magnetic particle attached thereto. For example, each type of nucleotide may have a magnetic particle (or particles) that provide a unique magnetic property such that the nucleotide is distinguishable from other types of nucleotides. In other embodiments, the polymerase may have the magnetic particles attached thereto. As described herein, different types of nucleotides may have different incorporation rates such that embodiments may identify the type of nucleotide that was added.

As described herein, the template strands in some embodiments may be immobilized to, for example, a surface of a flow cell. In other embodiments, however, polymerase may be immobilized to the surface of a flow cell. The polymerase may be immobilized within a small reaction chamber or well. For example, the polymerase may be located within a small volume (e.g., zeptoliter-scale) such that freely diffusing magnetic particles may be readily distinguished from those stably associated with the polymerase, based upon the time that the signal is present. Each volume may be assigned to one or more magnetically-responsive sensors.

The polymerase may be immobilized to a surface using known linkers. Examples of such linkers include: NHS-esters, isocyanates, and isothicyanate linker conjugation to amines, maleimides to cysteines, click-chemistry with azides to alkynes, use of fusion tags such as Halotag, Spycatcher-Spytag, and other similar protein-protein bioconjugation methods. For further information about exemplary linkages that can be used, see the following references, the entire contents of each of which are incorporated by reference herein: Hermanson, Bioconjugate Techniques, 2nd Ed., Elsevier, 2008; Zakeri et al., "Peptide tag forming a rapid covalent bond to a protein, through engineering a bacterial adhesin," PNAS 109(12): E691-E697 (2012); and Liu et al., "Specific Enzyme Immobilization Approaches and Their Application with Nanomaterials," Topics in Catalysis 55(16-18): 1146-1156 (2012).

In one illustrative embodiment, the reduced thiol (—SH) group (also called a sulfhydryl group) of a cysteine residue can be reacted with a tether having a thiol-reactive group. Examples of such groups include maleimide and iodoacetamide. Primary thiolreactive reagents, including iodoacetamides, maleimides, benzylic halides, and bromomethylketones can react by S-alkylation of thiols so as to generate stable thioether products; arylating reagents such as 7-nitrobenz-2,1,3-oxadiazole (NBD) halides can react with thiols or amines by a similar substitution of the aromatic halide by the nucleophile; and because the thiolate anion is a better nucleophile than the neutral thiol, cysteine is more reactive above its pKa. Additionally, sulfhydryl-reactive chemical groups include haloacetyls, maleimides, aziridines, acryloyls, arylating agents, vinylsufones, pyridyl disulfides, TNB-thiols (2-nitro-5-thiobenzoic acid), and disulfide reducing agents; such groups can conjugate to sulfhydryls via alkylation (e.g., via formation of a thioether bond) or disulfide exchange (e.g., formation of a disulfide bond). Sulfhydryl exchange reactions also suitably can be used.

Alternatively, amines (—NH$_2$) can be targeted. For example, the primary amine of the lysine residue and the polpypeptide N-terminus are relatively reactive. Amine residues can be targeted with N-hydroxysuccinimide esters (NHS esters), which can form a stable amide bond, or imidoester crosslinkers, which can react with primary amines to form amidine bonds. There are many other amine-reactive compounds. For example, synthetic chemical groups that can form chemical bonds with primary amines include isothiocyanates, isocyanates, acylazides, NHS esters, sulfonyl chlorides, aldehydes, glyoxals, epoxides, oxiranes, carbonates, aryl halides, imidoesters, carbodiimides, anhydrides, and fluorophenyl esters; such groups can conjugate to amines, for example, via acylation or alkylation. In still other embodiments, a modified amino acid residue can be used to introduce a novel functionality like an azide or alkyne to be used with click chemistry. For example, thiol or amine reactivities such as described above can be used with linkers that permit the addition of azide or alkyne functionalities to further be used in a click chemistry reaction.

In some embodiments, the sequencing may be carried by causing a designated reaction that bonds two moieties or separates (e.g., cleaves) two moieties. In many cases, the designated reaction may be caused chemically or enzymatically. In some embodiments, however, the designated reaction may be caused by changing a temperature or electrical characteristic that is experienced by the reactants.

In some embodiments, the magnetic particles have magnetic properties or states that are substantially constant or uniform. For example, the magnetic properties may provide a constant or uniform magnetic field. In other embodiments, however, the magnetic property or state may be inducible or tunable. For instance, the magnetic properties may be altered from one state to another state by applying electromagnetic energy of a designated frequency.

Various embodiments also include a system and/or a detection apparatus. As used herein, a "detection apparatus" includes an array of magnetically-responsive sensors and a chamber that permits the flow of fluid therethrough proximate to the magnetically-responsive sensors. In various embodiments, the detection apparatus includes a solid state device. The flow of fluid may be, for example, a continuous flow of liquid, such as those described in U.S. Patent Application Publication No. 2015/0079596, U.S. Pat. No. 8,951,781, and International Publication No. WO 2015/089092, each of which is incorporated by reference in its entirety. Alternatively, the flow of fluid may also be directed through droplet operations, such as electrowetting operations, which are described in greater detail herein.

Embodiments may comprise a magnetic biosensing SBS scheme based on magnetoresistance and/or spintronics. For example, a flow cell or a droplet actuator may comprise a high density, magnetic sensor array based on giant magnetoresistance (GMR) devices and/or tunnel magnetoresistance (TMR) devices. The GMR devices and TMR devices may also be referred to as GMR sensors or TMR sensors, respectively. In particular embodiments, the magnetic sensor array may be used for detecting amplified clonal clusters of DNA or single strands of DNA that are labeled with magnetic particles. The magnetic particles may be, for example, magnetic nanoparticles and/or single-molecule magnets (SMMs).

As used herein, an array of magnetically-responsive sensors includes a plurality of sensors having a designated arrangement. The array may include sensors that are positioned side-by-side in a grid or matrix arrangement (e.g., 10 rows and 10 columns) or the array of sensors may have a more dispersed, non-uniform arrangement. In some embodiments, the magnetically-responsive sensors of the array may be positioned immediately adjacent to each other without any intervening elements In other embodiments, however, the magnetically-responsive sensors of the array may be spaced from each other. Optionally, other elements (e.g., electrodes) may be positioned between adjacent magnetically-responsive sensors.

In some embodiments, biological or chemical samples may be selectively positioned adjacent to one or more magnetically-responsive sensors of the array prior to detecting signals. For example, each magnetically-responsive sensor may be assigned to a corresponding area or volume (referred to generally as a designated space) such that the magnetically-responsive sensor is configured to detect an external magnetic field from the designated space. As a specific example, template strands may be immobilized to a surface or matrix located at the designated space. As another example, the biological or chemical sample may be positioned within a recess (e.g., well) that is positioned over one or more magnetically-responsive sensors.

Alternatively, the biological or chemical samples may have unknown positions along the magnetic sensor array prior to detection. In such embodiments, it may be determined only after detection of the magnetic particles whether the magnetic particles are within the designated spaces of the magnetically-responsive sensors. In such embodiments, one or more of the magnetically-responsive sensors may not be able to detect a biological or chemical sample. In other embodiments, a plurality of magnetically-responsive sensors may be proximate to a single sample such that each of the plurality of sensors can detect the same magnetic particle or can detect different magnetic particles that are coupled to the same sample.

As used herein, phrases such as "an array of [elements]" or "a plurality of [elements]" and the like, when used in the detailed description and claims, do not necessarily include each and every element that a component may have. The component may have other elements that are similar to the plurality of elements. For example, the phrase "a plurality of magnetically-responsive sensors [having a recited feature]" does not necessarily mean that each and every magnetically-responsive sensor of a detection apparatus has the recited feature. Other magnetically-responsive sensors may not include the recited feature. Accordingly, unless explicitly stated otherwise (e.g., "each and every magnetically-responsive sensor [having a recited feature]"), embodiments may include similar elements that do not have the recited features.

Each of the magnetically-responsive sensors may be used to detect a change in electrical resistance. For example, each of the magnetically-responsive sensors may have an electrical resistance associated with it. The magnetically-responsive sensor may detect changes in the electrical resistance that are caused by, for example, a magnetic property of a material positioned proximate to the magnetically-responsive sensor. As used herein, a "magnetic property" may include a magnetic field, a magnetic direction, a magnetic moment. The magnetic property may be caused by materials that exhibit paramagnetism, diamagnetism, ferromagnetism, and antiferromagnetism. The magnetic property may also be caused, at least in part, by the spins of electrons in the material In some embodiments, the magnetic property may be immutable. In other cases, however, the magnetic property may be altered or induced.

For example, a GMR sensor may have a conducting layer that has an electrical resistance that is capable of changing when in the presence of a material having a designated magnetic property. For example, magnetic particles may have respective magnetic fields or magnetic moments that cause a change in resistance. The GMR sensor may have a first electrical resistance when the external magnetic field is not present and a second electrical resistance when the external magnetic field is present. Likewise, a TMR sensor may have an insulative layer that exhibits a tunneling current. The flow of the tunneling current is impeded by the electrical resistance of TMR sensor. The TMR sensor may have a first electrical resistance when the magnetic material is not present and a second electrical resistance when the magnetic material is present. Embodiments herein are capable of determining a difference in the electrical resistance to determine whether the magnetic material was present In some cases, the magnetic material may have different magnetic properties. As such, embodiments may be able to discriminate different magnetic fields and/or different magnetic moments.

For each magnetically-responsive sensor, circuitry of the detection apparatus, such as the circuitry included in a readout circuit, may transmit signals that correlate to the electrical resistance at the magnetically-responsive sensor. For example, the circuitry may be electrically coupled to one or more of the layers of the magnetically-responsive sensor, such as one of the ferromagnetic layers and/or one of the nonmagnetic layers. The signals from when the external magnetic fields are present and are not present may be compared to detect a change in the electrical resistance. The change in electrical resistance may determine whether magnetic particles were present when the signals were transmitted. For example, any substantial change in the electrical resistance may indicate that the magnetic particles are present. Moreover, in some embodiments, a magnitude of the change may be analyzed to determine a type of magnetic particle that is present or a number of magnetic particles that are present. In other words, embodiments may be configured to (a) detect whether any magnetic field was present at the designated space or (b) identify a strength of the magnetic field that was present in the designated space. With this data, embodiments may be able to determine useful information regarding the biological or chemical sample. The useful information may be, for instance, the identity of a nucleotide or the sequence of a nucleic acid.

As described above, embodiments may receive signals, which represent the electrical resistance, when the magnetic property is present and when the magnetic property is not present. This data may be analyzed to determine a change in electrical resistance. It should be understood that embodiments may also receive the signals when the magnetic property has a first state or quality and when the magnetic property has a different second state or quality. Again, this data may be analyzed to determine a change in electrical resistance. For instance, the magnetic material may have a magnetic property that is altered or induced. As one example, a SMM particle may be sensitive to a different set of ON/OFF light frequencies. The magnetic state of the SMM particle may be altered by providing an ON light frequency or an OFF light frequency. Thus, embodiments may compare signals that were received after the ON light frequency was applied to signals that were received after the OFF light frequency was applied.

Examples described below include determining the changes in electrical resistance caused by magnetic fields alone. It should be understood, however, that such changes may be caused by other magnetic properties (e.g., magnetic direction and/or moment) depending upon the implementation.

In particular embodiments, the devices and methods may be used for sequencing amplified clonal clusters of DNA or single strands of DNA.

In particular embodiments, hapten labeled nucleotides and functionalized magnetic nanoparticles are used for detection and discrimination of a nucleotide incorporation event in a magnetic biosensing SBS scheme.

In particular embodiments, nucleotides labeled with SMMs are used for base detection and discrimination in a magnetic biosensing SBS scheme.

In particular embodiments, unlabeled nucleotides and a functionalized DNA polymerase are used for base detection and discrimination in a magnetic biosensing SBS scheme. In one example, DNA polymerase is functionalized (tagged) with a magnetic particle, such as a single-molecule magnet.

1.1 Magnetoresistive Sensors for DNA Sequencing

Embodiments set forth herein may include methods, systems, devices, and apparatuses for biological or chemical analysis using a magnetic sensing scheme. For example, embodiments may include devices and methods of using magnetic biosensing for DNA sequencing, such as for supporting a magnetic biosensing SBS scheme. Namely, one or more embodiments provide a flow cell and/or droplet actuator that comprises a magnetic biosensing SBS scheme based on magnetoresistance and/or spintronics. Magnetoresistance is the property of a material to change the value of its electrical resistance when an external magnetic field is applied to it. Certain materials (and multilayer devices) show giant magnetoresistance (GMR), colossal magnetoresistance (CMR), tunnel magnetoresistance (TMR), and extraordinary magnetoresistance (EMR). Generally, resistance can depend either on magnetization (controlled by applied magnetic field) or on magnetic field directly. Spintronics, also known as spinelectronics or fluxtronic, is an emerging technology exploiting both the intrinsic spin of the electron and its associated magnetic moment, in addition to its fundamental electronic charge, in solid-state devices. In spintronics, the spins are not only manipulated by magnetic fields, but also by electrical fields.

One or more embodiments may use, for example, an array of GMR-based and/or TMR-based sensors. Whereas detection mechanisms of conventional SBS devices require bulky and expensive optical systems, GMR-based and/or TMR-based sensors can leverage known semiconductor manufacturing processes for making memory arrays, which can be used for fabricating magnetic sensor arrays cheaply. Further, using these known semiconductor manufacturing processes, high density magnetic sensor arrays can be implemented in a magnetic biosensing SBS scheme in, for example, a flow cell and/or a droplet actuator.

In so doing, embodiments may provide an inexpensive, portable, non-optical sequencing device in which (1) even the most complex biological samples lack a detectable magnetic background signal, (2) biological samples do not interfere with the magnetic transduction mechanism, and (3) contamination from salt, pH, fluorescence background is not an issue with respect to magnetic biosensing. Further, one or more embodiments may lend well to diagnostics (blood, cell lysate, saliva, urine, etc.). With respect to sequencing, these characteristics lend themselves to single molecule detection (in some embodiments the clusters still have an advantage for accuracy) and minimal sample-prep applications.

Figure 1B:
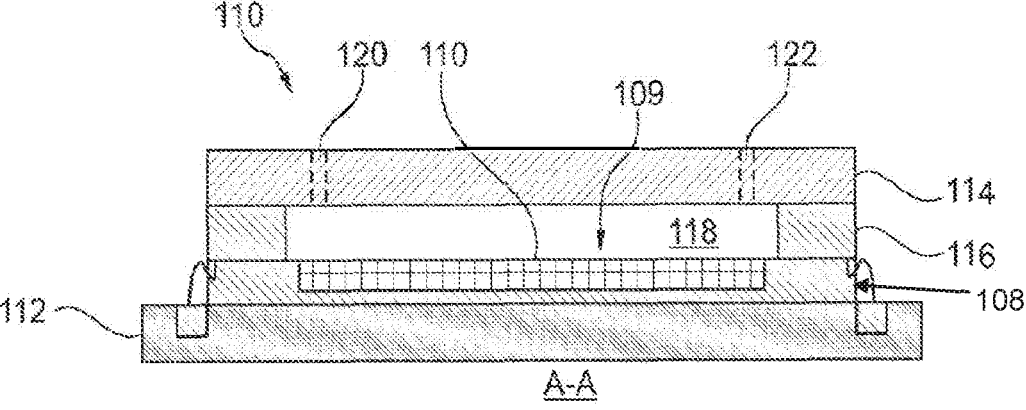
FIG. 1B illustrates a cross-sectional view of the system of FIG. 1A.

FIGS. 1A and 1B illustrate a top view and cross-sectional view, respectively, of an example of a system 100. In the illustrated embodiment, the system 100 includes a detection apparatus (or detector) 102, a fluidic-control system 104 (FIG. 1A) that is in flow communication with the detection apparatus 102, a readout circuit 106 (FIG. 1A), and an analysis circuitry 105 (FIG. 1A). The detection apparatus 102 comprises a magnetic sensor array 110 for supporting, for example, a magnetic biosensing SBS scheme. For example, the detection apparatus 102 includes a bottom substrate 108 that includes a printed circuit board (PCB) 112 and a magnetic sensor array 110 that is mounted onto the PCB 112. The detection apparatus 102 also includes a top substrate (or flow cell) 114 that is provided in relation to magnetic sensor array 110. The magnetic sensor array 110 is positioned along a substrate surface 109 (FIG. 1B) of the bottom substrate 108. A chamber or reservoir 118 is defined between the substrate surface 109 and the top substrate 114. The magnetic sensor array 110 may include a plurality of sensors that are positioned proximate to designated spaces within the chamber 118. For example, the sensors may have exposed surfaces that define the chamber 118. Alternatively, one or more layers (e.g., passivation layer) may be positioned between the chamber 118 and the magnetic sensor array 110. For example, the substrate surface 109 may be defined by a passivation layer. In the illustrated embodiment, the top substrate 114 and the bottom substrate 108 are separated by spacers 116. In other embodiments, the top substrate 114 may be shaped to form a recess that becomes the chamber 118 when the top substrate 114 is mounted to the bottom substrate 108.

Top substrate 114 can be, for example, a glass substrate or plastic substrate. In one example, top substrate 114 is about 400 μm thick. In one example, spacers 116 are adhesive spacers that are about 100 μm in height. In another example, spacers 116 are risers integrated with either the top or bottom substrate and are about 100 μm in height. Sequencing chamber 118 is a flow channel that is supplied by an inlet 120 and an outlet 122 in top substrate 114. Namely, liquid can flow in/out of sequencing chamber 118 using inlet 120 and outlet 122.

In one example, magnetic sensor array 110 is a 10×10 array in which the pitch of the magnetically-responsive sensors can range, for example, from about 10 μm to about 100 μm. In another example, magnetic sensor array 110 is a high density, CMOS-based magnetic sensor array, such as a 8,000×8,000 array in which the pitch of the magnetically-responsive sensors is about 200 nm (per current 64 Mbit devices), or a 100,000×100,000 array in which the pitch of the magnetically-responsive sensors is about 100 nm (per current 10 Gbit devices). In one example, magnetic sensor array 110 is a 100 nm×400 nm device.

The magnetically-responsive sensors that form magnetic sensor array 110 can be, for example, GMR-based devices or sensors or TMR-based devices or sensors. The GMR-based devices or TMR-based devices can be used to, for example, detect amplified clonal clusters of DNA or single strands of DNA that are labeled with, for example, magnetic nanoparticles and/or SMMs. The system 100 may be used for other applications, such as diagnostic applications, in which probes or other moieties having magnetic particles selectively attach to designated biological or chemical targets.

As shown in FIG. 1A, the readout circuit 106 is separate from the detection apparatus 102. In other embodiments, however, the readout circuit 106 may be entirely integrated with the detection apparatus 102. For example, the detection apparatus 102 may include a solid state device, such as a CMOS, that includes circuitry that forms at least a portion of the readout circuit 106. In some embodiments, the bottom substrate 108 may include a CMOS device.

The readout circuit 106 is communicatively coupled to the magnetically-responsive sensors that form the array 110. The readout circuit 106 is configured to transmit signals, which may be based on (or indicative of or representative of) electrical resistances of the magnetically-responsive sensors, to the analysis circuitry 105. The readout circuit 106 includes conductive pathways. In some embodiments, the readout circuit 106 includes circuitry that is configured to modify the signals prior to transmitting the signals to the analysis circuitry 105. For example, the readout circuit 106 may amplify the signals, digitize the signals, convert the signals based on a look-up table, etc. Alternatively, the readout circuit 106 does not modify the signals prior to transmitting the signals to the analysis circuitry.

In some embodiments, the readout circuit 106 determines an electrical resistance at the magnetically-responsive sensors and transmits this data to the analysis circuitry 105. In other embodiments, the readout circuit 106 transmits the raw data to the analysis circuitry 105 and the analysis circuitry determines the electrical resistance at each magnetically-responsive sensor. The electrical resistance may be calculated by using Ohm's law or another formula/algorithm that is based, at least in part, on Ohm's law. An electrical resistance may be calculated, for example, by providing information (e.g., detected current or voltage) to a look-up table that converts the information to a signal or value that is representative of the electrical resistance.

The analysis circuitry 105 is configured to receive (directly or indirectly) signals from the readout circuit 106 and analyze the signals in accordance with one or more predetermined algorithms/formulas to provide useful information. Optionally, the analysis circuitry 105 may be integrated with the detection apparatus 102. For example, the analysis circuitry may be secured to the bottom substrate 108.

The readout circuit 106 and/or the analysis circuitry 105 may determine a detected change in electrical resistance at each of the magnetically-responsive sensors. As used herein, the phrase "determine a detected change in electrical resistance" (and the like) is not intended to be limited to a simple mathematical calculation. In some cases, the only information that is necessary is whether the electrical resistance (or other characteristic that is indicative of the electrical resistance, such as the current or voltage) satisfies a certain condition. For example, if the electrical resistance is below a designated value, then the reading may be designated as a positive reading (i.e., a magnetic particle was present within the designated space). If the electrical resistance is above a designated value, then the reading may be designated as a negative reading (i.e., no magnetic particles were present). In the above example, the amount that the electrical resistance differs from the designated value is irrelevant. The query is only whether the electrical resistance was above or below the designated value.

In other embodiments, however, the amount that the electrical resistance (or other electrical characteristic) differs from a designated value may be useful. For example, the amount of change in electrical resistance may be indicative of a strength of the magnetic field. The strength of the magnetic field, in turn, may correspond to a number of magnetic particles and/or a type of magnetic particles within a designated space.

Accordingly, the step of determining a detected change in electrical resistance may include (a) determining if any change exists and/or (b) determining an amount of the change. Moreover, the step of determining a detected change in electrical resistance may include using values that are representative of other electrical characteristics (e.g., current, voltage).

As one example, the detected change may be determined by finding a difference between a first detected value (e.g., baseline electrical resistance, baseline current, or baseline voltage) that is obtained at a first time period, such as after a cleaving operation, and a second detected value that is obtained at a subsequent second time period, such as after an incorporation event.

As another example, the detected change may be determined only after receiving a single detected value. For instance, a designated threshold or baseline value may be assigned for each magnetically-responsive sensor in the array. Readings may be identified as positive or negative by comparing this designated value to the detected value.

In other embodiments, the detected value may be applied to a look-up table, which may provide an output. The output may be indicative of strength of magnetic field, which may, in turn, correspond to a number of magnetic particle and/or a type of magnetic particles within the designated spaces.

In other embodiments, the detected value may be compared to a plurality of different values. Each of these different values may correspond to a type of magnetic particle. For example, if the detected value is approximately equal to a first magnitude, then a first type of magnetic particle may be within the designated space. If the detected value is approximately equal to a second magnitude, then a second type of magnetic particle may be within the designated space. Similarly, the detected value may be compared to a plurality of different value ranges. If the detected value is within a first range, then a first type of magnetic particle may be within the designated space. If the detected value is in a second range, then a second type of magnetic particle may be within the designated space.

The detected value may represent a single value that is obtained at one instant. In some cases, however, the detected value may be obtained over a predetermined time period or over multiple predetermined time periods. For example, the detected value may be a maximum or minimum value that is detected during the time period or may be an average value that is detected during the time period. Yet in other embodiments, the duration that a change in electrical resistance exists may also provide useful information.

The analysis circuitry 105 is configured to analyze the detected changes to provide useful information regarding the biological or chemical sample. For example, the analysis circuitry 105 may identify or call the nucleotide that was added for each SBS event to determine a sequence for a nucleic acid. An SBS event may include one or more steps for causing an addition of a nucleotide to a complementary sequence and one or more steps for detecting the addition. An SBS event may include adding a single nucleotide to a plurality of clusters (e.g., hundreds, thousands of clusters) or may include adding a single nucleotide to a single complementary strand. Various methods for identifying the nucleotide are described herein. The methods may include the processes described above for detecting changes in electrical resistance. For example, in some embodiments, only a single detected change is sufficient for identifying the nucleotide. In other embodiments, two or more detected changes may be compared for identifying the nucleotide.

In some embodiments, a nucleotide may be called and/or a sequence may be determined by comparing, for each SBS event, the detected changes associated with a plurality of the magnetically-responsive sensors. For example, if a first magnetically-responsive sensor has a first electrical resistance, and a second magnetically-responsive sensor has a different second electrical resistance, then it may be determined that the magnetic particles that are detected by the first and second sensors are different. If a third magnetically-responsive sensor has an electrical resistance that is essentially equal to the electrical resistance for a fourth magnetically-responsive sensor, then it may be determined that the magnetic particles that are detected by the third and fourth sensors are the same.

In some embodiments, a nucleotide may be called and/or a sequence may be determined by comparing the different detected changes associated with each magnetically-responsive sensor. For example, after an SBS protocol, a magnetically-responsive sensor may have a hundred different readings associated with it. Each reading may correspond to one of four bases being incorporated into the complementary strand. Based on the assumption that magnetic particles of the same type (or same number) will provide the same changes in electrical resistance, the nucleotides may be called for each reading.

The readout circuit 106 and/or the analysis circuitry 105 may include a hardware and/or software system that operates to perform one or more functions. For example, the readout circuit 106 and/or the analysis circuitry 105 may include a computer processor, controller, or other logic-based device that performs operations based on instructions stored on a tangible and non-transitory computer readable storage medium, such as a computer memory. Alternatively, the readout circuit 106 and/or the analysis circuitry 105 may include a hard-wired device that performs operations based on hard-wired logic of the device.

The readout circuit 106 and/or the analysis circuitry 105 may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a readout circuit or analysis circuitry that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation. Moreover, it is noted that operations performed by the readout circuit 106 and/or the analysis circuitry 105 (e.g., operations corresponding to processes or methods discussed herein, or aspects thereof) may be sufficiently complex that the operations may not be performed by a human being within a reasonable time period.

The system and/or the detection apparatus may also include a fluidic-control system that is configured to flow reagents, in accordance with a designated schedule, through the chamber for conducting a predetermined protocol. The fluidic-control system includes a network of channels, which may be formed by tubes, flow cells, or other fluidic devices. Flow may be controlled by one or more valves and pumps that are selectively activated to deliver the desired reagent. The protocol may be an SBS protocol in which reagents, including a plurality of types of nucleotides, enzymes (e.g., polymerase), or other reaction components, are provided to the designated spaces to extend template strands. The fluidic-control system may be similar to or operate in a manner similar to the systems described in U.S. Patent Application Publication Nos. 2015/0079596 and 2015/0045234; U.S. Pat. Nos. 8,951,781 and 8,173,080; and International Publication Nos. WO 2014/143010 and WO 2015/089092, each of which is incorporated herein by reference in its entirety. After or during each incorporation event, the readout circuit may transmit the signals to the analysis circuitry.

In some embodiments, the fluidic-control system provides a continuous flow of the reagents. In other embodiments, however, the detection apparatus 102 includes a droplet actuator. For example, at least one of the top and bottom substrates 114, 108 may include electrodes for executing droplet operations. The electrodes may be interleaved or distributed within the magnetic sensor array 110. Alternatively, the magnetic sensor array 110 may be positioned opposite the electrodes with the chamber 118 therebetween in other embodiments.

Figure 2A:
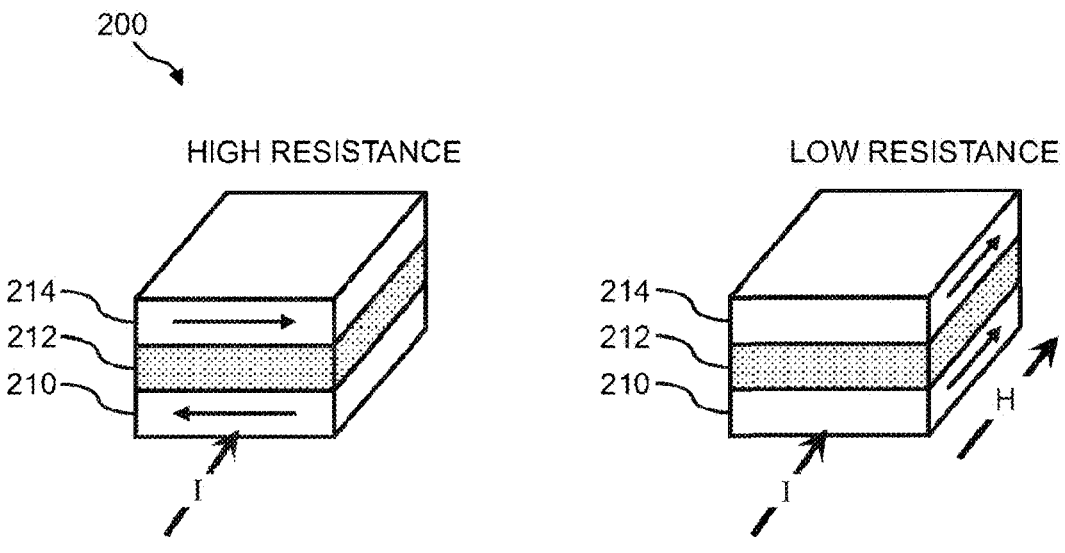
FIG. 2A shows an example of a GMR device.
Figure 2B:
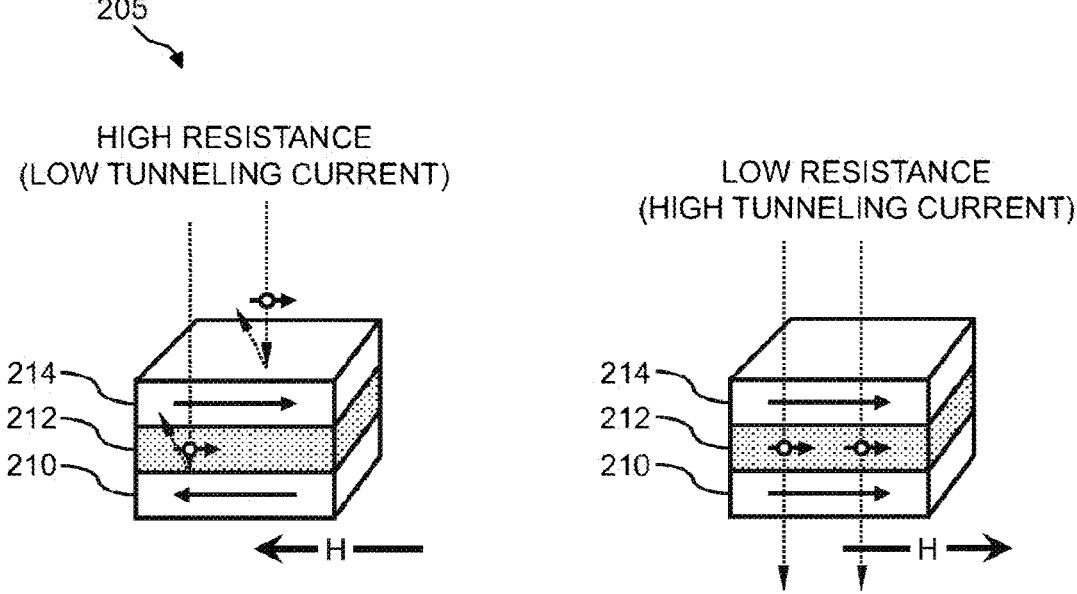
FIG. 2B shows an example of a TMR device.

FIGS. 2A and 2B show an example of a GMR device 200 and a TMR device 205, respectively. Both GMR device 200 and TMR device 205 comprise a pair of ferromagnetic layers separated by a nonmagnetic layer.

Referring now to FIG. 2A, GMR device 200 comprises a first ferromagnetic layer 210, a nonmagnetic layer 212, and a second ferromagnetic layer 214. Nonmagnetic layer 212 is sandwiched between ferromagnetic layer 210 and ferromagnetic layer 214. Ferromagnetic layer 210 and ferromagnetic layer 214 are ferromagnetic alloys. Nonmagnetic layer 212 is an ultrathin, nonmagnetic, electrically conductive layer (e.g., a copper layer).

FIG. 2A shows GMR device 200 in two states, wherein the direction of the magnetization in ferromagnetic layer 214 is fixed or "pinned" using a pinning layer (not shown) atop ferromagnetic layer 214. First, the magnetic moment in ferromagnetic layer 210 and ferromagnetic layer 214 face opposite directions due to antiferromagnetic coupling. In this state, the resistance to current (I) is high. The copper nonmagnetic layer 212 is normally an excellent conductor, but when it is only a few atoms thick, electron scattering causes copper's resistance to increase significantly. This resistance changes depending on the relative orientation of electron spins surrounding the conducting layer (i.e., nonmagnetic layer 212).

Next, the state of GMR device 200 can flip by applying an external magnetic field (H) that overcomes the antiferromagnetic coupling and aligns the magnetic moments in ferromagnetic layer 210 and ferromagnetic layer 214. The exposure to external magnetic field (H) changes (i.e., reduces) the device resistance so the structure can be used to sense an external field. Practical devices are often made of multiple layers of alternating magnetic and nonmagnetic layers to improve sensitivity. The change in resistance when the GMR device 200 is subjected to a magnetic field can typically be from 10% to about 20%, which is large compared with a maximum sensitivity of a few percent for other types of magnetic sensors.

Referring now to FIG. 2B, TMR device 205 comprises ferromagnetic layer 210, nonmagnetic layer 212, and ferromagnetic layer 214. However, wherein the nonmagnetic layer 212 in GMR device 200 is electrically conductive, in TMR device 205 the nonmagnetic layer 212 is a thin insulating layer.

When two ferromagnetic layers (e.g., ferromagnetic layer 210 and ferromagnetic layer 214) are separated by a thin insulator layer (e.g., nonmagnetic layer 212), electrical resistance of the multilayer in the perpendicular direction to the film changes depending on the orientations of the magnetizations of ferromagnetic layers because of spin dependent electron tunneling between the two ferromagnetic layers.

FIG. 2B shows TMR device 205 in two states, wherein the direction of the magnetization in ferromagnetic layer 214 is fixed or "pinned" using a pinning layer (not shown) atop ferromagnetic layer 214. First, when the directions of the magnetizations of the two ferromagnetic layers are opposite, the electron with opposite spin orientation with respect to the magnetization of the ferromagnetic layer cannot be tunneled. Then the tunneling electron current becomes smaller (i.e., higher resistance) compared to the case for the same directions of the magnetizations. Next when the directions of the magnetizations of the two ferromagnetic layers are the same, the possibility of electron tunneling between the two ferromagnetic layers through the insulator layer becomes larger, resulting in larger tunneling current (i.e., lower resistance).

The device geometries of GMR device 200 of FIG. 2A and TMR device 205 of FIG. 2B are based on parallel anisotropy, meaning the free and pinned layer magnetizations are parallel to the plane of substrate. However, magnetic sensor array 110 can be based on any known GMR/TMR device geometries. In another example, magnetic sensor array 110 can be based on GMR/TMR geometries that utilize perpendicular anisotropy instead of parallel anisotropy, meaning the free and pinned layer magnetizations are perpendicular to the plane of substrate.

Figure 3:
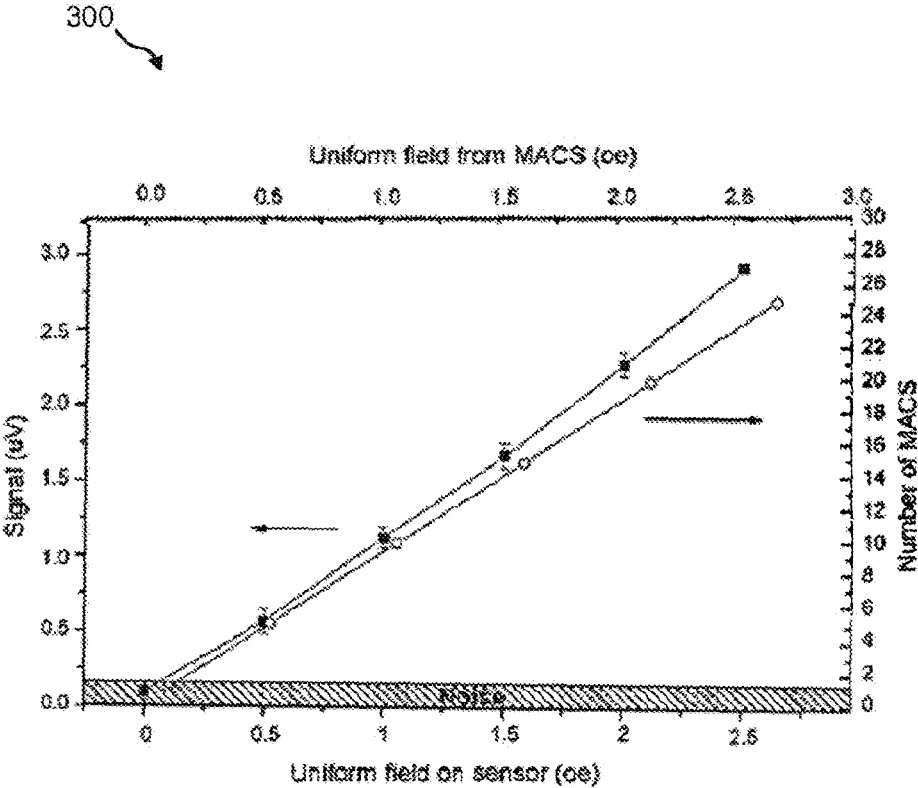
FIG. 3 shows an example of a plot of the sensitivity of a GMR biochip using a single magnetic nanoparticle.

With respect to using a GMR-based and/or TMR-based magnetic sensor array 110 of flow cell 100 for detecting amplified clonal clusters of DNA or single strands of DNA that are labeled with, for example, magnetic nanoparticles and/or SMMs, FIG. 3 shows an example of a plot 300 of the sensitivity of a GMR biochip using a single magnetic nanoparticle. Referring now to plot 300, measured uniform field dependence of the pre-amplified signal demonstrates the minimum detectable field change is better than 0.1 Oe. A single nanoparticle generates the uniform field of 0.12 Oe over the sensor area (by simulation), which indicates the GMR biochip can perform single nanoparticle (molecule) detection. The use of clusters comprising one or more DNA molecule templates would be expected to increase the intensity of the readout signal.

Figure 4:
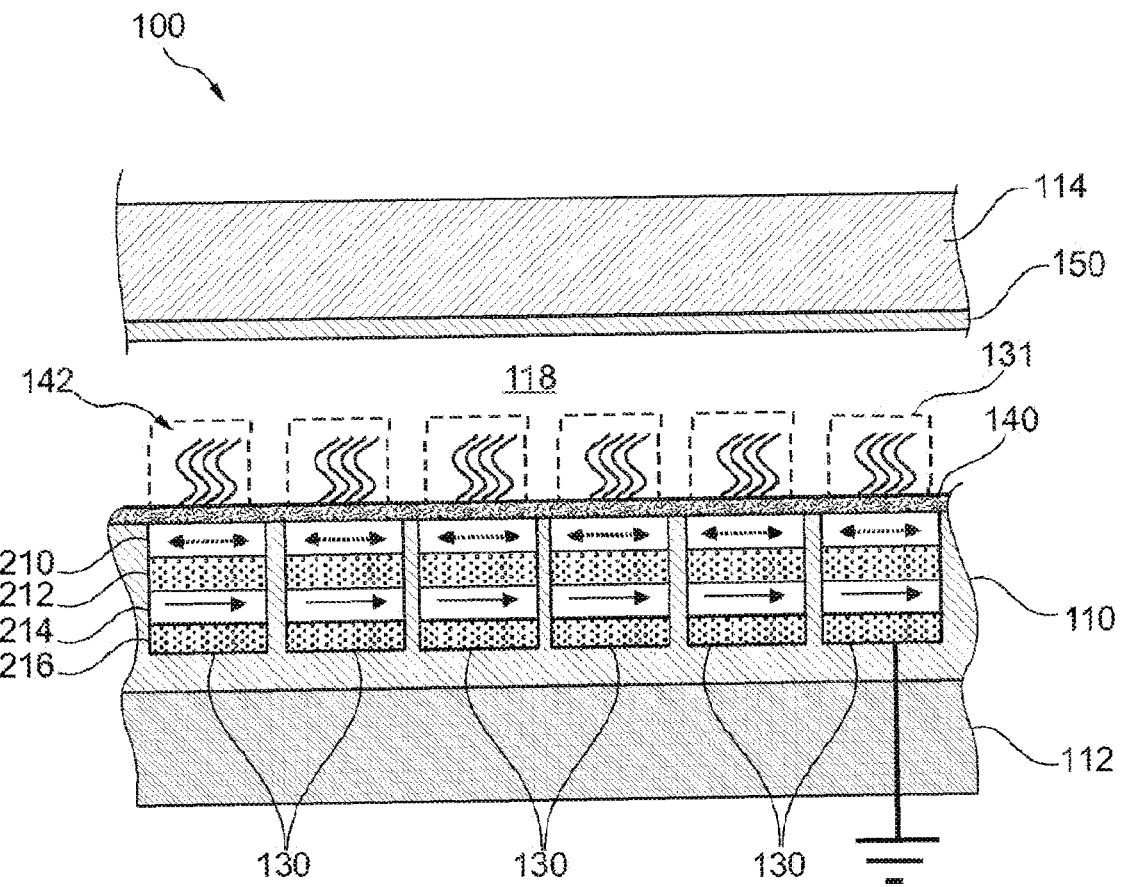
FIG. 4 illustrates a cross-sectional view of a portion of a detection apparatus shown in FIGS. 1A and 1B and shows more details of the magnetic sensor array.

FIG. 4 is a cross-sectional view of a portion of the detection apparatus 102 shown in FIGS. 1A and 1B, and shows more details of the magnetically-responsive sensors of the magnetic sensor array 110. Again, the detection apparatus 100 comprises the magnetic sensor array 110 mounted to the PCB 112. FIG. 4 shows that magnetic sensor array 110 comprises a plurality of magnetically-responsive sensors 130. In some embodiments, the magnetically-response sensors 130 may be arranged in rows and columns. However, other arrangements may be selected based on the desired application. Each of the magnetically-responsive sensors 130 can be, for example, a GMR-based device (e.g., GMR device 200 of FIG. 2A) or a TMR-based device (e.g., TMR device 205 of FIG. 2B). Each of the magnetically-responsive sensors 130 may include a nonmagnetic layer 212 that is sandwiched between a first ferromagnetic layer 210 and a second ferromagnetic layer 214. In this example, first ferromagnetic layer 210 of each magnetically-responsive sensor 130 is oriented toward the chamber 118. Further, the direction of the magnetization in second ferromagnetic layer 214 is fixed or "pinned" using a pinning layer 216 that is adjacent to second ferromagnetic layer 214. Although FIG. 4 only illustrates first and second ferromagnetic layers 210, 214 and a nonmagnetic layer 212, it should be understood that other embodiments may include more than two ferromagnetic layers and more than one nonmagnetic layer stacked with respect to each other.

As shown, each of the magnetically-responsive sensors 130 is configured to detect an external magnetic field that is located or generated within a designated or an associated space 131 within the chamber 118. As used herein, the term "designated space" means a proximate space in which a magnetic particle or particles may be detected by a corresponding magnetically-responsive sensor. It should be understood that the size and shape of the designated space may be based on a plurality of factors, such as the size and strength of the magnetic particles, the configuration of the magnetically-responsive sensors (e.g., size, shape, and number of layers), or the sensitivity of the magnetically-responsive sensors. As such, the designated space may change based upon the application. Although it is contemplated that a magnetically-responsive sensor may detect an external magnetic field from a space that is adjacent to the designated space of the sensor, this external magnetic field may be relatively weak and any signals may be identified as noise.

In the illustrated embodiment, each of the designated spaces is only a small portion or volume of the chamber 118, which extends continuously alongside the magnetic sensor array 110 such that adjacent designated spaces are not physically separated by other matter, such as a wall. In other embodiments, however, the designated spaces may be physically separated from each other. For example, each designated space may exist within a well or recess that is defined by one or more walls. The walls may separate the designated spaces. For embodiments that include droplet actuators, the designated space may be occupied by a droplet when reagents are delivered to the designated space. In such embodiments, the designated spaces may be separated from each other by a filler fluid. However, it is also contemplated that a single droplet may occupy multiple designated spaces at once.

Additionally, FIG. 4 shows that detection apparatus 102 may include a layer 140 that is positioned between the magnetically-responsive sensors 130 and the chamber 118. FIG. 4 also shows that the detection apparatus 102 may include a conductive layer 150 positioned along top substrate 114. Conductive layer 150 on top substrate 114 can be, for example, a gold layer or indium tin oxide (ITO) layer. In one example, conductive layer 150 can be used as a Vdd reference plane that is common to all magnetically-responsive sensors 130 of magnetic sensor array 110.

Layer 140 may be formed of any hydrophilic material, hydrophobic material, or combination of hydrophilic and hydrophobic material suitable for conducting surface-based chemistry in the chamber 118. Layer 140 can be, for example, from about 300 nm to about 400 nm thick. In one example, layer 140 is a polyacrylamide gel coating, such as a mixture of norbornene (or norbornylene or norcamphene) and Poly(N-(5-azidoacetamidylpentyl) acrylamide-co-acrylamide), also known as PAZAM. More details about PAZAM can be found with reference to George et al., U.S. patent application Ser. No. 13/784,368, entitled "Polymer Coatings," filed on Mar. 4, 2013, the entire disclosure of which is incorporated herein by reference.

In FIG. 4, a plurality of oligonucleotide primers 142 are immobilized on layer 140 in chamber 118 and located in relation to magnetically-responsive sensors 130 of magnetic sensor array 110. In one example, oligonucleotide primers 142 are capture primers on which single-stranded DNA fragments are hybridized and amplified to form clonal DNA template clusters for SBS.

As described herein, in some embodiments, signal(s) provided during an SBS reaction may be provided, for example, via incorporation of a nucleotide(s) that is directly or indirectly labeled with a magnetic particle and detected using magnetically-responsive sensors 130 as described in more detail hereinbelow. A magnetic particle may be, for example, a magnetic nanoparticle or a SMM.

1.2 Magnetic Nanoparticle-Based SBS

In one embodiment, functionalized magnetic nanoparticles and hapten labeled nucleotides are used for detection of a nucleotide incorporation event in a magnetic biosensing SBS scheme. In one example, nucleotides (A, G, C, and T) are biotinylated and the magnetic nanoparticles are coated with streptavidin. For example, a single type of magnetic nanoparticle is used and four (4) fluidic/detection cycles are used for sequential addition of nucleotides in an SBS cycle.

FIGS. 5-12 illustrate various methods that may be performed by the systems and detection apparatuses set forth herein. For example, a method may include providing a detection apparatus that includes an array of magnetically-responsive sensors. Each of the magnetically-responsive sensors may be located proximate to a respective designated space to detect an external magnetic field therefrom. The detection apparatus also includes a plurality of nucleic acid template strands located within corresponding designated spaces. The method also includes conducting a plurality of SBS events to grow a complementary strand by incorporating nucleotides along each template strand. At least some of the nucleotides are attached to corresponding magnetic particles that provide respective magnetic fields. Each of the plurality of SBS events includes detecting changes in electrical resistance at the magnetically-responsive sensors caused by the respective magnetic fields of the magnetic particles. The method may also include determining sequences of the complementary strands. The sequences of the complementary strands are based on the detected changes in electrical resistance that occurred at the magnetically-responsive sensors for each of the plurality of SBS events.

Figure 5:
FIG. 5 shows a portion of the detection apparatus shown in FIGS. 1A, 1B and 4 and depicts an example of a magnetic biosensing SBS scheme, wherein an incorporated biotinylated nucleotide is used to capture a streptavidin-coated magnetic nanoparticle and generate a detectable signal.
Figure 5:
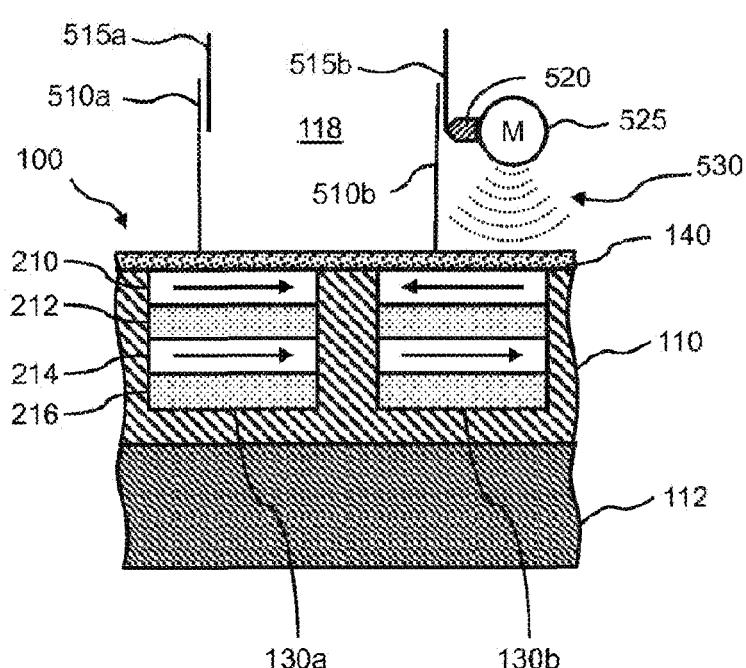

FIG. 5 shows a portion of flow cell 100 shown in FIGS. 1A, 1B, and 4 and depicts an example of a magnetic biosensing SBS scheme 500. In magnetic biosensing SBS scheme 500 an incorporated biotinylated nucleotide is used to capture a streptavidin-coated magnetic nanoparticle and generate a detectable signal. In this example, DNA template strands 510 (i.e., DNA template strands 510a and 510b) formed in a cluster amplification process are immobilized on layer 140. DNA template strand 510a is one template strand of a first clonal cluster and DNA template strand 510b is one template strand in a second clonal cluster. Hybridized to DNA template strands 510a and 510b are sequencing primers 515a and 515b, respectively. In abase addition reaction, a biotinylated nucleotide 520 is incorporated to extend sequencing primer 515. Biotinylated nucleotide 520 is described in more detail with reference to FIG. 6. In one example, biotinylated nucleotide 520 is dATP. Biotinylated nucleotide 520 is incorporated in the growing complementary strand only on DNA template 510b (i.e., dATP is not complementary for base addition on DNA template 510a). A solution (not shown) containing a plurality of streptavidin-coated magnetic nanoparticles 525 is flowed into sequencing chamber 118 of flow cell 100. Magnetic nanoparticle 525 may be, for example, superparamagnetic nanoparticles with a diameter of from about 10 nm to about 50 nm. Magnetic nanoparticle 525 binds to incorporated biotinylated nucleotide 520 through formation of a biotin-streptavidin binding complex. Unbound magnetic nanoparticles 525 are removed by washing. Magnetic particle 525 bound to incorporated nucleotide 520 alters the resistance of magnetic sensor 130b and the corresponding electrical signals are generated and measured. Whereas there is no magnetic nanoparticle 525 bound to DNA template strand 510a/sequencing primer 515a at magnetic sensor 130a, the signal generated by magnetic sensor 130a is different than the signal generated by magnetic sensor 130b.

Figures 6A, 6B:
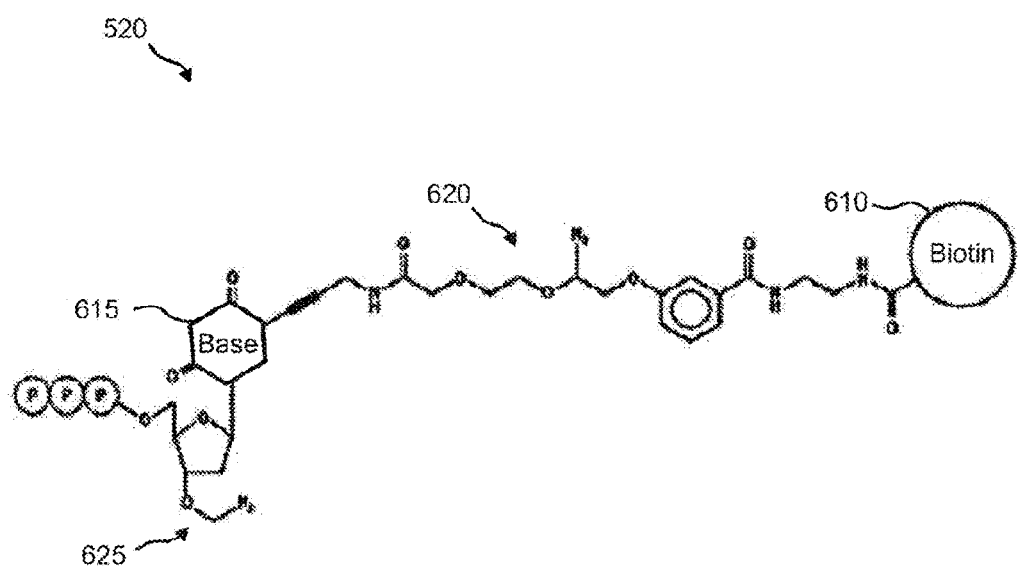
FIG. 6A illustrates a partial structural formula of the biotinylated nucleotide of FIG. 5.
FIG. 6B illustrates a partial structural formula of a nucleotide having a magnetic particle coupled to the gamma phosphate of the nucleotide.

FIG. 6A illustrates a partial structural formula of biotinylated nucleotide 520 of FIG. 5. Biotinylated nucleotide 520 includes a biotin label 610. Biotin label 610 is bound to a base 615 of nucleotide 520 via a cleavable linker 620. The 3' hydroxyl (OH) group of nucleotide 520 is protected by a blocking group 625. After incorporation of nucleotide 520 into a growing complementary DNA strand and detection (magnetic biosensing) of the incorporation event, the biotin/streptavidin magnetic nanoparticle complex may be removed from nucleotide 520 by cleavage of cleavable linker 620. After removal of biotin/streptavidin magnetic nanoparticle complex, the detection signal is returned to background levels. Blocking group 625 may be removed by a deblocking reaction for subsequent incorporation of the next complementary biotinylated nucleotide.

FIG. 6B illustrates a partial structural formula of a magnetically-labeled nucleotide 650, which may be used in some embodiments. The nucleotide 650 includes a base 655 and a magnetic particle 660 that is attached to the gamma phosphate 665 through a linker 670. A variety of linkers and a variety of magnetic particles may be used.

Figure 7:
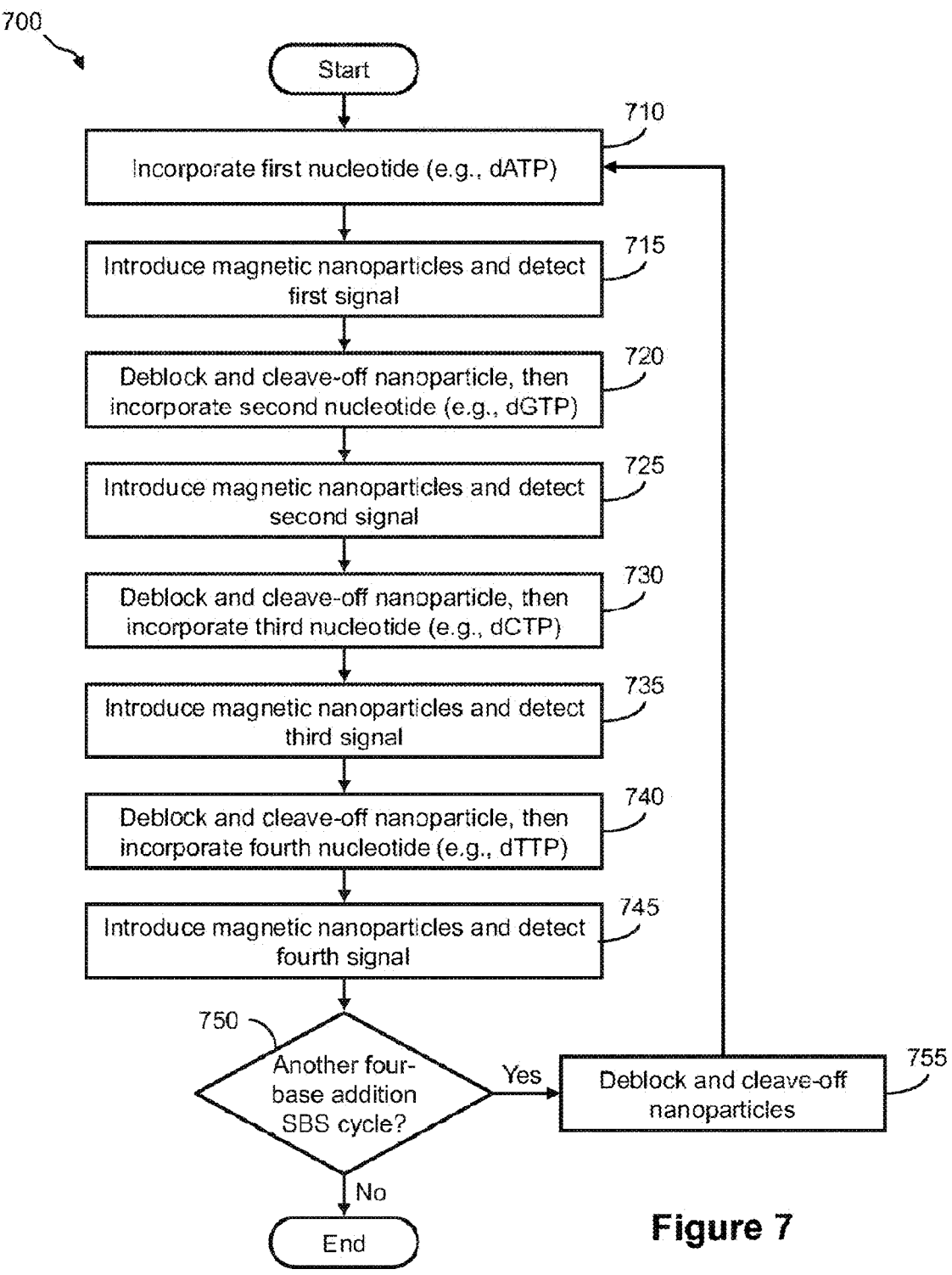
FIG. 7 illustrates a flow diagram of an example of a method of base determination in a magnetic biosensing SBS scheme using, for example, the flow cell shown in FIGS. 1A, 1B, and 4.

FIG. 7 illustrates a flow diagram of an example of a method 700 of base determination in a magnetic biosensing SBS scheme using, for example, flow cell 100 shown in FIGS. 1A, 1B, and 4. Method 700 uses successive addition of biotinylated nucleotides (i.e., one nucleotide at a time) and one type of streptavidin-coated (SA) magnetic nanoparticle for base determination. In one example, method 700 uses magnetic biosensing SBS scheme 500 of FIG. 5 and biotinylated nucleotide 520 of FIG. 6. Referring now to FIG. 7, method 700 includes, but is not limited to, the following steps.

At a step 710, a first biotinylated nucleotide 520 is incorporated into growing complementary DNA strands in a first base addition reaction of an SBS cycle. The first biotinylated nucleotide 520 may be delivered to the designated spaces having the template strands. For example, a solution containing the first biotinylated nucleotide 520 (e.g., biotinylated nucleotide 520a) is flowed into sequencing chamber 118 of flow cell 100 and through the designate spaces to allow the first biotinylated nucleotides 520 to extend the growing complementary strands. As another example, a droplet of a solution containing the first biotinylated nucleotides 520 may be delivered to each designated space using the droplet operations described herein. The droplet may occupy the designated space for a predetermined period of time to allow the first biotinylated nucleotides 520 to extend the growing complementary strands. In one example, the first nucleotide is biotinylated dATP.

At a step 715, SA magnetic nanoparticles are introduced into the flow cell. The SA magnetic nanoparticles may be delivered to the designated spaces having the template strands and a first signal may be detected. For example, a solution containing SA magnetic nanoparticles 525 may be flowed into the chamber 118 of flow cell 100. The SA magnetic nanoparticles 525 are permitted to be captured by the first biotinylated nucleotides 520. For example, the magnetic nanoparticles 525 may be captured via a biotin/streptavidin binding complex at the sites (clusters). As another example, a droplet of the solution may be delivered to each designated space using droplet operations described herein. The droplet may occupy the designated space for a predetermined period of time to permit the SA magnetic nanoparticles to attach to the labeled nucleotides. After the magnetic particles attach to the labeled nucleotides, a first signal may be detected. The signal may be a change in electrical resistance at the magnetically-responsive sensors. The change in electrical resistance may be caused by the magnetic particle(s) located within the designated spaces.

At a step 720, the magnetic particles may be removed from the labeled nucleotides. For example, the biotin/streptavidin magnetic nanoparticle complexes may be removed from the incorporated nucleotides 520 by cleavage of cleavable linker 620. After removal of biotin/streptavidin magnetic nanoparticle complexes, the signal is returned to background levels. Blocking group 625 of nucleotides 520 are removed by a deblocking reaction for subsequent incorporation of the next complimentary nucleotide.

The SBS sequencing is continued by a subsequent base addition reactions. In particular embodiments, second, third, and fourth base addition reactions may be conducted. For example, a solution containing a second biotinylated nucleotide 520 (e.g., biotinylated nucleotide 520*b*) is flowed into sequencing chamber 118 of flow cell 100. In one example, the second nucleotide is biotinylated dGTP.

At a step 725, SA magnetic nanoparticles are introduced into the flow cell and a second signal is detected. For example, magnetic nanoparticles 525 are captured via a biotin/streptavidin binding complex at the sites (clusters) with incorporation of G and a second signal is detected at associated magnetic sensors 130.

At a step 730, biotin/streptavidin magnetic nanoparticle complexes are removed from the incorporated nucleotides 520 by cleavage of cleavable linker 620. Blocking group 625 of nucleotides 520 are removed by a deblocking reaction for subsequent incorporation of the next complimentary nucleotide. The SBS cycle is continued by a third base addition reaction. For example, a solution containing a third biotinylated nucleotide 520 (e.g., biotinylated nucleotide 520*c*) is flowed into sequencing chamber 118 of flow cell 100. In one example, the third nucleotide is biotinylated dCTP.

At a step 735, SA magnetic nanoparticles are introduced into the flow cell and a third signal is detected. For example, magnetic nanoparticles 525 are captured via a biotin/streptavidin binding complex at all sites (clusters) with incorporation of C and a third signal is detected at associated magnetic sensors 130.

At a step 740, biotin/streptavidin magnetic nanoparticle complexes are removed from the incorporated nucleotides 520 by cleavage of cleavable linker 620. Blocking group 625 of nucleotides 520 are removed by a deblocking reaction for subsequent incorporation of the next complimentary nucleotide. The SBS cycle is continued by a fourth base addition reaction. For example, a solution containing a fourth biotinylated nucleotide 520 (e.g., biotinylated nucleotide 520*d*) is flowed into sequencing chamber 118 of flow cell 100. In one example, the third nucleotide is biotinylated dTTP.

At a step 745, SA magnetic nanoparticles are introduced into the flow cell and a fourth signal is detected. For example, magnetic nanoparticles 525 are captured via a biotin/streptavidin binding complex at all sites (clusters) with incorporation of T and a fourth signal is detected at associated magnetic sensors 130.

At a decision step 750, it is determined whether another four-base addition SBS cycle is desired. If another SBS cycle is desired, then method 700 proceeds to a step 755. If another SBS cycle is not desired, then method 700 ends.

At a step 755, biotin/streptavidin magnetic nanoparticle complexes are removed from the incorporated nucleotides 520 by cleavage of cleavable linker 620. Blocking group 625 of nucleotides 520 are removed by a deblocking reaction for subsequent incorporation of the next complimentary nucleotide. Method 700 returns to step 710.

In another example, a "2-label" magnetic biosensing SBS scheme uses hapten labeled nucleotides and two different types of functionalized magnetic nanoparticles. In this example, two fluidic/detection cycles are used for base discrimination in an SBS cycle.

Figure 8:
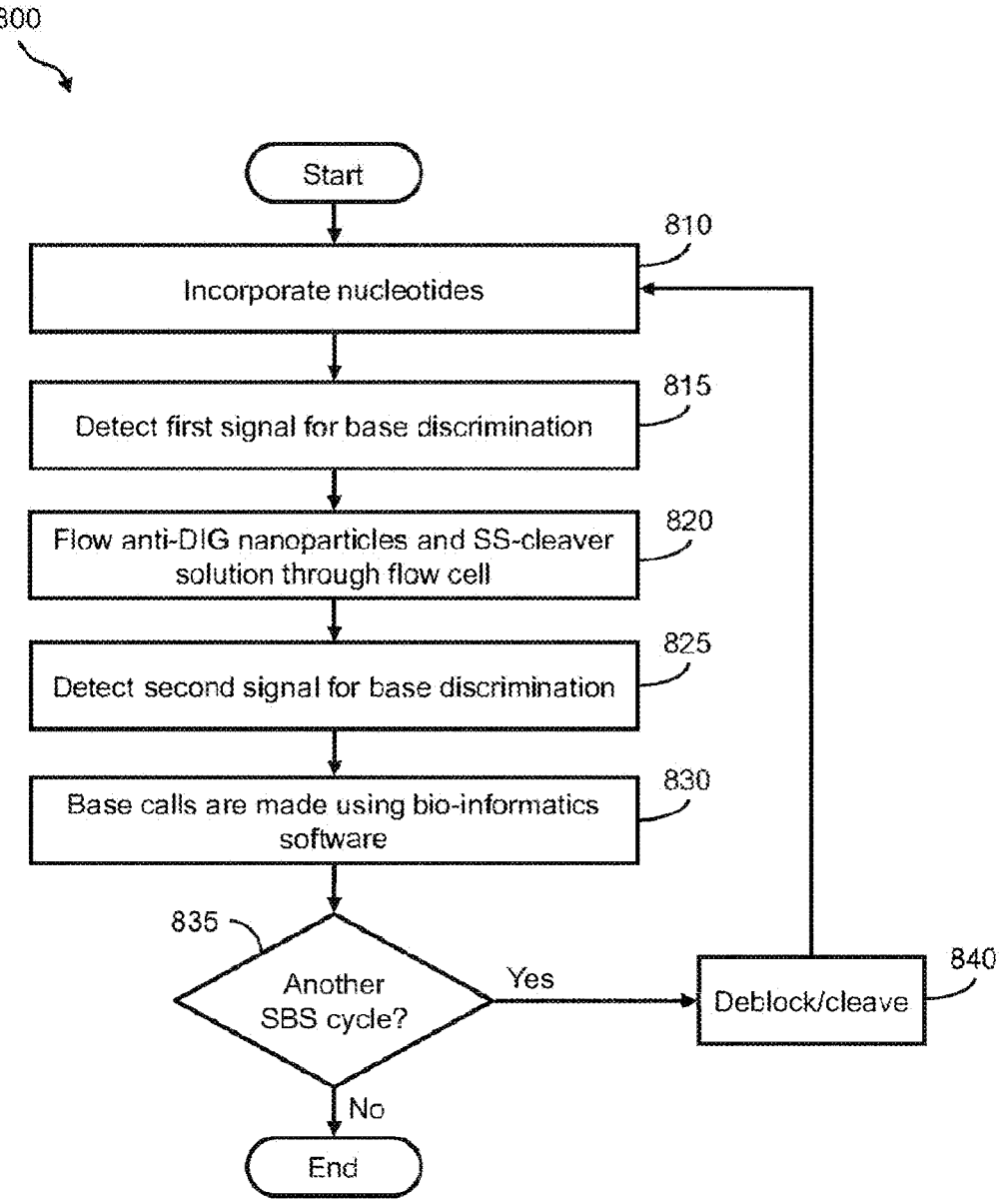
FIG. 8 illustrates a flow diagram of an example of a method of base discrimination in a "two-label" magnetic biosensing SBS scheme using, for example, the flow cell shown in FIGS. 1A, 1B, and 4.
Figure 9:
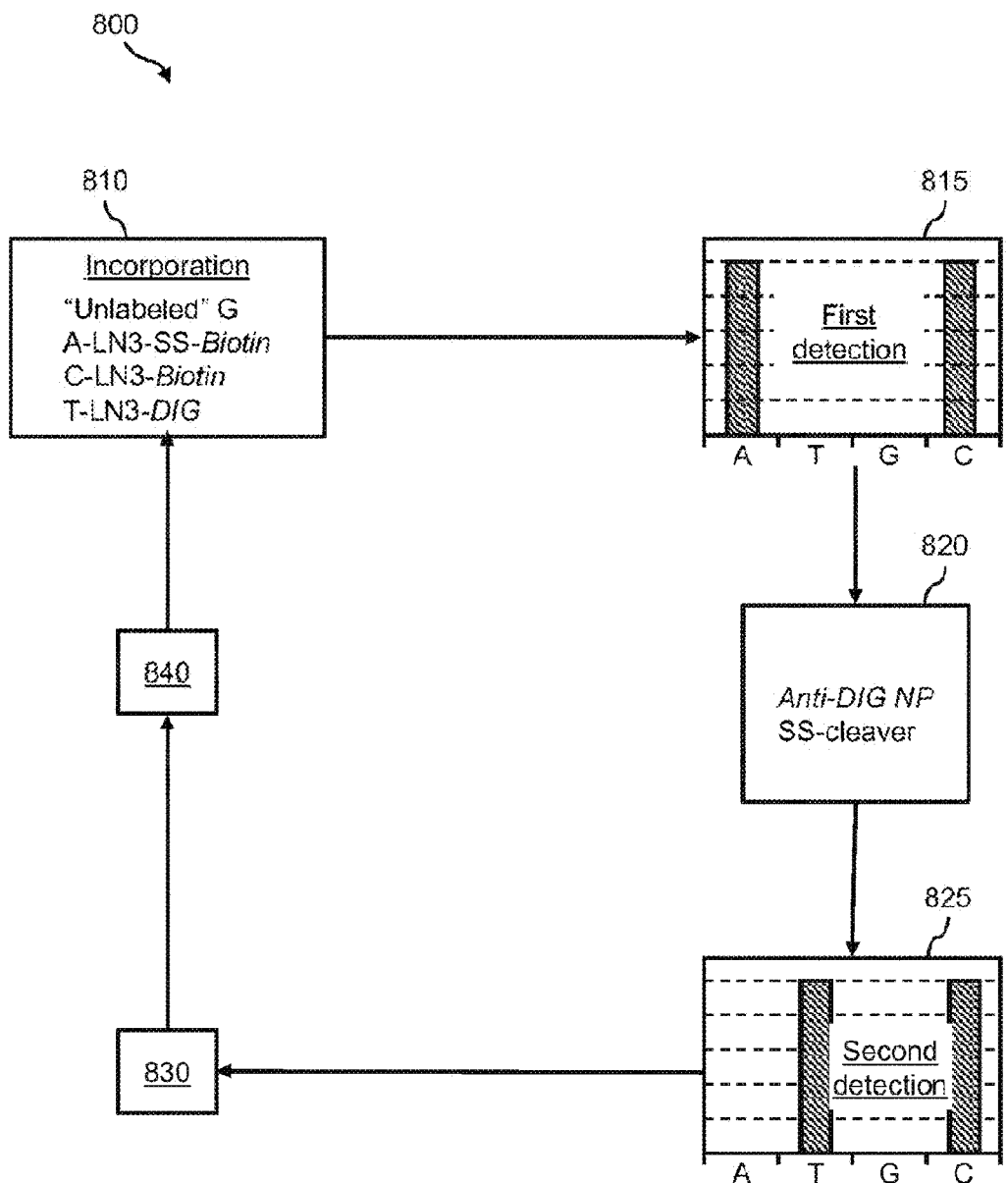
FIG. 9 illustrates a schematic diagram showing pictorially the steps of the method of FIG. 8.

FIG. 8 illustrates a flow diagram of an example of a method 800 of base discrimination in a "two-label" magnetic biosensing SBS scheme using, for example, flow cell 100 shown in FIGS. 1A, 1B, and 4. FIG. 9 illustrates a schematic diagram showing pictorially the steps of method 800 of FIG. 8. In one example, method 800 uses biotinylated A nucleotides with a cleavable disulfide (SS) bond (A-LN3-

SS-Biotin), biotinylated C nucleotides (C-LN3-Biotin), and streptavidin (SA) coated magnetic nanoparticles to detect incorporation of A and C, and digoxigenin (DIG)-labeled T nucleotides (T-LN3-DIG) and magnetic nanoparticles coated with an antibody (or antibody fragment) specific for DIG to detect incorporation of T. G nucleotides are not labeled for detection. Referring now to FIG. 8, method 800 includes, but is not limited to, the following steps.

At a step 810, nucleotides are incorporated into growing complementary strands in an SBS cycle. The nucleotide may be A-LN3-SS-Biotin, C-LN3-Biotin, T-LN3-Dig, or unlabeled G. This step is also shown pictorially in the schematic diagram of FIG. 9.

At a step 815, a first signal is detected of incorporated of A or C nucleotides. For example, using magnetic sensors 130 of flow cell 100, a first signal is detected for incorporated of A or C nucleotides. A solution of streptavidin (SA) coated magnetic nanoparticles is flowed through sequencing chamber 118 of flow cell 100 and biotin/streptavidin complexes are formed at the sites (clusters) with incorporation of A or C. This step is also shown pictorially in the schematic diagram of FIG. 9.

At a step 820, a solution that includes anti-DIG coated magnetic nanoparticles (Anti-DIG NP) and a disulfide (SS)-cleaver is flowed through sequencing chamber 118 of flow cell 100. Complex formation between incorporated T-LN3-DIG nucleotides and anti-DIG NP selectively identifies sites (clusters) with incorporation of T. The SS-cleaver cleaves the disulfide bond in incorporated A-LN3-SS-Biotin nucleotides and effectively removes the biotin/streptavidin complexes from A nucleotides thereby eliminating signals that may be generated from those sites. This step is also shown pictorially in the schematic diagram of FIG. 9.

At a step 825, a second signal is detected for incorporation of T nucleotides. For example, using magnetic sensors 130 of flow cell 100, a second signal is detected for incorporated T nucleotides A signal from incorporation of a C nucleotide is also detected. This step is also shown pictorially in the schematic diagram of FIG. 9.

At a step 830, base calls are made using bio-informatics software. In this example, incorporation of A and C are detected in the first signal detection. Incorporation of T and C are detected in the second signal detection. Because SS-cleaver was flowed through the flow cell at step 820, the signal from incorporated A nucleotides is absent in the second signal detection. Incorporation of G is determined based on the lack of a signal in at the first and second detections. This step is also shown pictorially in the schematic diagram of FIG. 9.

At a decision step 835, it is determined whether another cycle of SBS is desired. If another SBS cycle is desired, then method 800 proceeds to a step 840. If another SBS cycle is not desired, then method 800 ends.

At a step 840, a deblocking reaction and a cleaving reaction are performed. The deblocking reaction is used to remove a blocking group on the incorporated nucleotides for the next nucleotide addition in the next SBS cycle. The cleaving reaction is used to remove bound magnetic nanoparticles from the incorporated nucleotides and return the signal to background levels. Method 800 returns to step 810. This step is also shown pictorially in the schematic diagram of FIG. 9.

In other embodiments, the magnetic particles may already be attached to one or more of the nucleotides when the nucleotides are added to the complementary strand. For example, the nucleotides that flow through the sequencing chamber for being added to the complementary strand may be A-LN3-SS-MagneticParticle, C-LN3-Biotin, T-LN3-MagneticParticle, and unlabeled G. In such embodiments, it is not necessary to attach the magnetic particles to the nucleotides A and T after the nucleotides have been added to the complementary strand. Instead, a first signal from incorporated A and T nucleotides may be detected. For example, using magnetic sensors 130 of flow cell 100, a first signal is detected for incorporated of A or T nucleotides.

Subsequently, a solution that includes a disulfide (SS)-cleaver may be flowed through sequencing chamber 118 of flow cell 100. The SS-cleaver cleaves the disulfide bond in incorporated A-LN3-SS-MagneticParticle nucleotides thereby eliminating signals that may be generated from those sites. A solution that include magnetic particles for attaching to C-LN3-Biotin may also be flowed through the sequencing chamber 118.

A second signal may then be detected for incorporation of T nucleotides and C nucleotides. For example, using magnetic sensors 130 of flow cell 100, a second signal is detected for incorporated T nucleotides and incorporated C nucleotides.

After the first and second signals are detected, base calls may be made using bio-informatics software. In this example, incorporation of A and T are detected in the first signal detection. Incorporation of T and C are detected in the second signal detection. Because SS-cleaver was flowed through the flow cell, the signal from incorporated A nucleotides is absent in the second signal detection. Incorporation of G is determined based on the lack of a signal in at the first and second detections.

As described above, if no further cycles are necessary, a deblocking reaction and a cleaving reaction may be performed. The deblocking reaction is used to remove a blocking group on the incorporated nucleotides for the next nucleotide addition in the next SBS cycle. The cleaving reaction is used to remove bound magnetic nanoparticles from the incorporated nucleotides and return the signal to background levels.

In yet another example, a "four-label" magnetic biosensing SBS scheme uses modified nucleotides and different magnetic magnitudes for base discrimination. In one example, different magnetic magnitudes are provided by capture of one or more magnetic nanoparticles at sites of nucleotide incorporation. For example, dATP is modified to capture one magnetic nanoparticle, dTTP is modified to capture two magnetic nanoparticles, dCTP is modified to capture three magnetic nanoparticles, and dGTP is modified to capture four magnetic nanoparticles. The magnitude of the signal detected is then a function of the base that was incorporated.

In one example, a modified nucleotide comprising a thiol (SH) group is used to capture a single molecule magnet (SMM) that has only one reactive group (e.g., maleimide-modified SMM). The nucleotide may comprise one, two, three, or four thiol groups and capture one, two, three or four maleimide-modified SMMs, respectively. Aldehyde (CHO)-aminooxy (or hydrazine) is an example of another chemistry pair that may be used in a "four-label" magnetic biosensing SBS scheme using modified nucleotides and SMMs.

In another example, up to four orthogonal chemistries are used for nucleotide modification such that a single nucleotide may recruit from 1 to 4 magnetically responsive beads. An example of a "four-label" magnetic biosensing SBS scheme is described in more detail with reference to FIG. 1.

In another embodiment, nanoparticles comprising different paramagnetic materials may be used in a magnetic biosensing SBS scheme. For example, paramagnetic materials are selected such that each type of nanoparticle has a different response to the frequency of an applied external magnetic field. Some paramagnetic particles may have tunable resonant frequencies and would not become paramagnetic, or follow the applied external field well, at non-optimal frequencies. Because each type of nanoparticle responds to the applied external field differently, each type of nanoparticle may be used for base discrimination. Nanoparticles with comprising different paramagnetic materials may be used, for example, in "one-label", "two-label", or "four-label" magnetic biosensing SBS schemes.

In another embodiment, the diameter/volume of the nanoparticles for each label type can be different. For example, 10 nm diameter vs. 50 nm diameter results in about a 100-fold volume difference, and about a 25-fold surface area difference (signal is affected by both volume and surface area).

Figure 10:
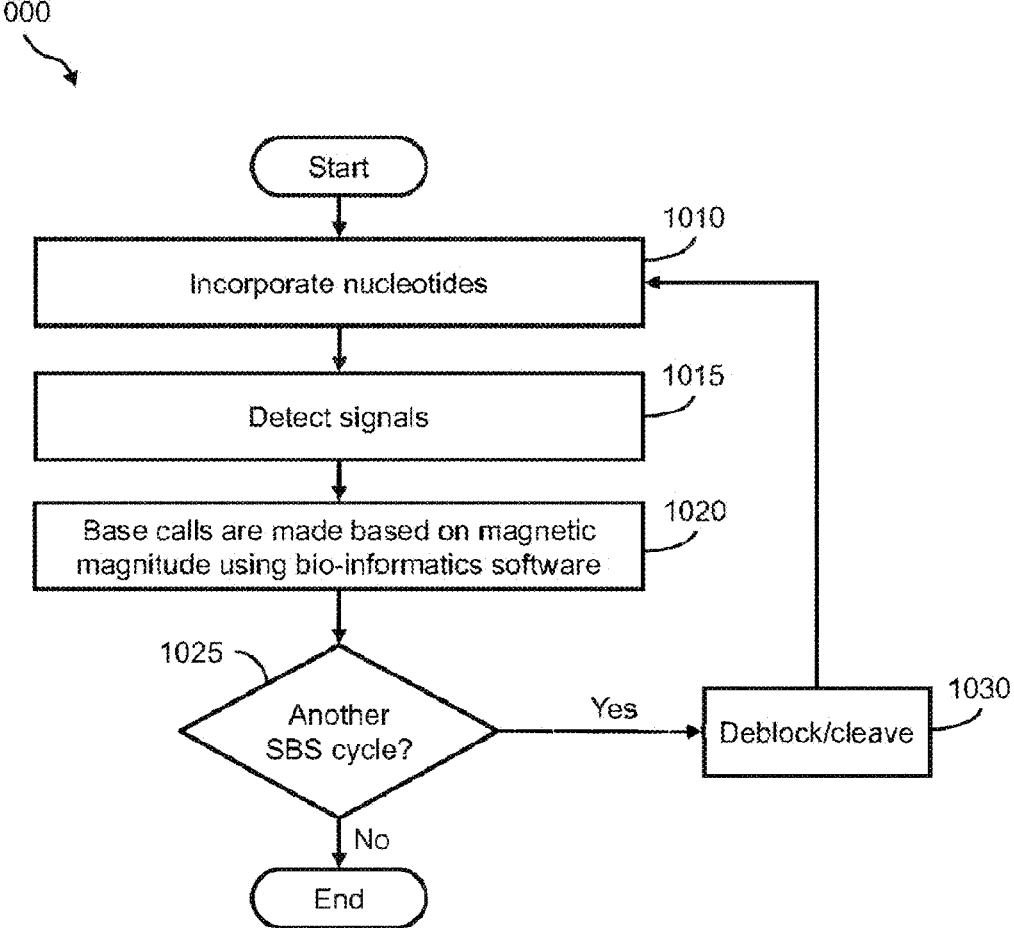
FIG. 10 illustrates a flow diagram of an example of a method of base discrimination in a "four-label" magnetic biosensing SBS scheme using, for example, the flow cell shown in FIGS. 1A, 1B, and 4.

FIG. 10 illustrates a flow diagram of an example of a method 1000 of base discrimination in a "four-label" magnetic biosensing SBS scheme using, for example, flow cell 100 shown in FIGS. 1A, 1B, and 4. In this example, dATP is modified to capture one magnetic nanoparticle (or SMM), dTTP is modified to capture two magnetic nanoparticles (or SMMs), dCTP is modified to capture three magnetic nanoparticles (or SMMs), and dGTP is modified to capture four magnetic nanoparticles (or SMMs). Method 1000 includes, but is not limited to, the following steps.

At a step 1010, nucleotides are incorporated into growing complementary strands in an SBS cycle. The nucleotide may be A, T, C, or G.

At a step 1015, signals are detected for incorporated nucleotides. For example, using magnetic sensors 130 of flow cell 100, signals are detected for incorporated nucleotides. A solution of functionalized magnetic nanoparticles is flowed through sequencing chamber 118 of flow cell 100 and nucleotide/nanoparticle complexes are formed at all sites (clusters) with incorporation A, T, C, or G.

At a step 1020, base calls are made based on magnetic magnitude using bio-informatics software. In this example, incorporation of A is detected by a signal of a first magnitude, incorporation of T is detected by a signal of a second magnitude, incorporation of C is detected by a signal of a third magnitude, and incorporation of G is detected by a signal of a fourth magnitude.

At a decision step 1025, it is determined whether another cycle of SBS is desired. If another SBS cycle is desired, then method 1000 proceeds to a step 1030. If another SBS cycle is not desired, then method 1000 ends.

At a step 1030, a deblocking reaction and a cleaving reaction are performed. The deblocking reaction is used to remove a blocking group on the incorporated nucleotides for the next nucleotide addition in the next SBS cycle. The cleaving reaction is used to remove bound magnetic nanoparticles from the incorporated nucleotides and return the signal to background levels. Method 1000 returns to step 1010.

In an alternative embodiment of FIG. 10, a SBS method may be carried out using single pot reactions. In this example, the template strands may be immobilized to a surface or the polymerase may be immobilized to the surface. For the single pot reaction, reversibly-blocked nucleotides having magnetic particles attached thereto are simultaneously provided with a deblocking agent. For those embodiments in which the template strands are immobilized to the surface, the polymerase may be provided with the nucleotides and the deblocking agent.

At step 1010, the nucleotides may be incorporated into growing complementary strands. At a step 1015, signals are detected for incorporated nucleotides. In particular, as the nucleotide is added to the complementary strand by the polymerase, the magnetically-responsive sensors may detect a change in the electrical resistance that is caused by the presence of the magnetic particles. The magnetic particles may provide a constant external magnetic field or, alternatively, may be induced by applying an external stimuli.

At step 1020, base calls are made based on the detected changes in the electrical resistance. For instance, incorporation of A is detected by a signal of a first magnitude, incorporation of T is detected by a signal of a second magnitude, incorporation of C is detected by a signal of a third magnitude, and incorporation of G is detected by a signal of a fourth magnitude.

At a step 1030, a deblocking reaction and a cleaving reaction are performed. The deblocking reaction is used to remove a blocking group on the incorporated nucleotides for the next nucleotide addition in the next SBS cycle. The cleaving reaction is used to remove bound magnetic nanoparticles from the incorporated nucleotides and return the signal to background levels.

In single-pot embodiments, the reactants do not include 3' blocking agents or deblocking agents. The electrical resistance for each magnetically-responsive sensor may be monitored to identify incorporation events in real time. Such embodiments may be particularly applicable for single-molecule protocols.

Because the above embodiment illustrates a single pot reaction, it should be understood that the steps 1010, 1015, and 1030 may occur at different times for different template strands. In some embodiments, one or more of the steps may be controlled. For example, step 1030 may be performed by external stimuli that is applied by the system. Moreover, step 1030 may occur in real time. Alternatively, step 1030 may occur after a plurality of incorporation events or after the SBS sequencing is complete. In another alternative embodiments, such as single-molecule protocols, step 1030 does not occur.

1.3 Single-Molecule Magnet SBS

In another embodiment, nucleotides labeled with single-molecule magnets (SMMs) are used for base discrimination in a magnetic biosensing SBS scheme. SMMs are a class of metal-organic compounds that show superparamagnetic behavior, e.g., they are magnetic only in in the presence of an external magnetic field. Magnetic properties or states of some SMMs may be altered by applying an external stimuli. In one example, the magnetic state of a SMM may be switched using light. For example, one frequency of light may be used to switch an SMM ON and another frequency of light may be used to switch the SMM OFF. Because the magnetic state can be switched, the signal-to-noise (S/N) ratio may be improved via repeated sampling. One or more SMMs may be selected such that the size of the SMM is compatible with nucleotide chemistry. In one example, an SMM may be about 1.2 nm in size.

SMMs that may have their respective magnetic properties or states changed by applying external stimuli are described in Feng et al., "Tristability in a Light-Actuated Single-Molecule Magnet," *J. Am. Chem. Soc.,* 2013, 135 (42), pp 15880-15884; Mathonière et al., "Photoinduced Single-Molecule Magnet Properties in a Four-Coordinate Iron(II) Spin Crossover Complex," *J. Am. Chem. Soc.,* 2013, 135 (51), pp 19083-19086; Christou et al. "Single-molecule magnets," *Mrs Bulletin* 25.11 (2000): 66-71; "Single-molecule magnets and related phenomena," Volume 122 of Structure and bonding Single-molecule magnets and related phenomena, editors Richard Winpenny and Guillem Aromi, Springer (2006); Sato, "Switchable molecular magnets," Proc Jpn Acad Ser B Phys Biol Sci. 2012 Jun. 11; 88(6): 213-225; Sato (2003) "Optically switchable molecular solids: Photoinduced spin-crossover, photochromism, and photoinduced magnetization." Acc. Chem. Res. 36, 692-700, Sato et al. (2007) "Control of magnetic properties through external stimuli." Angew. Chem. Int. Ed. 46, 2152-2187. Each of these reference is incorporated herein by reference in its entirety.

In one example, a nucleotide labeled with an SMM has essentially the same structure as nucleotide 520 of FIG. 6. In this example, biotin label 610 is replaced by one or more SMMs.

In one example, SMMs are used in a "four-label" magnetic biosensing SBS scheme. In this example, each nucleotide (A, G, C, and T) is labeled with a SMM that is sensitive to a different set of ON/OFF light frequencies. For example, A is labeled with a first SMM that is sensitive to a first set of ON/OFF light frequencies, G is labeled with a second SMM that is sensitive to a second set of ON/OFF light frequencies, C is labeled with a third SMM that is sensitive to a third set of ON/OFF light frequencies, and T is labeled with a fourth SMM that is sensitive to a fourth set of ON/OFF light frequencies.

Figure 11:
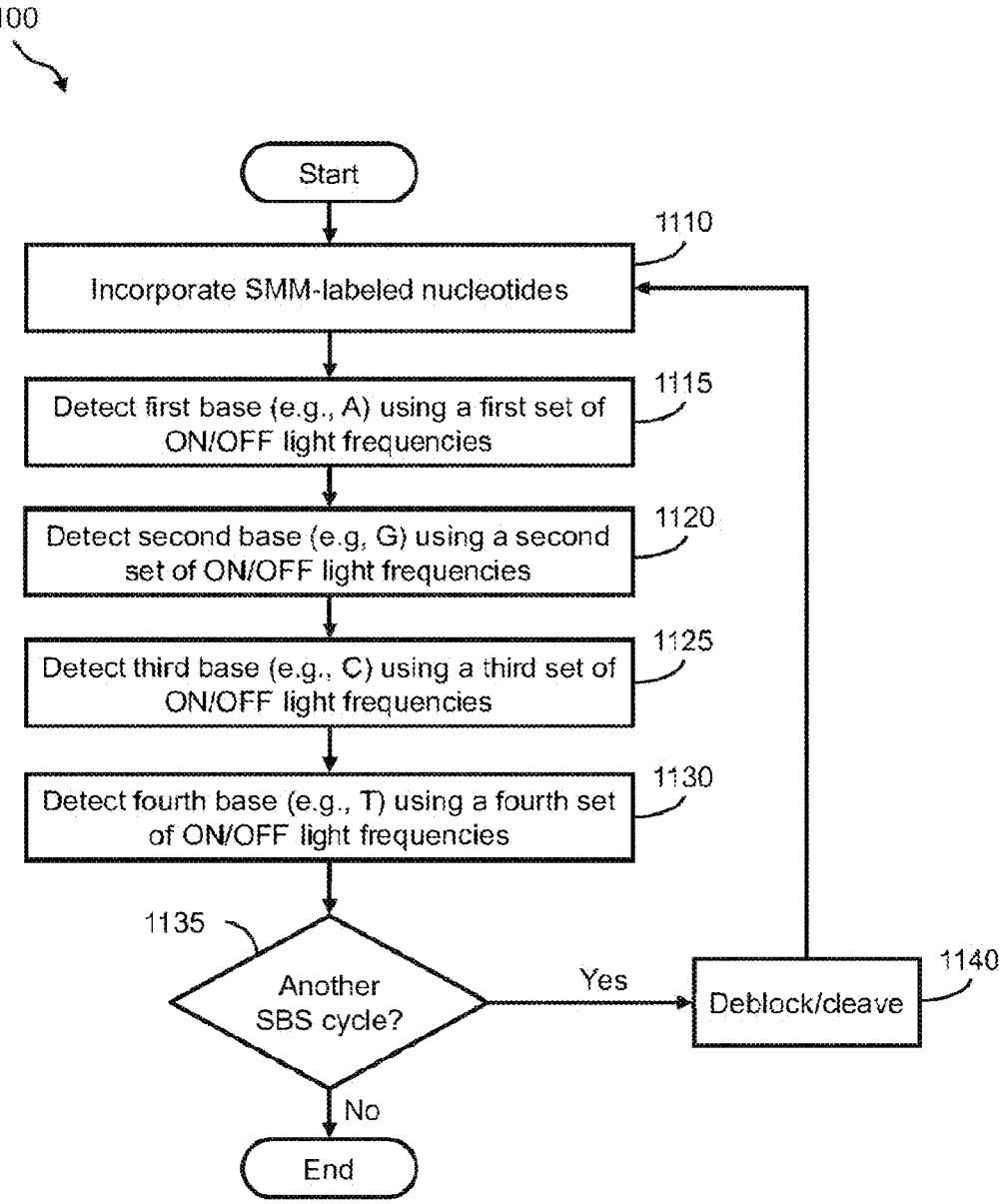
FIG. 11 illustrates a flow diagram of an example of a method of base discrimination in a "four-label" magnetic biosensing SBS scheme using SMM-labeled nucleotides.

FIG. 11 illustrates a flow diagram of an example of a method 1100 of base discrimination in a "four-label" magnetic biosensing SBS scheme using SMM-labeled nucleotides. In this example, A is labeled with a first SMM that is sensitive to a first set of ON/OFF light frequencies, G is labeled with a second SMM that is sensitive to a second set of ON/OFF light frequencies, C is labeled with a third SMM that is sensitive to a third set of ON/OFF light frequencies, and T is labeled with a fourth SMM that is sensitive to a fourth set of ON/OFF light frequencies.

At a step 1110, SMM-labeled nucleotides are incorporated into growing complementary strands in an SBS cycle. The nucleotide may be A, G, C, or T.

At a step 1115, a first set of ON/OFF light frequencies is used to detect incorporation of a first nucleotide, e.g., A. For example, the "ON" frequency is used to switch on the SMM label of the incorporated A nucleotide and a signal is detected. The "OFF" light frequency is used to switch OFF the SMM and return the signal to background levels.

At a step 1120, a second set of ON/OFF light frequencies is used to detect incorporation of a second nucleotide, e.g., G. For example, the "ON" frequency is used to switch on the SMM label of the incorporated G nucleotide and a signal is detected. The "OFF" light frequency is used to switch OFF the SMM and return the signal to background levels.

At a step 1125, a third set of ON/OFF light frequencies is used to detect incorporation of a third nucleotide, e.g., C. For example, the "ON" frequency is used to switch on the SMM label of the incorporated C nucleotide and a signal is detected. The "OFF" light frequency is used to switch OFF the SMM and return the signal to background levels.

At a step 1130, a fourth set of ON/OFF light frequencies is used to detect incorporation of a fourth nucleotide, e.g., T. For example, the "ON" frequency is used to switch on the SMM label of the incorporated T nucleotide and a signal is detected. The "OFF" light frequency is used to switch OFF the SMM and return the signal to background levels.

At a decision step 1135, it is determined whether another cycle of SBS is desired. If another SBS cycle is desired, then method 1100 proceeds to a step 1140. If another SBS cycle is not desired, then method 1100 ends.

At a step 1140, a deblocking reaction and a cleaving reaction are performed. The deblocking reaction is used to remove a blocking group on the incorporated nucleotides for the next nucleotide addition in the next SBS cycle. The cleaving reaction is used to remove the SMM label from the incorporated nucleotides. Method 1100 returns to step 1110.

In another example, SMM-labeled nucleotides may be used in a "four-label" magnetic biosensing SBS scheme using different magnetic magnitudes for base discrimination. In one example, dATP is labeled with one SMM, dGTP is labeled with two SMMs, dCTP is labeled with three SMMs, and dTTP is labeled with four SMMs. The magnitude of the signal detected is then a function of the base that was incorporated.

Figure 12:
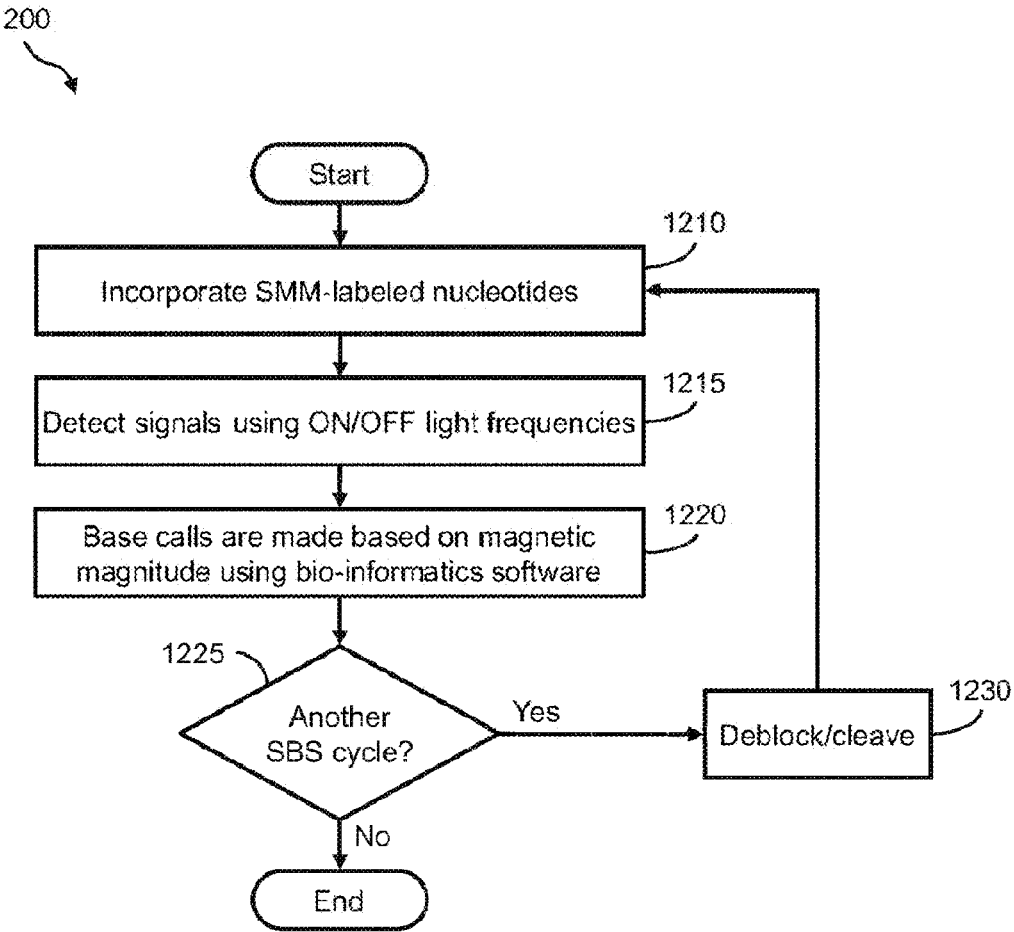
FIG. 12 illustrates a flow diagram of an example of a method of base discrimination in a "four-label" magnetic biosensing SBS scheme using SMM-labeled nucleotides with different magnetic magnitudes for base discrimination.

FIG. 12 illustrates a flow diagram of an example of a method 1200 of base discrimination in a "four-label" magnetic biosensing SBS scheme using SMM-labeled nucleotides with different magnetic magnitudes for base discrimination. In this example, a single type of SMM is used, but each nucleotide is labeled with a different number of SMMs. For example, dATP is labeled with one SMM, dGTP is labeled with two SMMs, dCTP is labeled with three SMMs, and dTTP is labeled with four SMMs. Method 1200 uses, for example, flow cell 100 shown in FIGS. 1A, 1B, and 4. Method 1200 includes, but is not limited to, the following steps.

At a step 1210, SMM-labeled nucleotides are incorporated into growing complementary strands in an SBS cycle. The nucleotide may be A, G, C, or T.

At a step 1215, signals are detected for the incorporated nucleotides using, for example, magnetic sensors 130 of flow cell 100. A first frequency of light is used to switch ON the SMM labels and a signal is detected at all sites (clusters) with incorporation of A, G, C, or T. A second frequency of light is used to switch OFF the SMMs and return the signal to background levels.

At a step 1220, base calls are made based on magnetic magnitude using bio-informatics software. In this example, incorporation of A is detected by a signal of a first magnitude, incorporation of G is detected by a signal of a second magnitude, incorporation of C is detected by a signal of a third magnitude, and incorporation of T is detected by a signal of a fourth magnitude.

At a decision step 1225, it is determined whether another cycle of SBS is desired. If another SBS cycle is desired, then method 1200 proceeds to a step 1230. If another SBS cycle is not desired, then method 1200 ends.

At a step 1230, a deblocking reaction and a cleaving reaction are performed. The deblocking reaction is used to remove a blocking group on the incorporated nucleotides for the next nucleotide addition in the next SBS cycle. The cleaving reaction is used to remove SMM labels from the incorporated nucleotides and return the signal to background levels. Method 1200 returns to step 1210.

1.4 Functionalized DNA Polymerase in Magnetic Biosensing SBS

In yet another embodiment, unlabeled nucleotides and a functionalized DNA polymerase are used for base discrimination in a magnetic biosensing SBS scheme. In one example, DNA polymerase is tagged with a single-molecule magnet and the nucleotides are engineered to have different rates of incorporation during SBS. For example, A is modified to have a first incorporation rate, G is modified to have a second incorporation rate, C is modified to have a third incorporation rate, and T is modified to have a fourth incorporation rate. Because the incorporation rate is different for each nucleotide, the time DNA polymerase is associated with an incorporation site (cluster) is then a function of the base that was incorporated. An example of nucleotide incorporation rates is shown in Table 1.

TABLE 1

| Nucleotide incorporation rates | |
| --- | --- |
| Nucleotide | Incorporation rate (ms) |
| dATP | 10 |
| dGTP | 100 |
| dCTP | 500 |
| dTTP | 1,000 |

In one example, the 3' hydroxyl (OH) group of the engineered nucleotides are unprotected by a blocking group. In another example, the 3' hydroxyl (OH) group of the engineered nucleotides are protected by a blocking group.

Figure 13:
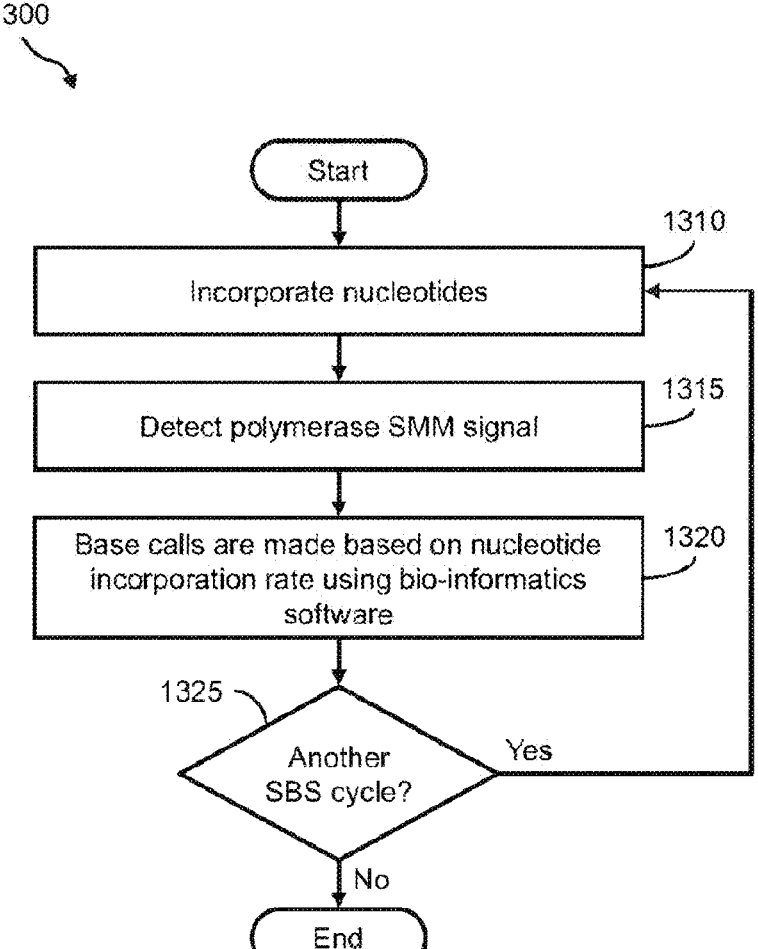
FIG. 13 illustrates a flow diagram of an example of a method of base discrimination in a magnetic biosensing SBS scheme using an SMM-tagged DNA polymerase and nucleotides with different rates of incorporation.

In one or more embodiments, such as those described with respect to FIG. 13, an SBS protocol may include attaching magnetic particles to polymerase. The magnetic particle may be, for example, magnetic nanoparticles or SMMs. More specifically, in one or more embodiments, the SBS method may include providing a detection apparatus that includes an array of magnetically-responsive sensors. The detection apparatus may be similar to those described herein. Each of the magnetically-responsive sensors may be located proximate to a respective designated space to detect an external magnetic field therefrom. The detection apparatus may also include a plurality of nucleic acid template strands located within corresponding designated spaces. The template strands may be immobilized to a surface. Alternatively, the template strands may be confined within a designated volume, such as a well or gel matrix.

The method may also include conducting a plurality of SBS cycles to grow a complementary strand by adding nucleotides along each template strand using polymerase. The polymerase may have corresponding magnetic particles attached thereto that provide respective magnetic fields. When the polymerase adds nucleotides to the template strands, the polymerase may be located within the designated space. As such, the sensors may be capable of detecting the magnetic fields from the magnetic particles attached to the polymerase.

Each SBS cycle may include detecting changes in electrical resistance at the magnetically-responsive sensors. More specifically, the detected changes may be caused by the presence of the magnetic particles at the designated spaces when the polymerase adds the nucleotides. The method may also include determining sequences of the complementary strands as described herein.

FIG. 13 illustrates a flow diagram of an example of a method 1300 of base discrimination in a magnetic biosensing SBS scheme using an SMM-tagged DNA polymerase and nucleotides with different rates of incorporation. In this example, the nucleotides are unblocked and have incorporations rates as shown in Table 1.

At a step 1310, nucleotides are incorporated into growing complementary strands in an SBS cycle. The nucleotide may be A, G, C, or T. In one example, four nucleotides that have the same incorporation time are flowed separately. Then monitor for the association of the polymerase incorporating (which is probably from about 30 ms to about 100 ins). In another example, four nucleotides that have very different incorporation times are all flowed at the same time.

At a step 1315, signals from the polymerase SMM tag are detected. For example, using magnetic sensors 130 of flow cell 100, a signal from SMM-tagged DNA polymerase is detected at each site of nucleotide incorporation. A first frequency of light is used to switch ON the polymerase SMM tag and a signal is detected at all sites (clusters) with incorporation of A, G, C, or T A second frequency of light is used to switch OFF the polymerase SMM tag and return the signal to background levels.

At a step 1320, base calls are made based on nucleotide incorporation rate using bio-informatics software. In this example, incorporation of A is detected by a signal of a first duration (e.g., about 10 ms), incorporation of G is detected by a signal of a second duration (e.g., about 100 ms), incorporation of C is detected by a signal of a third duration (e.g., about 500 ms), and incorporation of T is detected by a signal of a fourth duration (e.g., about 1,000 ms).

At a decision step 1325, it is determined whether another cycle of SBS is desired. If another SBS cycle is desired, then method returns to step 1310. If another SBS cycle is not desired, then method 1300 ends.

Embodiments of the present application, however, are not limited to the embodiments shown in FIGS. 1A through 13. Magnetic sensors (e.g., GMR-based and/or TMR-based sensors) can be used in combination with other structures, mechanisms, and/or systems for supporting a magnetic biosensing SBS scheme; examples of which are shown and described hereinbelow with reference to FIGS. 14A through 18.

Figure 14A:
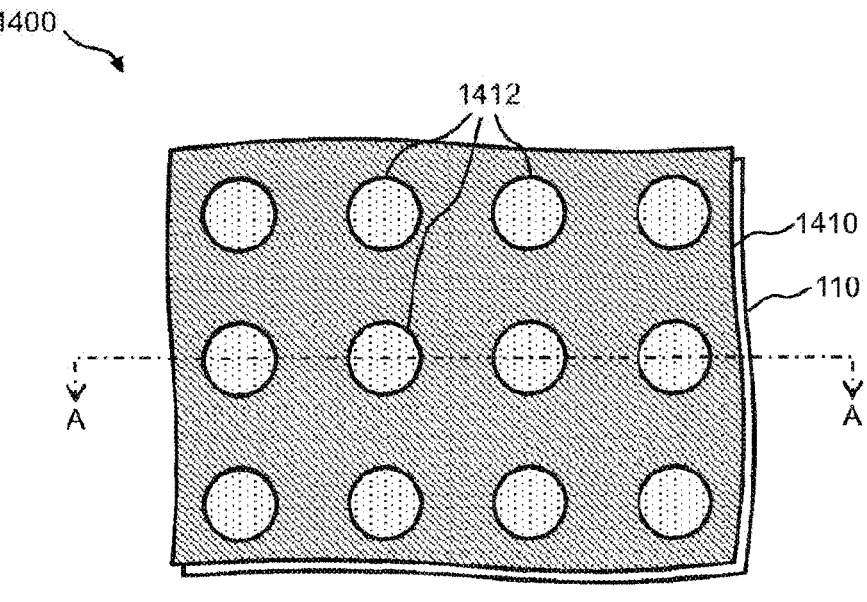
FIG. 14A illustrates a plan view of the magnetic sensor array in combination with an example of a semi-hydrophobic region in a flow cell or droplet actuator.
Figure 14B:
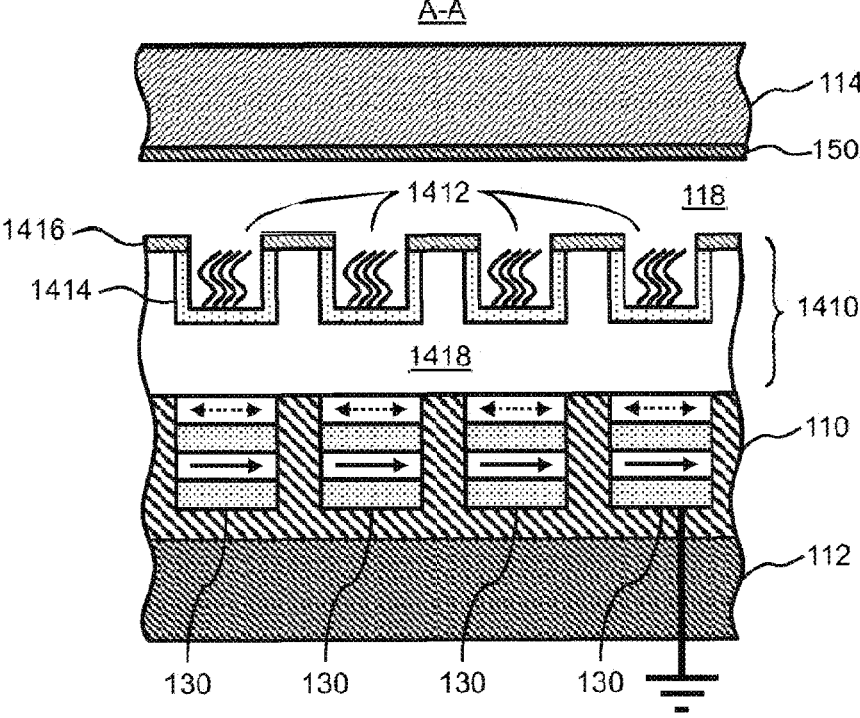
FIG. 14B illustrates a cross-sectional view of the magnetic sensor array of FIG. 14A.

FIGS. 14A and 14B illustrate a plan view and a cross-sectional view, respectively, of magnetic sensor array 110 in combination with an example of a semi-hydrophobic region in a flow cell or droplet actuator 1400. Flow cell or droplet actuator 1400 includes magnetic sensor array 110 atop PCB 112 in relation to top substrate 114 and conductive layer 150, as described with reference to flow cell 100 of FIGS. 1A, 1B, and 4.

Flow cell or droplet actuator 1400 further includes a semi-hydrophobic region 1410 atop magnetic sensor array 110. In this example, semi-hydrophobic region 1410 comprises a substrate 1418. Substrate 1418 can be, for example, a glass substrate or a CMOS substrate. In one example, substrate 1418 is a silicon dioxide (SiO2) substrate. Semi-hydrophobic region 1410 further comprises a plurality of nanowells 1412 that are patterned into substrate 1418. The inside of nanowells 1412 is coated with a hydrophilic layer 1414 and thereby forming hydrophilic nanowells 1412. The surface of substrate 1418 that is outside of nanowells 1412 is coated with a hydrophobic layer 1416. Further, oligonucleotide primers 142 are provided inside each of nanowells 1412.

Hydrophilic layer 1414 inside of nanowells 1412 can be any hydrophilic material suitable for conducting surface-based chemistry in a droplet actuator. In one example, hydrophilic layer 1414 is a polyacrylamide gel coating, such as a mixture of norbornene (or norbornylene or norcamphene) and Poly(N-(5-azidoacetamidylpentyl) acrylamide-co-acrylamide), also known as PAZAM In another example, hydrophilic layer 1414 comprises Poly(N-(5-azidoacet-amidylpentyl) acrylamide-co-acrylamide-co-acrylonitrile), also known as PAZAM-PAN. In some embodiments, the PAZAM and/or PAZAM-PAN can be modified to be thermally responsive, thereby forming a thermo-responsive polyacrylamide gel. More details about PAZAM can be found with reference to George et al., U.S. patent application Ser. No. 13/784,368, entitled "Polymer Coatings," filed on Mar. 4, 2013, the entire disclosure of which is incorporated herein by reference.

Hydrophobic layer 1416 fills the interstitial space between nanowells 1412. Hydrophobic layer 1416 can be any hydrophobic material suitable for conducting surface-based chemistry in a droplet actuator. In one example, hydrophobic layer 1416 is fluoro-octyl-trichloro-silane (FOTS), known formally as (tridecafluoro-1,1,2,2-tetrahydrooctyl) trichlo-rosilane. In another example, hydrophobic layer 1416 is a fluorinated photoresist (i.e., a hydrophobic flouropolymer), such as the ALX2010 photo dielectric, available from Asahi Glass Co., Ltd. (Tokyo, Japan), aka AGC.

In flow cell or droplet actuator 1400, nanowells 1412 are arranged in rows and columns having positions that substantially correspond to the rows and columns of magnetic sensors 130 of magnetic sensor array 110. Each nanowell 1412 has a certain depth and diameter. In one example, nanowells 1412 have a depth of about 350 nm and a diameter of about 400 nm. In another example, nanowells 1412 have a depth of about 350 nm and a diameter of about 500 nm.

Figure 15A:
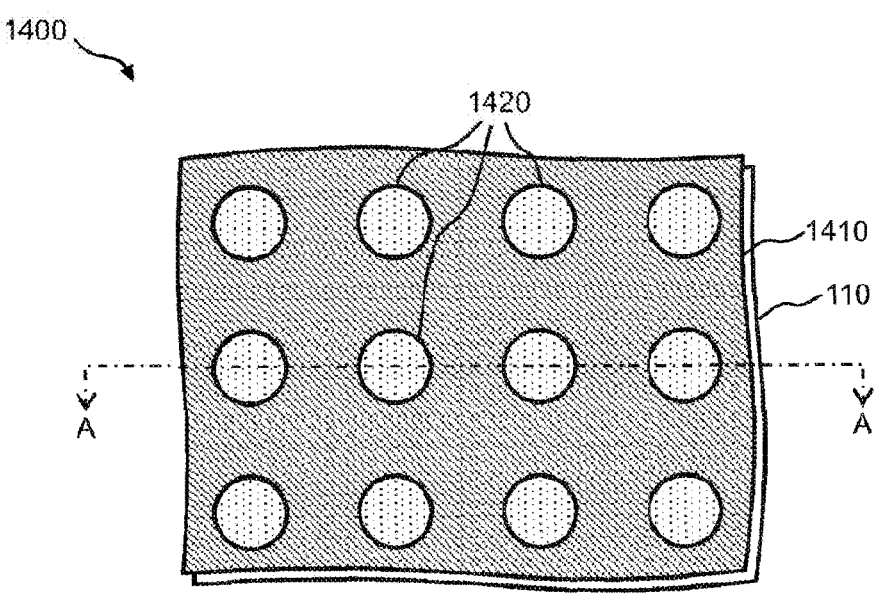
FIG. 15A illustrates a plan view of the magnetic sensor array in combination with another example of the semi-hydrophobic region in a flow cell or droplet actuator.
Figure 15B:
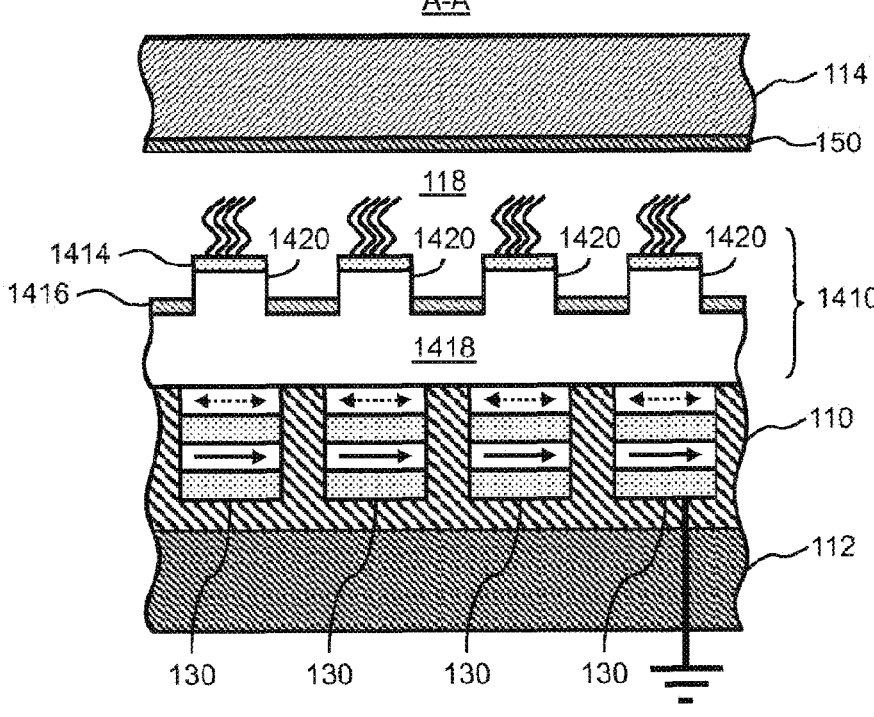
FIG. 15B illustrates a cross-sectional view of the magnetic sensor array of FIG. 15A.

FIGS. 15A and 15B illustrate a plan view and a cross-sectional view, respectively, of magnetic sensor array 110 in combination with another example of semi-hydrophobic region 1410 in flow cell or droplet actuator 1400. In this example, the polarity of hydrophilic layer 1414 and hydrophobic layer 1416 is reversed. Namely, rather than hydrophilic layer 1414 being in a well with respect to the plane of hydrophobic layer 1416, hydrophilic layer 1414 is on a pedestal with respect to the plane of hydrophobic layer 1416. For example, nanowells 1412 of semi-hydrophobic region 1410 described in FIGS. 14A and 14B are replaced with pedestals 1420. Atop pedestals 1420 is hydrophilic layer 1414 and oligonucleotide primers 142, thereby forming hydrophilic pedestals 1420.

In this example of flow cell or droplet actuator 1400, hydrophilic pedestals 1420 are arranged in rows and columns having positions that substantially correspond to the rows and columns of magnetic sensors 130 of magnetic sensor array 110.

Figure 16A:
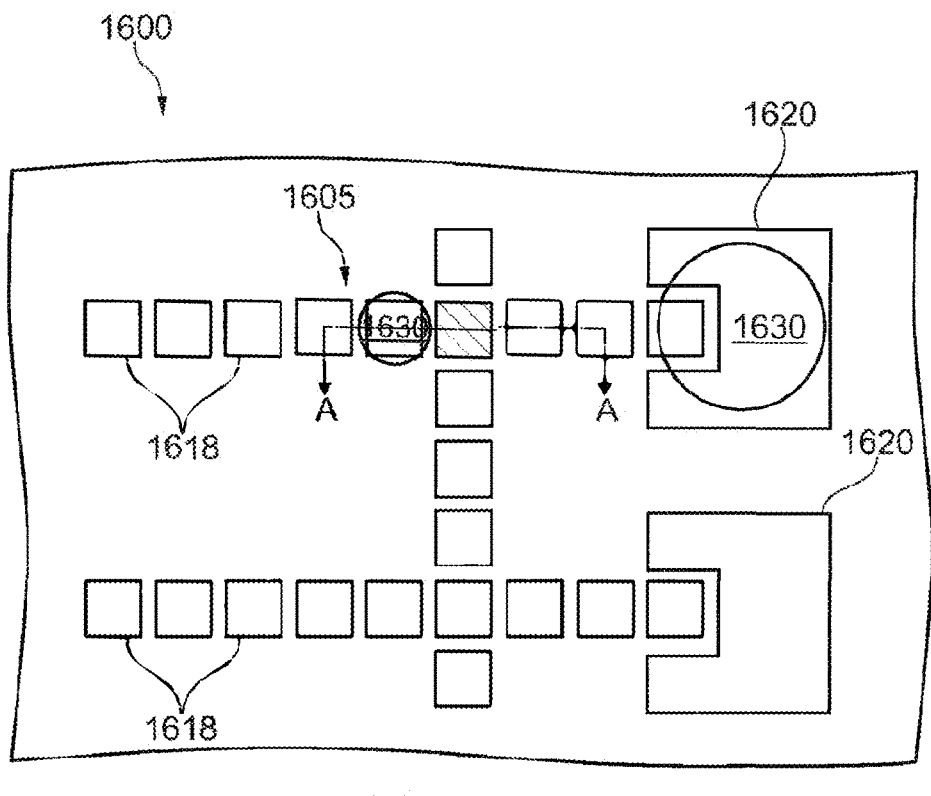
FIG. 16A illustrates a plan view of a portion of a droplet actuator that includes the magnetic sensor array for supporting, for example, a magnetic biosensing SBS scheme.
Figure 16B:
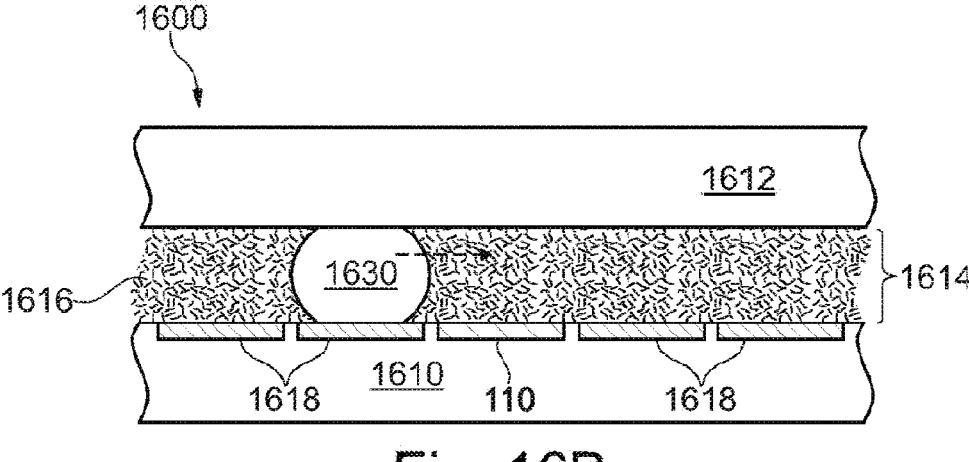
FIG. 16B illustrates a cross-sectional view of the droplet actuator of FIG. 16B.

FIGS. 16A and 16B illustrate a plan view and a cross-sectional view, respectively, of a portion of a droplet actuator 1600 that includes magnetic sensor array 110 for supporting, for example, a magnetic biosensing SBS scheme. Droplet actuator 1600 includes a bottom substrate 1610 and a top substrate 1612 that are separated by a droplet operations gap 1614. Droplet operations gap 1614 contains filler fluid 1616. The filler fluid 1616 is, for example, low-viscosity oil, such as silicone oil or hexadecane filler fluid. Bottom substrate 1610 includes an electrode arrangement 1605 that comprises, for example, various lines of droplet operations electrodes 1618 (e.g., electrowetting electrodes) feeding various reservoir electrodes 1620. Droplet operations are conducted atop droplet operations electrodes 1618 on a droplet operations surface.

A magnetic sensor array 110 that is sized about the same as the droplet operations electrodes 1618 may be provided in one or more of the lines droplet operations electrodes 1618, as shown. In this example, portions of top substrate 1612 near droplet operations electrodes 1618 may include a ground reference plane or electrode (not shown), while portions of top substrate 1612 near magnetic sensor array 110 may include a Vdd reference plane or electrode (not shown). A droplet 1630 (e.g., a sample or reagent droplet) may be transported via droplet operations along droplet operations electrodes 1618 and to magnetic sensor array 110, at which certain magnetic biosensing operations may occur, such as those described with reference to FIGS. 5 through 13.

In some embodiments, one or more of the magnetically-responsive sensors may be movable with respect to a sample substrate that has the biological or chemical sample thereon. For example, a sequencing-by-synthesis (SBS) system may include a read head having an arm and a magnetically-responsive sensor attached to the arm. The magnetically-responsive sensor may include at least one of a giant magnetoresistance (GMR) sensor or a tunnel magnetoresistance (TMR) sensor.

The system may also include a sample substrate having a substrate surface. The substrate surface is configured to have a plurality of nucleic acid template strands located within designated spaces along the substrate surface. At least one of the read head and the sample substrate are configured to move with respect to the other to position the magnetically-responsive sensor proximate to the designated spaces in an operative relationship. More specifically, the magnetically-responsive sensor is positioned such that external magnetic fields generated by magnetic particles may be detected. The system also includes a readout circuit that is communicatively coupled to the magnetically-responsive sensor. The readout circuit is configured to transmit signals that correspond to an electrical resistance of the magnetically-responsive sensor when positioned at one of the designated spaces. The readout circuit may be similar to the readout circuit 106 (FIG. 1).

Figure 17:
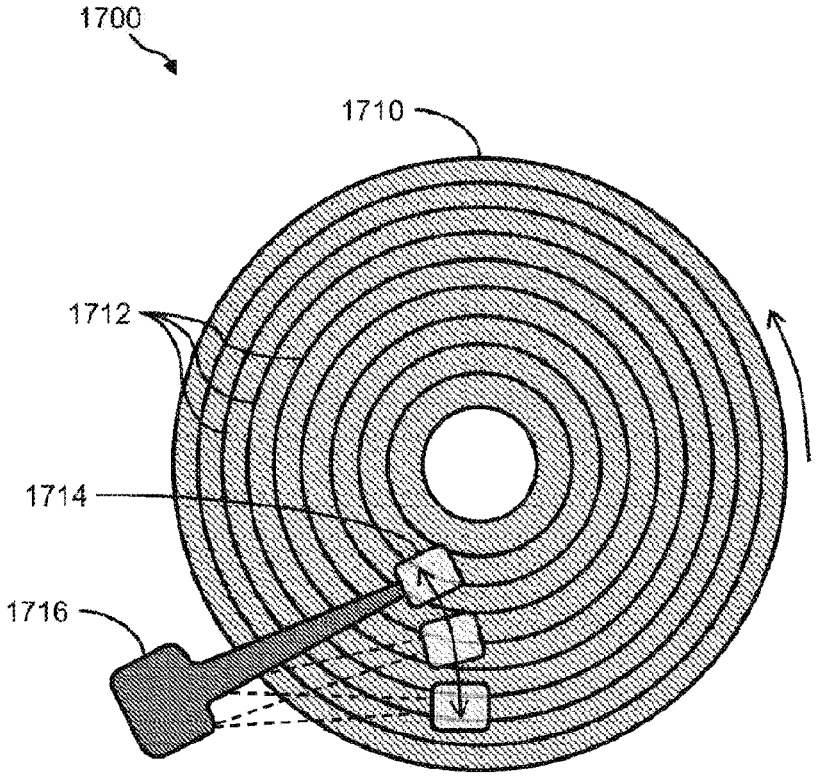
FIG. 17 illustrates a plan view of a rotating disc-based instrument in which one movable magnetic sensor is provided for supporting, for example, a magnetic biosensing SBS scheme.

FIG. 17 illustrates a plan view of such a system More specifically, FIG. 17 illustrates a rotating disc-based instrument 1700 in which one movable magnetic sensor is provided for supporting, for example, a magnetic biosensing SBS scheme. Rotating disc-based instrument 1700 comprises a disc substrate (or sample substrate) 1710, which may be, for example, a plastic compact disc (CD) substrate. A set of concentric tracks (or grooves) 1712 are provided in the surface of disc substrate 1710. Rotating disc-based instrument 1700 further includes a magnetic read head 1714 on a movable arm 1716. Namely, there is a pivot point on one end of movable arm 1716 and magnetic read head 1714 is on the opposite end of movable arm 1716. Magnetic read head 1714 comprises one magnetic sensor, such as a GMR-based and/or TMR-based sensor, such as one magnetic sensor 130 as described with reference to FIGS. 1A through 4. It is contemplated, however, that the magnetic read head may include more than one magnetically-responsive sensor.

In rotating disc-based instrument 1700, disc substrate 1710 is rotatable using standard CD technology. Concentric tracks 1712 can be populated with a plurality of, for example, oligonucleotide primers 142 (not shown). Again, oligonucleotide primers 142 are capture primers on which single-stranded DNA fragments are hybridized and may be amplified to form clonal DNA template clusters for SBS.

In one example, there are about 10 concentric tracks 1712 with about 100 clusters/track, which is about 1000 clusters/disc. By spinning disc substrate 1710, reagents can be dispensed and distributed onto concentric tracks 1712 using centripetal force. Then, using the one magnetic sensor of magnetic read head 1714, magnetic biosensing operations can occur, for example, at about 10 RPM. The distance between the magnetic read head 1714 and magnetic particles incorporated or captured during an SBS nucleotide incorporation reaction must be suitably small for good detection. Aspects of rotating disc-based instrument 1700 include an inexpensive substrate (e.g., CD substrate), savings on microfluidic pumping overhead, fast fluidics, and the sensor(s) can be re-used because the disc is functionalized, suitable for performing SBS Although the instrument 1700 utilizes a rotating disc it is contemplated that other types of movement may be used. For example, the sample substrate may include a slide. The slide and/or the read head may be movable in order to position the magnetically-responsive sensors relative to the designated spaces. For example, the slide and/or the read head may be operably coupled to a motor.

As compared with conventional optical detection systems in SBS applications, the presently disclosed devices for and methods of SBS using a magnetic sensor array for supporting a magnetic biosensing SBS scheme provide certain advantages, such as, but not limited to:

(1) Small size—a magnetic sensor array occupies a much smaller area than optomechanical devices. For example, 1 gigabit magnetic sensor array device can occupy an area of about 13 cm×3 cm×0.1 cm, whereas optomechanics can occupy an area of about 5.08 cm×5.08 cm×5.08 cm;

(2) Simplicity and low cost—a magnetic biosensing system requires only a controller, whereas optical detection systems require translation stages, optical components, and controller;

(3) Ruggedness—a magnetic biosensing system has no delicate moving parts, whereas optical detection systems have delicate moving parts; and (4) Speed—a magnetic biosensing scheme can be about 6.5× faster than direct CMOS imaging and about 100× faster than XTen optomechanics. For example, magnetic biosensing can support 3.2 Gbytes/s data rate; 1.6 billion transfers per second per I/O, which is 1.6 billion clusters per second.

Figure 18A:
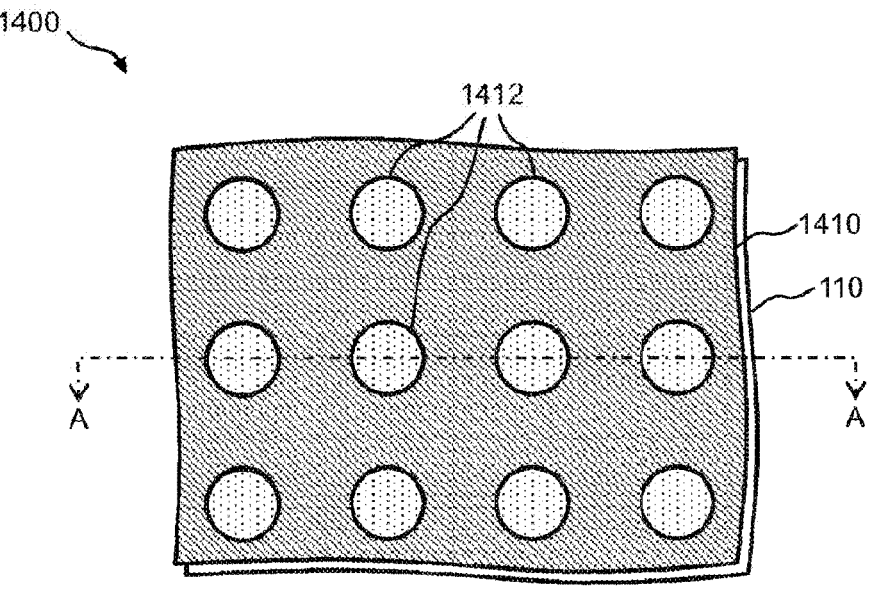
FIG. 18A illustrates a plan view of the magnetic sensor array in combination with an embodiment in which polymerase is immobilized to designated areas.
Figure 18B:
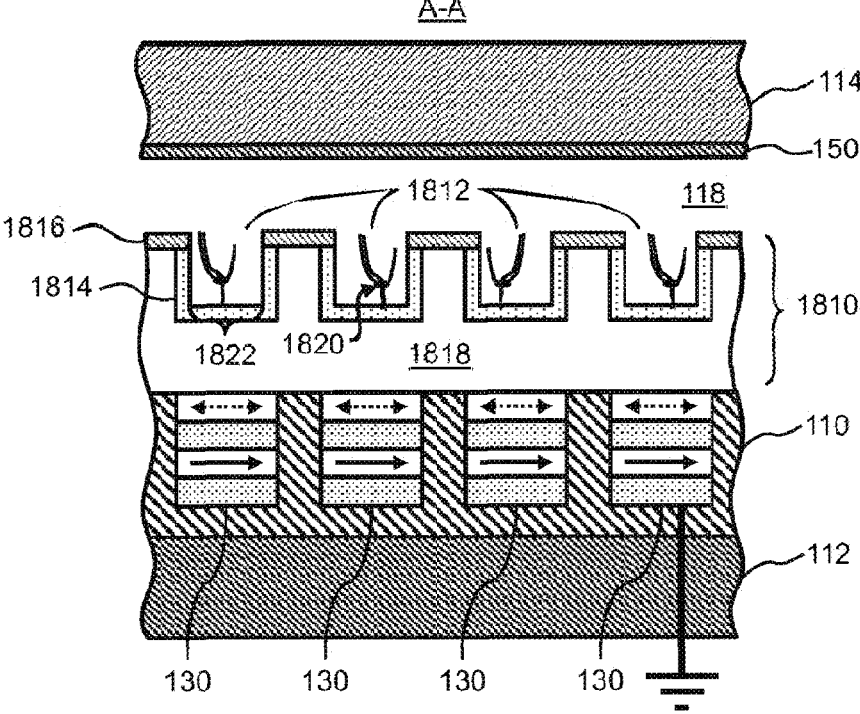
FIG. 18B illustrates a cross-sectional view illustrate a plan view and a cross-sectional view, respectively, of the magnetic sensor array of FIG. 18A.

FIGS. 18A and 18B illustrate a plan view and a cross-sectional view, respectively, of magnetic sensor array 110 in a flow cell or droplet actuator 1800. Flow cell or droplet actuator 1800 includes magnetic sensor array 110 atop PCB 112 in relation to top substrate 114 and conductive layer 150, as described with reference to flow cell 100 of FIGS. 1A, 1B, and 4.

Flow cell or droplet actuator 1800 further includes a semi-hydrophobic region 1410 atop magnetic sensor array 110. In this example, semi-hydrophobic region 1810 comprises a substrate 1818. Substrate 1818 can be, for example, a glass substrate or a CMOS substrate. In one example, substrate 1818 is a silicon dioxide (SiO2) substrate. Semi-hydrophobic region 1810 further comprises a plurality of wells 1812 (e.g., nanowells) that are patterned into substrate 1818. The inside of nanowells 1812 is coated with a hydrophilic layer 1814 and thereby forming hydrophilic nanowells 1812. The surface of substrate 1818 that is outside of nanowells 1812 is coated with a hydrophobic layer 1816. Further, oligonucleotide primers 142 are provided inside each of nanowells 1812.

Hydrophilic layer 1814 inside of nanowells 1812 can be any hydrophilic material suitable for conducting surface-based chemistry in a droplet actuator. In one example, hydrophilic layer 1814 is a polyacrylamide gel coating, such as a mixture of norbornene (or norbornylene or norcamphene) and Poly(N-(5-azidoacetamidylpentyl) acrylamide-co-acrylamide), also known as PAZAM. In another example, hydrophilic layer 1814 comprises Poly(N-(5-azidoacetamidylpentyl) acrylamide-co-acrylamide-co-acrylonitrile), also known as PAZAM-PAN. In some embodiments, the PAZAM and/or PAZAM-PAN can be modified to be thermally responsive, thereby forming a thermo-responsive polyacrylamide gel. More details about PAZAM can be found with reference to George et al., U.S. patent application Ser. No. 13/784,368, entitled "Polymer Coatings," filed on Mar. 4, 2013, the entire disclosure of which is incorporated herein by reference.

Hydrophobic layer 1816 fills the interstitial space between nanowells 1812. Hydrophobic layer 1816 can be any hydrophobic material suitable for conducting surface-based chemistry in a droplet actuator. In one example, hydrophobic layer 1816 is fluoro-octyl-trichloro-silane (FOTS), known formally as (tridecafluoro-1,1,2,2-tetrahydrooctyl) trichlorosilane. In another example, hydrophobic layer 1816 is a fluorinated photoresist (i.e., a hydrophobic flouropolymer), such as the ALX2010 photo dielectric, available from Asahi Glass Co., Ltd. (Tokyo, Japan), aka AGC.

In flow cell or droplet actuator 1800, nanowells 1812 are arranged in an array having positions that substantially correspond to the array 110 of magnetic sensors 130. As shown in FIG. 18B, each of the nanowells may have a single polymerase 1820 that is immobilized to a designated area 1822 within the nanowell 1812. The polymerase 1820 may be immobilized to the designated area 1822 using a linker, such as those described above. Each of the polymerase 1820 is configured to capture a template strand having a primer attached thereto. In FIG. 18B, the SBS protocol is partially complete.

With the polymerase 1820 immobilized to the surface, embodiments may conduct the various protocols described above in which the nucleotides are labelled with magnetic particles. For example, the processes that are described above with respect to FIGS. 7-12 may be performed with the polymerase immobilized to the surface. As described herein, the magnetically-responsive sensors 130 may experience a change in electrical resistance as the magnetic particle attached to the nucleotide is added to the complementary strand. For each cycle, embodiments may deliver one nucleotide at a time such that four separate sub-cycles must be performed. Alternatively, embodiments may simultaneously deliver two or more nucleotides at a time. In other embodiments, however, the SBS protocol may be carried with single pot reactions.

Although the above example was described with the polymerase being immobilized to a surface in a well, it is contemplated that the polymerase may be selectively located along a planar surface.

Figure 19:
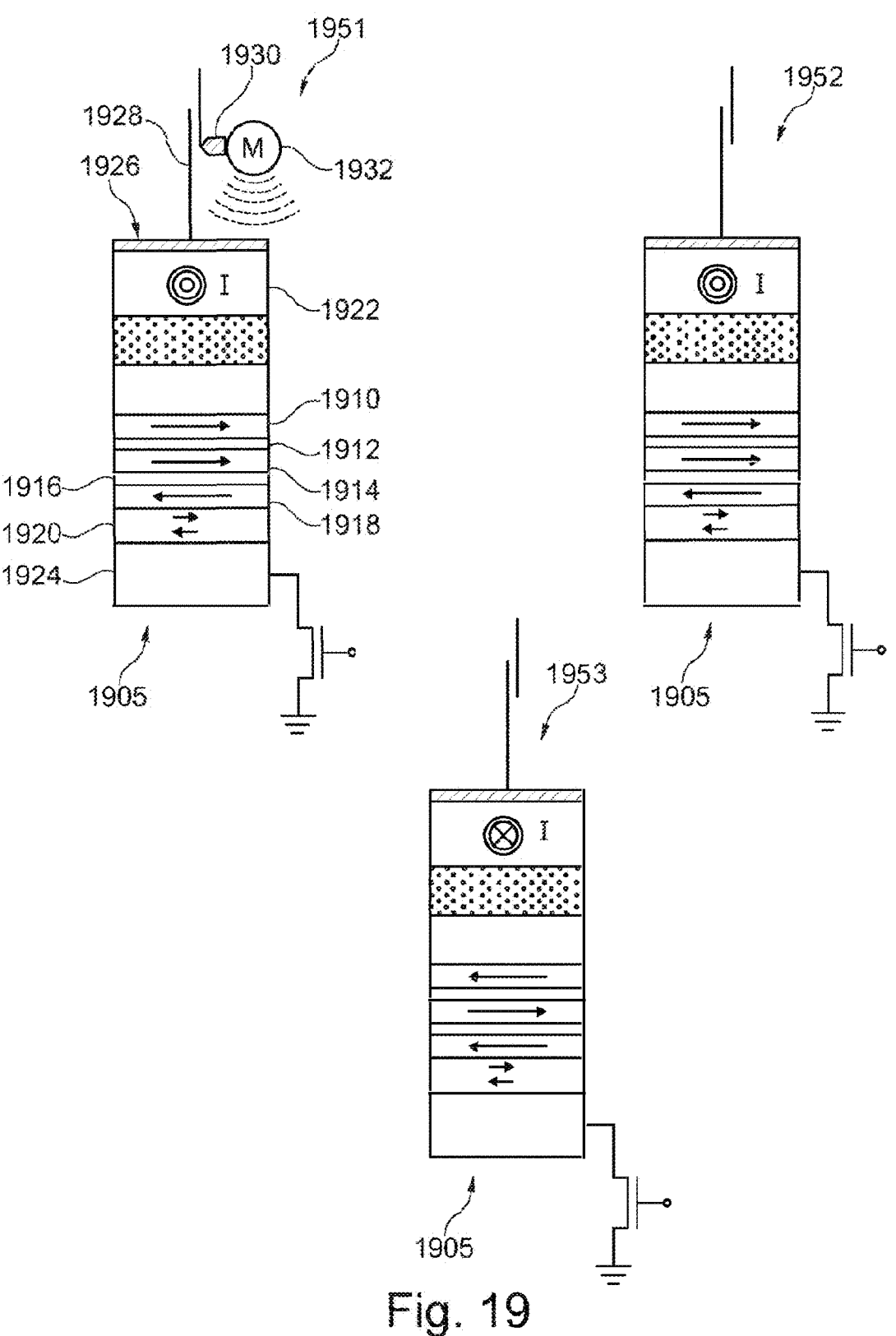
FIG. 19 illustrates a magnetically-responsive sensor in accordance with an embodiment.

Referring now to FIG. 19, a TMR device 1905 is shown at three different stages 1951, 1952, 1953 of an SBS protocol. The TMR device 1905 may constitute a magnetically-responsive sensor that may be part of a sensor array incorporated by a flow cell and/or a droplet actuator. The TMR device 1905 includes a first ferromagnetic layer 1910 (or storage layer), a nonmagnetic layer 1912, and a second ferromagnetic layer 1914. The nonmagnetic layer 1912 includes a thin insulating layer, such as $Al_2O_3$. As described above, when the first and second ferromagnetic layers 1910, 1914 are separated by the nonmagnetic layer 1912, electrical resistance of the multilayer in the perpendicular direction to the film changes depending on the orientations of the magnetizations of ferromagnetic layers 1910, 1914 because of spin dependent electron tunneling between the two ferromagnetic layers 1910, 1914. Also shown, the TMR device 1905 includes a separation layer 1916 of Ru, a flux compensation layer 1918, and an antiferromagnetic layer 1920. The TMR device 1905 is electrically coupled to and positioned between a write line (e.g., conductive trace) 1922 and a read line 1924.

As described above, when the directions of the magnetizations of the two ferromagnetic layers 1910, 1914 are opposite (as shown at the third stage 1953), the electron with opposite spin orientation with respect to the magnetization of the ferromagnetic layer cannot be tunneled. Then the tunneling electron current becomes smaller (i.e., higher resistance) compared to the case for the same directions of the magnetizations. When the directions of the magnetizations of the two ferromagnetic layers 1910, 1914 are the same (as shown in the first and second stages 1951, 1952), the possibility of electron tunneling between the two ferromagnetic layers through the insulator layer becomes larger, resulting in larger tunneling current (i.e., lower resistance).

Embodiments may carry out one or more of the methods described herein. For example, prior to the first stage 1951, template strands 1928 may be immobilized to a designated area of a substrate surface 1926 and primers attached thereto. During the first stage 1951, nucleotides 1930 may be incorporated into the complementary strand and, subsequently, magnetic particles 1932 may be provided that attach to the incorporated nucleotides 1930. Alternatively, the nucleotides 1930 may have magnetic particles 1932 attached thereto as the nucleotides 1930 are added to the complementary strand.

The magnetic particles 1932 may have a magnetic property that is capable of switching the first ferromagnetic layer 1910 such that the first ferromagnetic layer 1910 maintains its magnetization after the magnetic particle 1932 is removed as shown at the second stage 1952. More specifically, the magnetization is not transient, but permanent until the magnetization is changed by the write line 1922. This operation may be similar to the operation of non-volatile memory. In such embodiments, the TMR device 1905 may be read at designated times and for a designated time period through the read line 1924. In such embodiments, the TMR device 1905 may be capable of achieving a higher signal-to-noise ratio than TMR devices that do not have storage layers that maintain their magnetic states. After the TMR device 1905 is read, the write line 1922 may have electrical current flow therethrough to change the magnetization of the first ferromagnetic layer 1910. The SBS protocol may then repeat another SBS cycle.

The foregoing detailed description of embodiments refers to the accompanying drawings, which illustrate specific embodiments of the present disclosure. Other embodiments having different structures and operations do not depart from the scope of the present disclosure. It will be understood that various details may be changed without departing from the scope. Furthermore, the foregoing description is for the purpose of illustration only, and not for the purpose of limitation.

The following claims recite certain embodiments of the present application. The language of the claims is hereby incorporated into the Detailed Description.

What is claimed:

1. A method for determining a sequence of a nucleic acid template hybridized to a complementary strand, the method comprising:

using a polymerase coupled to a magnetically-responsive sensor to capture the nucleic acid template hybridized to the complementary strand;

contacting the polymerase and the captured nucleic acid template hybridized to the complementary strand with a first fluid comprising a first nucleotide;

using the polymerase to incorporate the first nucleotide into the complementary strand based on the sequence of the nucleic acid template;

contacting the polymerase and the captured nucleic acid template hybridized to the complementary strand, including the incorporated first nucleotide, with a second fluid comprising a first magnetic particle;

using the incorporated first nucleotide to capture the first magnetic particle from the second fluid;

detecting the captured first magnetic particle via a first change in electrical resistance at the magnetically-responsive sensor; and using the first change in electrical resistance to identify the incorporated first nucleotide.

2. The method of claim 1, wherein the first nucleotide is coupled to a first functional group, the first magnetic particle is coupled to a second functional group, and the first nucleotide captures the first magnetic particle by coupling the first functional group to the second functional group.

3. The method of claim 2, wherein the second functional group comprises biotin, desthiobiotin, avidin, neutravidin, streptavidin, aldehyde, hydrazide, hydrazine, aminooxy, an antibody, maleimide, an oligonucleotide, or a nucleic acid analog.

4. The method of claim 3, wherein the first functional group comprises biotin, digoxigenin (DIG), a thiol, an aldehyde, or an oligonucleotide.

5. The method of claim 2, wherein the coupling is reversible.

6. The method of claim 2, wherein the first fluid further comprises a second nucleotide coupled to a third functional group that is different from the first functional group, and the second fluid further comprises a second magnetic particle coupled to a fourth functional group that is different from the second functional group.

7. The method of claim 2, wherein the first fluid further comprises a second nucleotide coupled to at least two of the first functional group.

8. The method of claim 1, wherein a 3'-OH group of the first nucleotide is protected by a blocking group, the method further comprising removing the blocking group after detecting the captured first magnetic particle.

9. The method of claim 8, wherein the blocking group comprises azidomethyl.

10. The method of claim 1, further comprising contacting the polymerase and the captured nucleic acid template hybridized to the complementary strand, including the incorporated first nucleotide and the captured first magnetic particle, with a fourth fluid comprising a reagent that cleaves the first magnetic particle from the incorporated first nucleotide.

11. The method of claim 1, wherein the first magnetic particle has a diameter of about 10 nm to about 50 nm.

12. A composition, comprising:

a nucleic acid template;

a complementary strand hybridized to the nucleic acid template, a nucleotide of the complementary strand being coupled to a first functional group;

a polymerase coupled to a magnetically-responsive sensor and binding the nucleic acid template hybridized to the complementary strand, including the nucleotide coupled to the first functional group;

a fluid in contact with the polymerase and the captured nucleic acid template hybridized to the complementary strand, including the nucleotide coupled to the first functional group, the fluid comprising a first magnetic particle coupled to a second functional group configured to bind with the first functional group.

13. The composition of claim 12, wherein the second functional group comprises biotin, desthiobiotin, avidin, neutravidin, streptavidin, aldehyde, hydrazide, hydrazine, aminooxy, an antibody, maleimide, an oligonucleotide, or a nucleic acid analog.

14. The composition of claim 12, wherein the first functional group comprises biotin, digoxigenin (DIG), a thiol, an aldehyde, or an oligonucleotide.

15. The composition of claim 12, wherein the binding is reversible.

16. The composition of claim 12, wherein the fluid further comprises a second magnetic particle coupled to a third functional group that is different from the second functional group.

17. The composition of claim 12, wherein a 3'-OH group of the first nucleotide is protected by a blocking group.

18. The composition of claim 17, wherein the blocking group comprises azidomethyl.

19. The composition of claim 12, wherein the first magnetic particle has a diameter of about 10 nm to about 50 nm.

20. A device, comprising:

the composition of claim 12;

a magnetically-responsive sensor to which the polymerase is coupled, wherein the magnetic particle further is configured to cause a change in electrical resistance at the magnetically-responsive sensor when the second functional group binds with the first functional group; and circuitry configured to transmit a signal corresponding to the change in electrical resistance.

* * * * *